US007450746B2

(12) United States Patent
Yang et al.

(10) Patent No.: US 7,450,746 B2
(45) Date of Patent: Nov. 11, 2008

(54) SYSTEM AND METHOD FOR CARDIAC IMAGING

(75) Inventors: Fuxing Yang, Woodinville, WA (US); Jongtae Yuk, Redmond, WA (US); Vikram Chalana, Mill Creek, WA (US); Steven J. Shankle, Kirkland, WA (US); Stephen Dudycha, Bothell, WA (US); Gerald McMorrow, Kirkland, WA (US)

(73) Assignee: Verathon Inc., Bothell, WA (US)

( * ) Notice: Subject to any disclaimer, the term of this patent is extended or adjusted under 35 U.S.C. 154(b) by 280 days.

(21) Appl. No.: 11/460,182

(22) Filed: Jul. 26, 2006

(65) Prior Publication Data

US 2008/0181479 A1 Jul. 31, 2008

Related U.S. Application Data

(63) Continuation-in-part of application No. 11/213,284, filed on Aug. 26, 2005, and a continuation-in-part of application No. 11/119,355, filed on Apr. 29, 2005, and a continuation-in-part of application No. 10/701,955, filed on Nov. 5, 2003, now Pat. No. 7,087,022, and a continuation-in-part of application No. 10/443,126, filed on May 20, 2003, now Pat. No. 7,041,059, and a continuation-in-part of application No. 11/061,867, filed on Feb. 17, 2005, and a continuation-in-part of application No. 10/704,996, filed on Nov. 10, 2003, and a continuation-in-part of application No. 10/607, 919, filed on Jun. 27, 2003, now Pat. No. 6,884,217, and a continuation-in-part of application No. PCT/US03/24368, filed on Aug. 1, 2003, and a continuation-in-part of application No. PCT/US03/14785, filed on May 9, 2003, which is a continuation of application No. 10/165,556, filed on Jun. 7, 2002, now Pat. No. 6,676,605, application No. 11/460,182, which is a continuation-in-part of application No. 10/888,735, filed on Jul. 9, 2004, now abandoned, and a continuation-in-part of application No. 10/633,186, filed on Jul. 31, 2003, now Pat. No. 7,004,904, and a continuation-in-part of application No. 10/443,126.

(60) Provisional application No. 60/703,201, filed on Jul. 28, 2005, provisional application No. 60/566,127, filed on Apr. 30, 2004, provisional application No. 60/566,818, filed on Apr. 30, 2004, provisional application No. 60/545,576, filed on Feb. 17, 2004, provisional application No. 60/470,525, filed on May 12, 2003, provisional application No. 60/423,881, filed on Nov. 5, 2002, provisional application No. 60/400,624, filed on Aug. 2, 2002.

(51) Int. Cl.
*G06K 9/00* (2006.01)

(52) U.S. Cl. ........................ 382/131; 382/128; 382/130; 382/132

(58) Field of Classification Search ................. 382/128, 382/130, 131, 132
See application file for complete search history.

(56) References Cited

U.S. PATENT DOCUMENTS 5,151,856 A * 9/1992 Halmann et al. ............ 600/508

(Continued)

OTHER PUBLICATIONS

Gobbi et al.,Real-Time 3D Ultrasound for Intraoperative Surgical Guidance, J.P. Robarts Research Institute, University of Western Ontario.

(Continued)

*Primary Examiner*—Yosef Kassa
(74) *Attorney, Agent, or Firm*—Black Lowe & Graham; Mark D. Byrne

(57) ABSTRACT

Ultrasound systems and methods are described to measure changes in cardiac chamber volumes and organ wall areas, thicknesses, volumes and masses between the cardiac chambers using computer readable media employing image processing algorithms applied to 3D data sets acquired at systole and diastole. The systems for cardiac imaging includes an ultrasound transceiver configured to sense the mitral valve of a heart by Doppler ultrasound, an electrocardiograph connected with a patient and synchronized with the transceiver to acquire ultrasound-based 3D data sets during systole and diastole at a transceiver location determined by Doppler ultrasound affected by the mitral valve, and a computer readable medium configurable to process ultrasound imaging information from the 3D data sets communicated from the transceiver.

42 Claims, 53 Drawing Sheets

U.S. PATENT DOCUMENTS

| | | | | |
|---|---|---|---|---|
| 5,465,721 | A | 11/1995 | Kishimoto et al. | |
| 5,903,664 | A * | 5/1999 | Hartley et al. | 382/154 |
| 5,993,390 | A | 11/1999 | Savord et al. | |
| 6,515,657 | B1 * | 2/2003 | Zanelli | 345/419 |
| 6,569,101 | B2 | 5/2003 | Quistgaard et al. | |
| 6,650,927 | B1 * | 11/2003 | Keidar | 600/424 |
| 6,768,811 | B2 * | 7/2004 | Dinstein et al. | 382/128 |
| 6,780,152 | B2 | 8/2004 | Ustuner et al. | |
| 2002/0102023 | A1 | 8/2002 | Yamauchi | |

OTHER PUBLICATIONS

Krenning et al., Assessment of Left Ventricular Function by Three-Dimensional Echocardiography, Cardiovascular Ultrasound, Sep. 8, 2003.

Shiota et al., Real-Time 3D Echocardiography for Determining Right Ventricular Stroke Volume Journal of the American Heart Association.

* cited by examiner $$tran\_x = mass\_center\_x$$
$$tran\_y = mass\_center\_y$$
$$scaling = \sqrt{area\_ROI / area\_averageshape}$$
$$rotational = \begin{cases} if \quad |\theta| > \theta_{threshold} & \theta = \theta_{threshold} \\ \quad else & \theta \end{cases}$$

2D 30 degree views of left ventricle from six scan planes at systole and diastole 3D rendering of left ventricle 30 degree 2D views from six scan planes at systole and diastole

SYSTEM AND METHOD FOR CARDIAC IMAGING

PRIORITY CLAIM

This application claims priority to U.S. provisonal patent application Ser. No. 60/703,201 filed Jul. 28, 2005.

This application is a continuation-in-part of and claims priority to U.S. patent application Ser. No. 11/213,284 filed Aug. 26, 2005.

This application claims priority to and is a continuation-in-part of U.S. patent application Ser. No. 11/119,355 filed Apr. 29, 2005, which claims priority to U.S. provisional patent application Ser. No. 60/566,127 filed Apr. 30, 2004. This application also claims priority to and is a continuation-in-part of U.S. patent application Ser. No. 10/701,955 filed Nov. 5, 2003, now U.S. Pat. No. 7,087,022 which in turn claims priority to and is a continuation-in-part of U.S. patent application Ser. No. 10/443,126 filed May 20, 2003 now U.S. Pat. No. 7,041,059.

This application claims priority to and is a continuation-in-part of U.S. patent application Ser. No. 11/061,867 filed Feb. 17, 2005, which claims priority to U.S. provisional patent application Ser. No. 60/545,576 filed Feb. 17, 2004 and U.S. provisional patent application Ser. No. 60/566,818 filed Apr. 30, 2004.

This application is also a continuation-in-part of and claims priority to U.S. patent application Ser. No. 10/704,996 filed Nov. 10, 2003.

This application claims priority to and is a continuation-in-part of U.S. patent application Ser. No. 10/607,919 filed Jun. 27, 2003 now U.S. Pat. No. 6,884,217.

This application is a continuation-in-part of and claims priority to PCT application Ser. No. PCT/US03/24368 filed Aug. 1, 2003, which claims priority to U.S. provisional patent application Ser. No. 60/423,881 filed Nov. 5, 2002 and U.S. provisional patent application Ser. No. 60/400,624 filed Aug. 2, 2002.

This application is also a continuation-in-part of and claims priority to PCT Application Serial No. PCT/US03/14785 filed May 9, 2003, which is a continuation of U.S. patent application Ser. No. 10/165,556 filed Jun. 7, 2002 now U.S. Pat. No. 6,676,605.

This application is also a continuation-in-part of and claims priority to U.S. patent application Ser. No. 10/888,735 filed Jul. 9, 2004 now abandoned.

This application is also a continuation-in-part of and claims priority to U.S. patent application Ser. No. 10/633,186 filed Jul. 31, 2003 now U.S. Pat. No. 7,004,904 which claims priority to U.S. provisional patent application Ser. No. 60/423,881 filed Nov. 5, 2002 and to U.S. patent application Ser. No. 10/443,126 filed May 20, 2003 now U.S. Pat. No. 7,041,059 which claims priority to U.S. provisional patent application Ser. No. 60/423,881 filed Nov. 5, 2002 and to U.S. provisional application 60/400,624 filed Aug. 2, 2002. This application also claims priority to U.S. provisional patent application Ser. No. 60/470,525 filed May 12, 2003, and to U.S. patent application Ser. No. 10/165,556 filed Jun. 7, 2002. All of the above applications are herein incorporated by reference in their entirety as if fully set forth herein.

FIELD OF THE INVENTION

An embodiment of the invention relates generally to ultrasound-based diagnostic systems and procedures.

BACKGROUND OF THE INVENTION

Computer based analysis of medical images pertaining cardiac structures allows diagnosis of cardiovascular diseases. Identifying the heart chambers, the endocardium, epicardium, ventricular volumes, and wall thicknesses during various stages of the cardiac cycle provides the physician to access disease state and prescribe therapeutic regimens. There is a need to non-invasively and accurately derive information of the heart during its beating cycle between systole and diastole.

SUMMARY OF THE INVENTION

The description of image acquisition and processing systems and methods to automatically detect the boundaries of shapes of structures within a region of interest of an image or series of images. The automatically segmented shapes are further image processed to determine thicknesses, areas, volumes, masses and changes thereof as the structure of interest experiences dynamic change.

BRIEF DESCRIPTION OF THE DRAWINGS

Embodiments of the present invention are described in detail below with reference to the following drawings.

Figure 12:
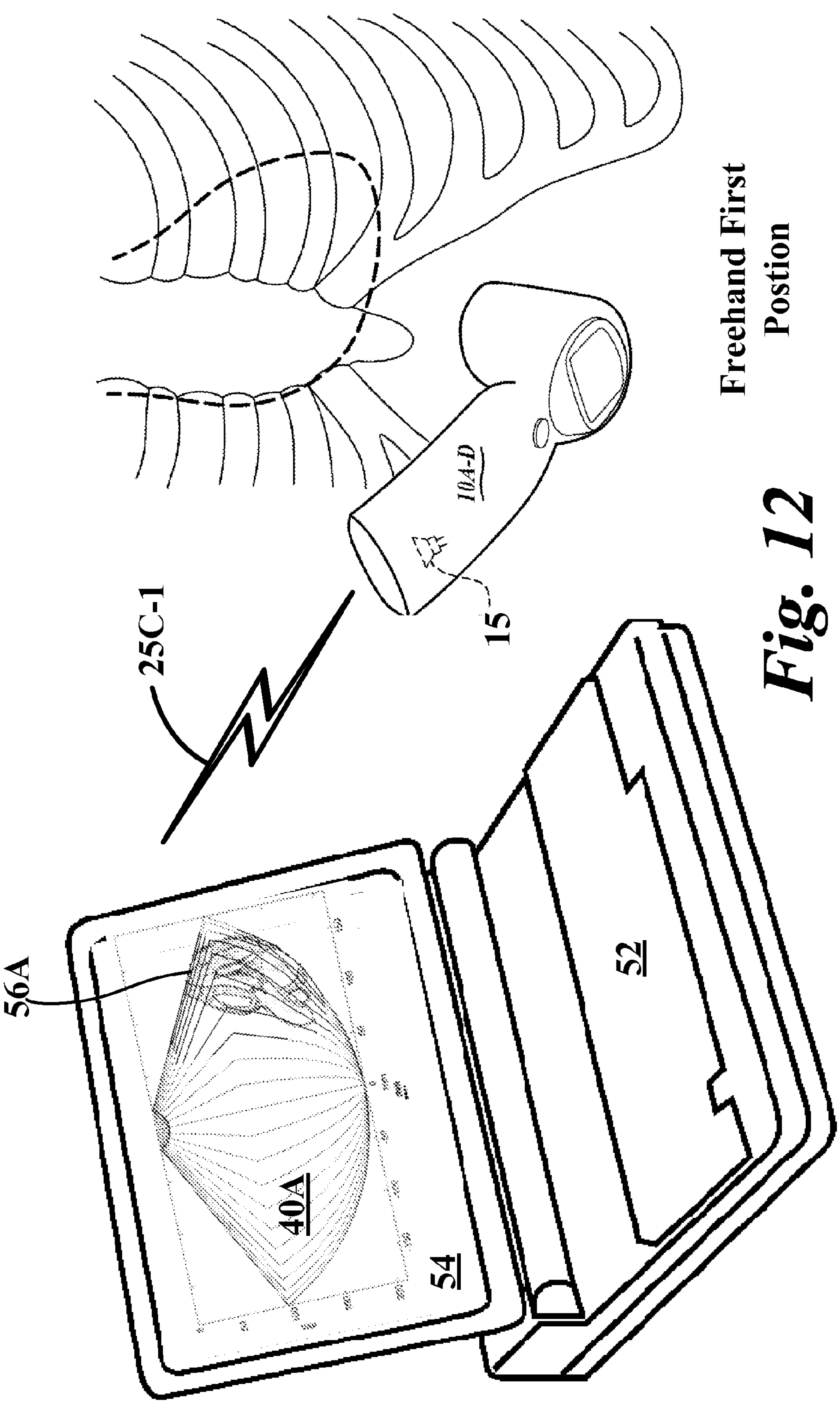
Figure 13:
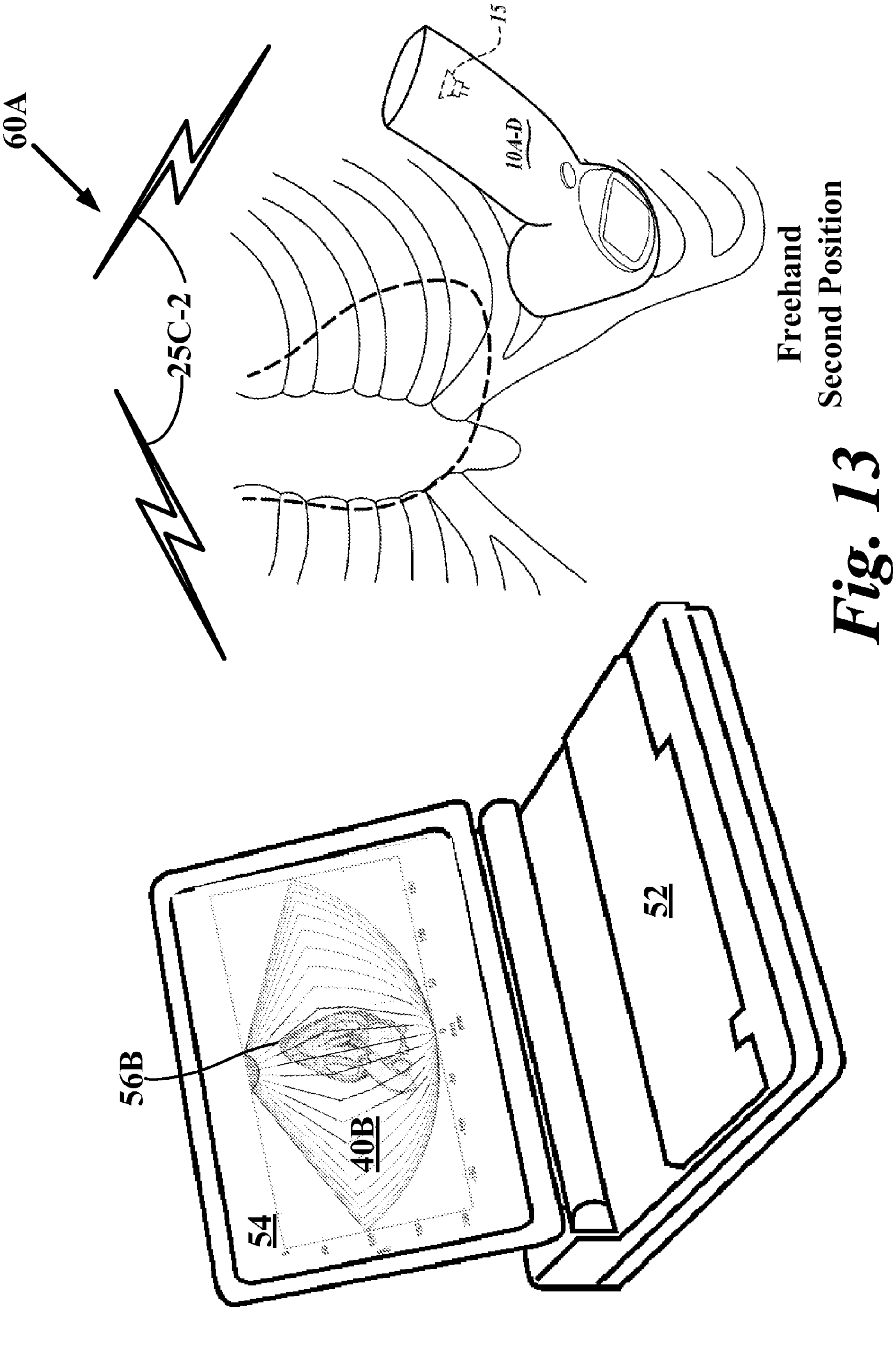
Figure 14:
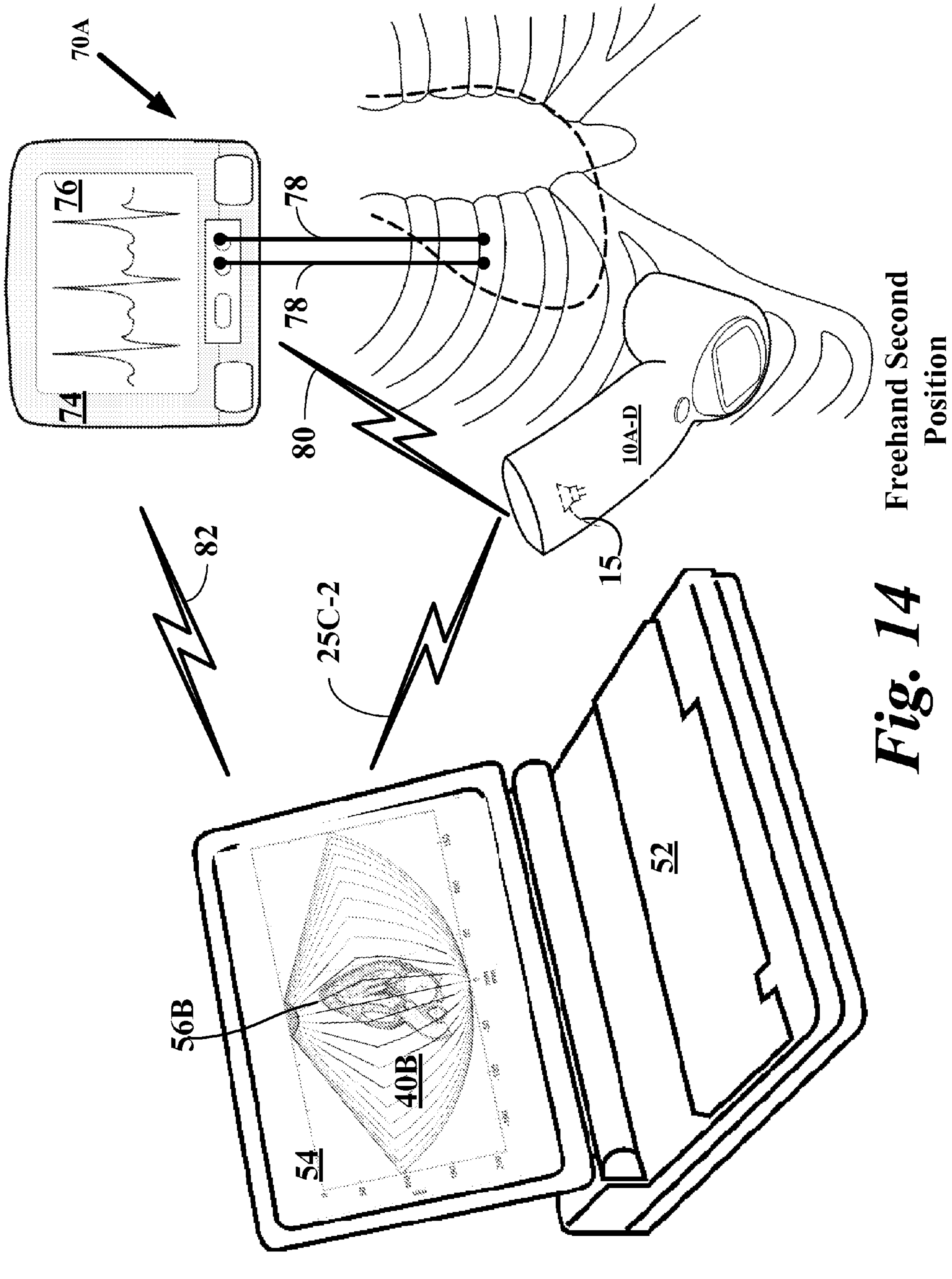
Figure 15:
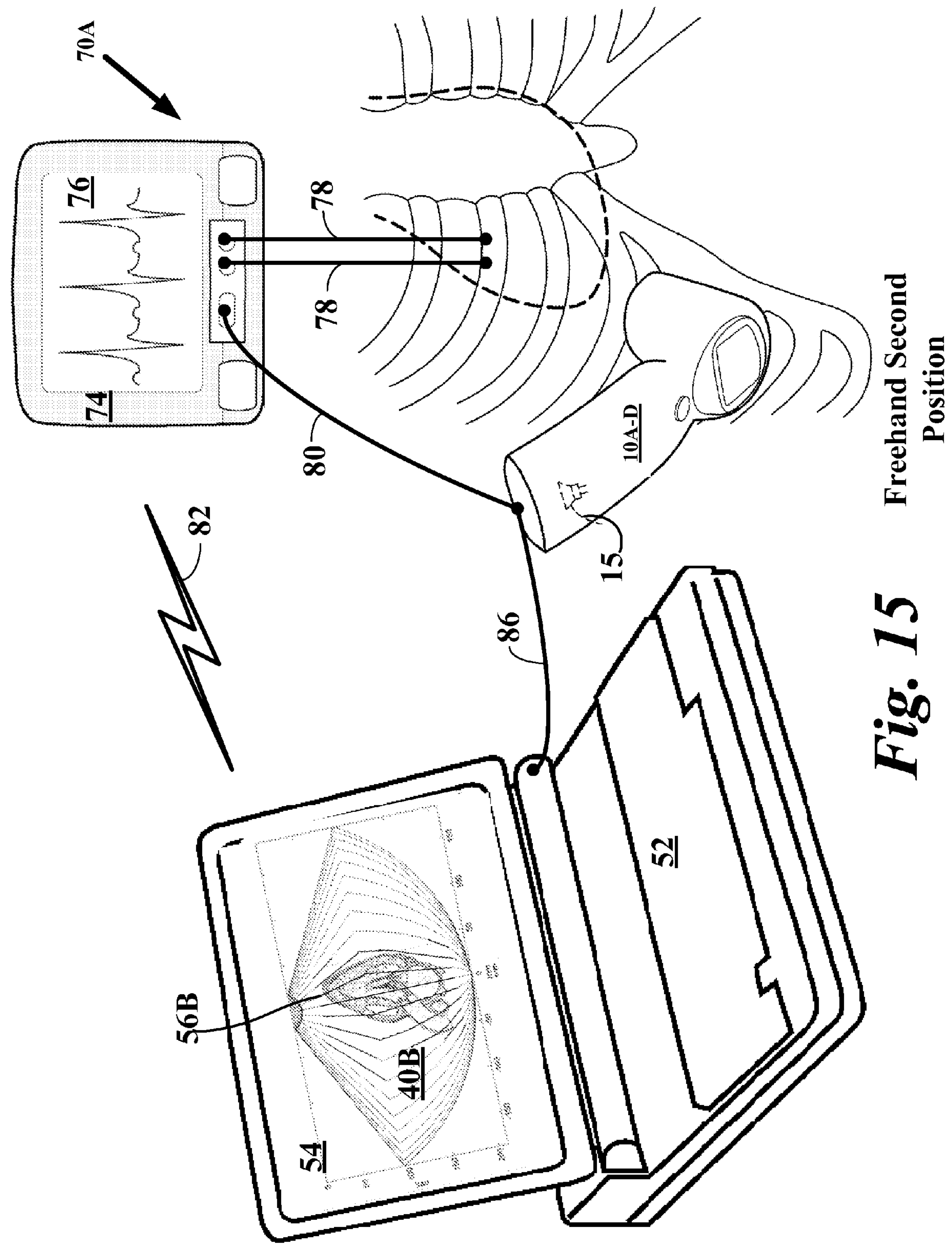
Figure 16:
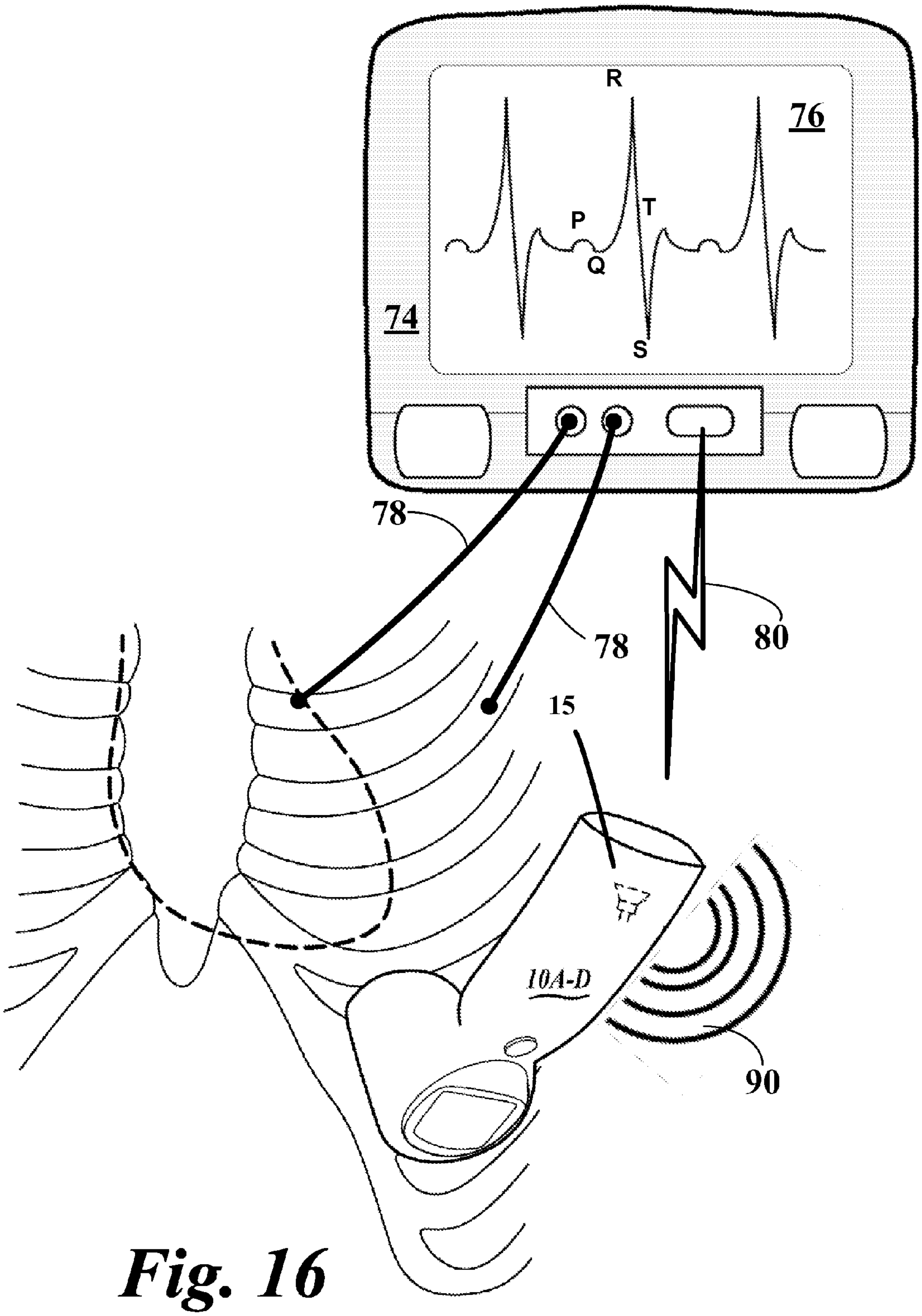
Figure 17:
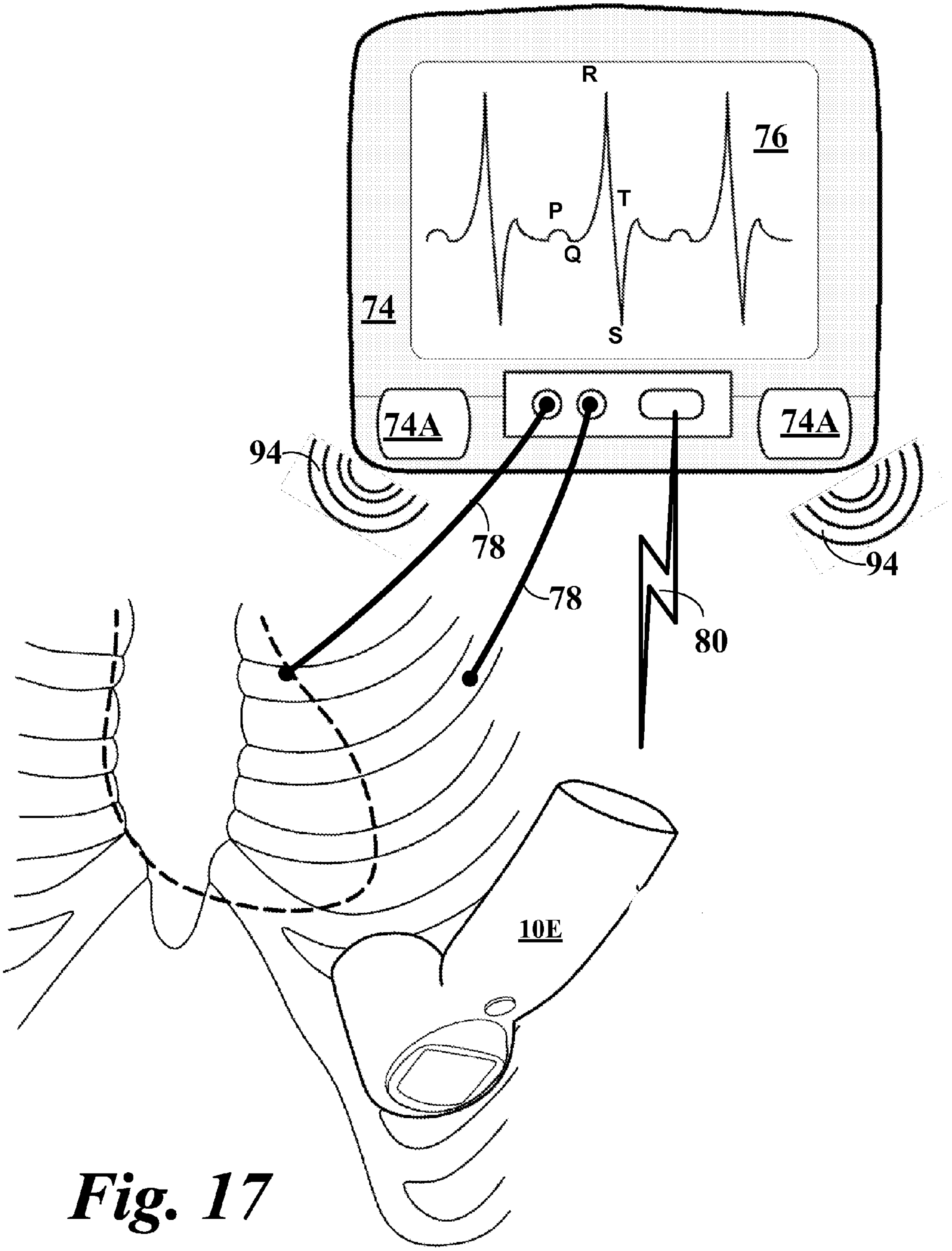
Figure 18:
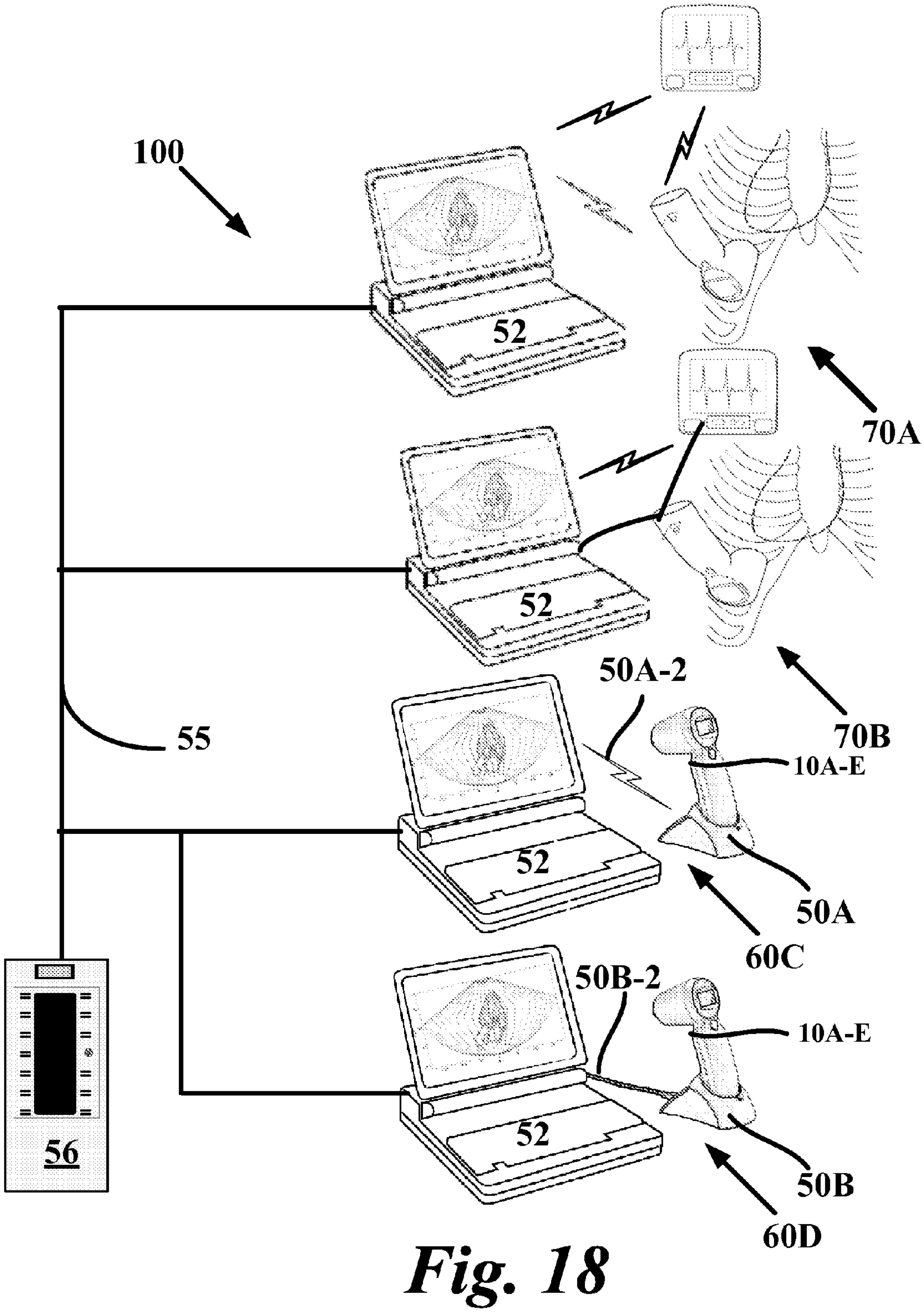
Figure 19:
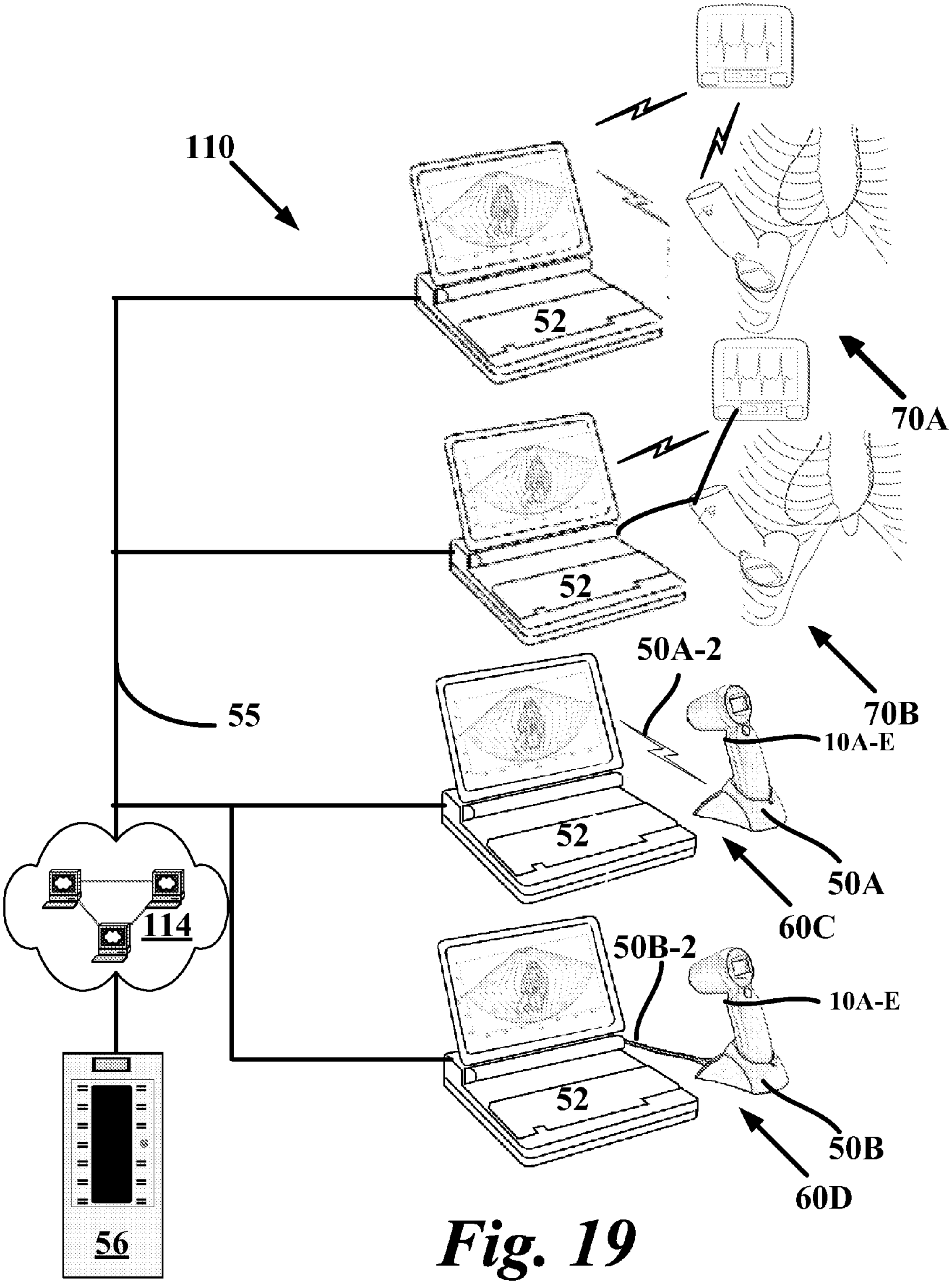
Figure 20:
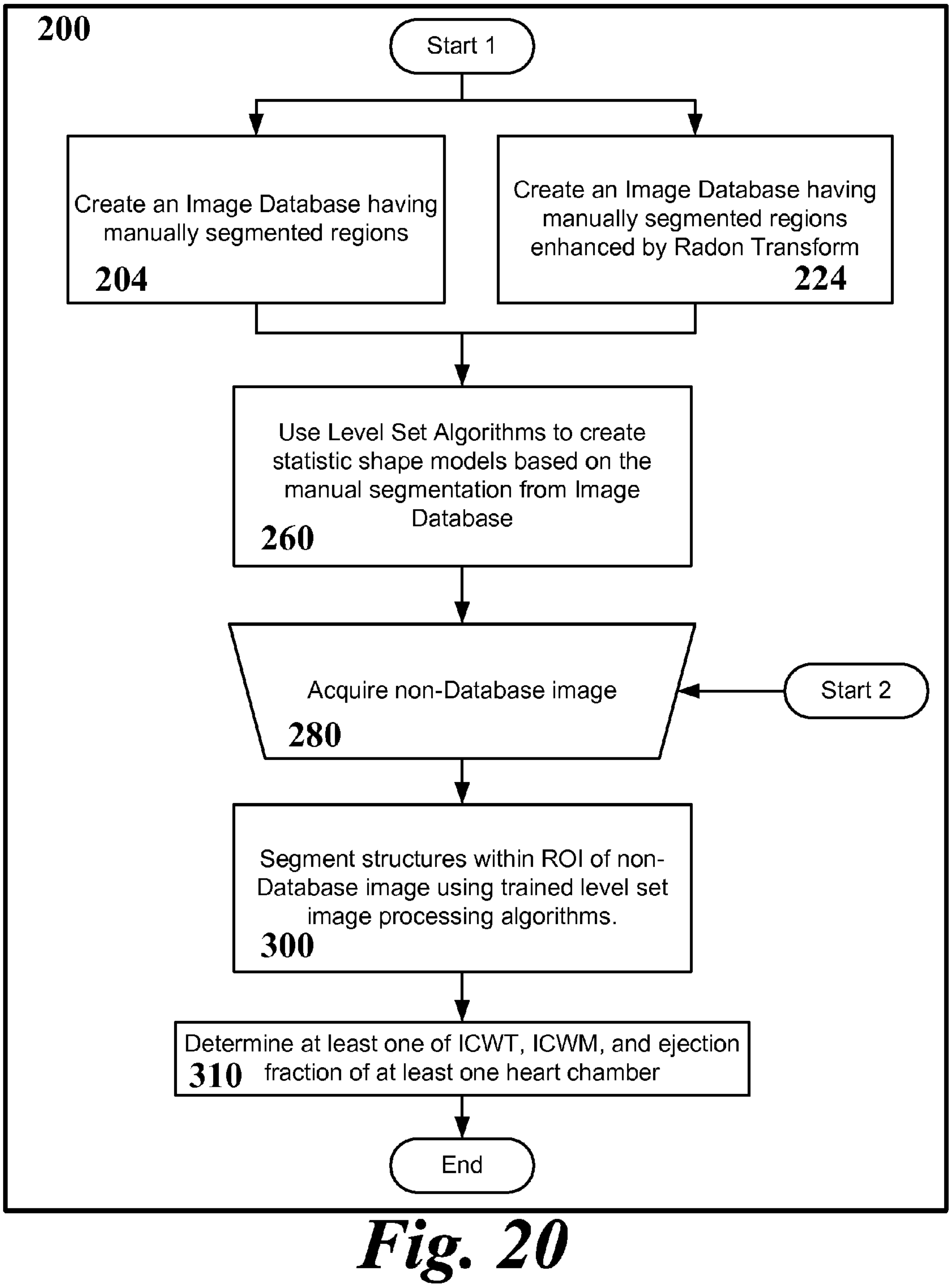
Figure 21:
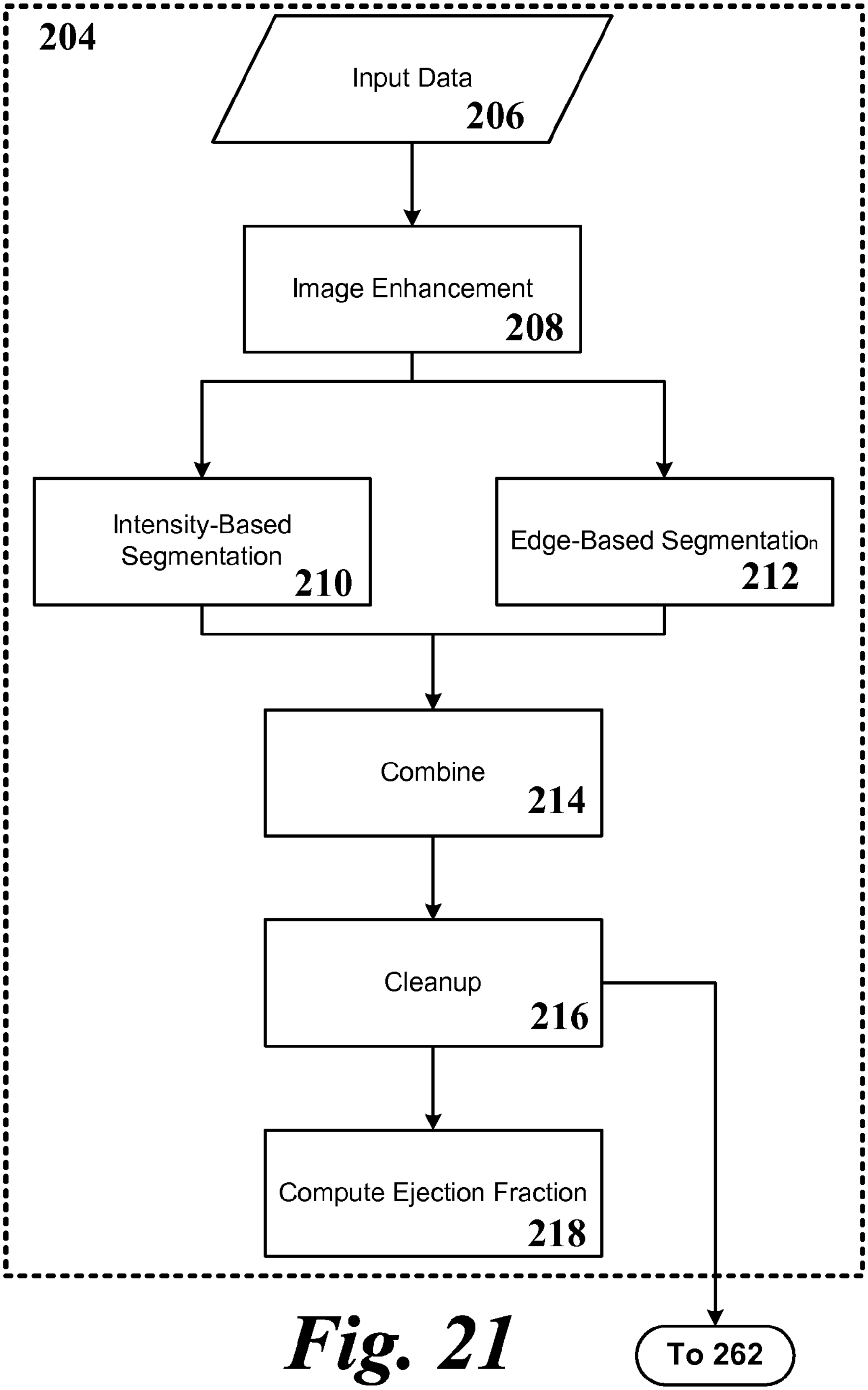
Figure 22:
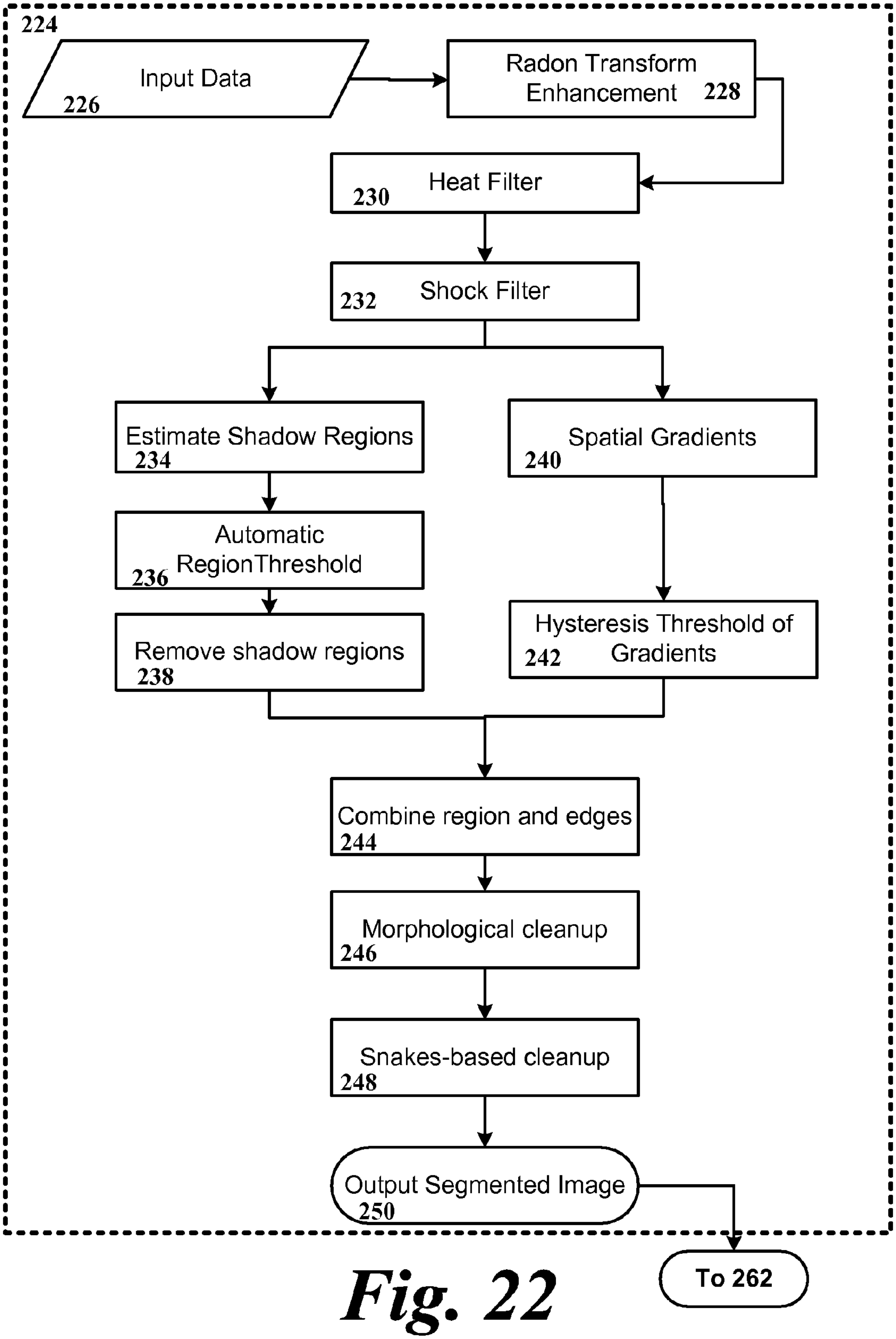
Figure 23A:
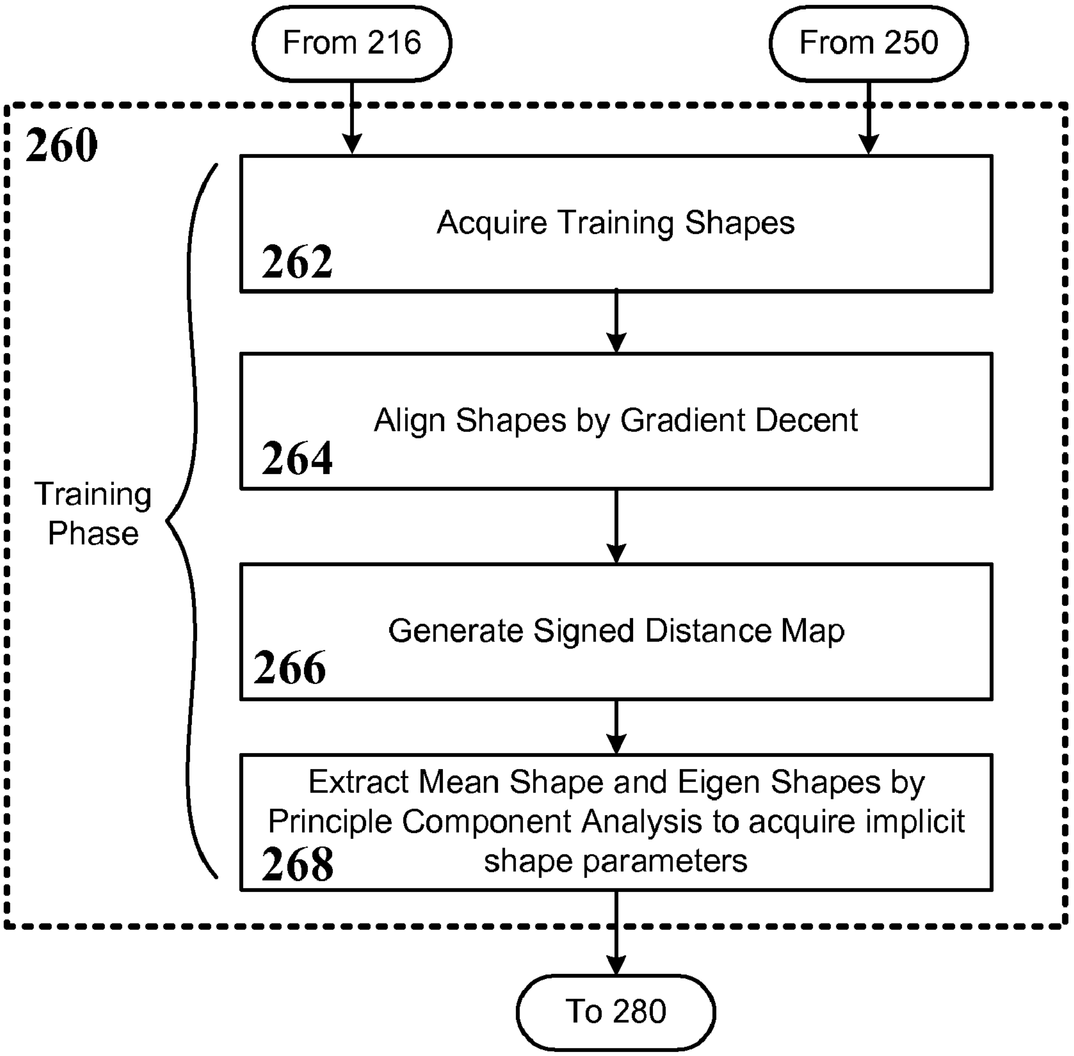
Figure 23B:
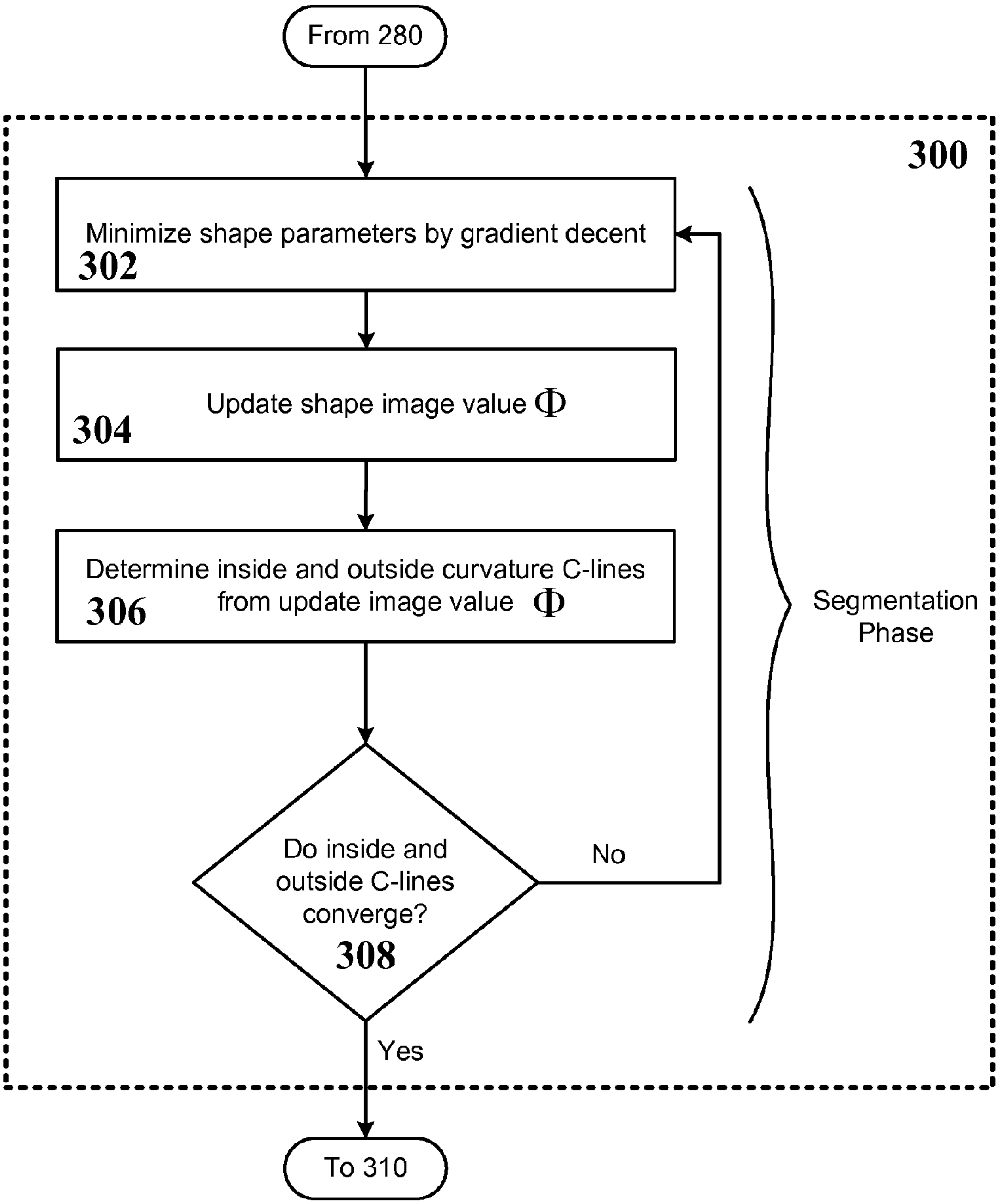
Figure 24:
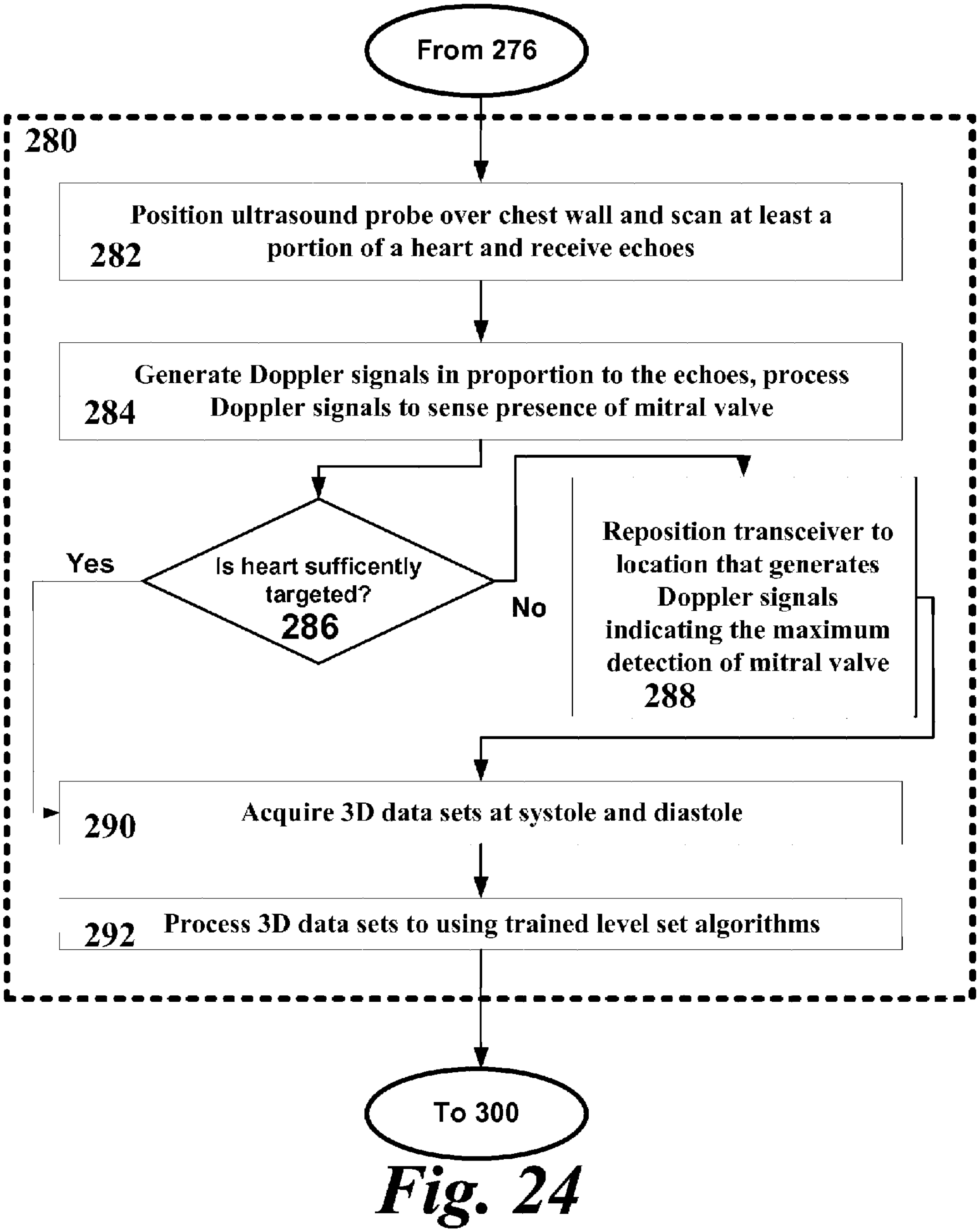
Figure 25:
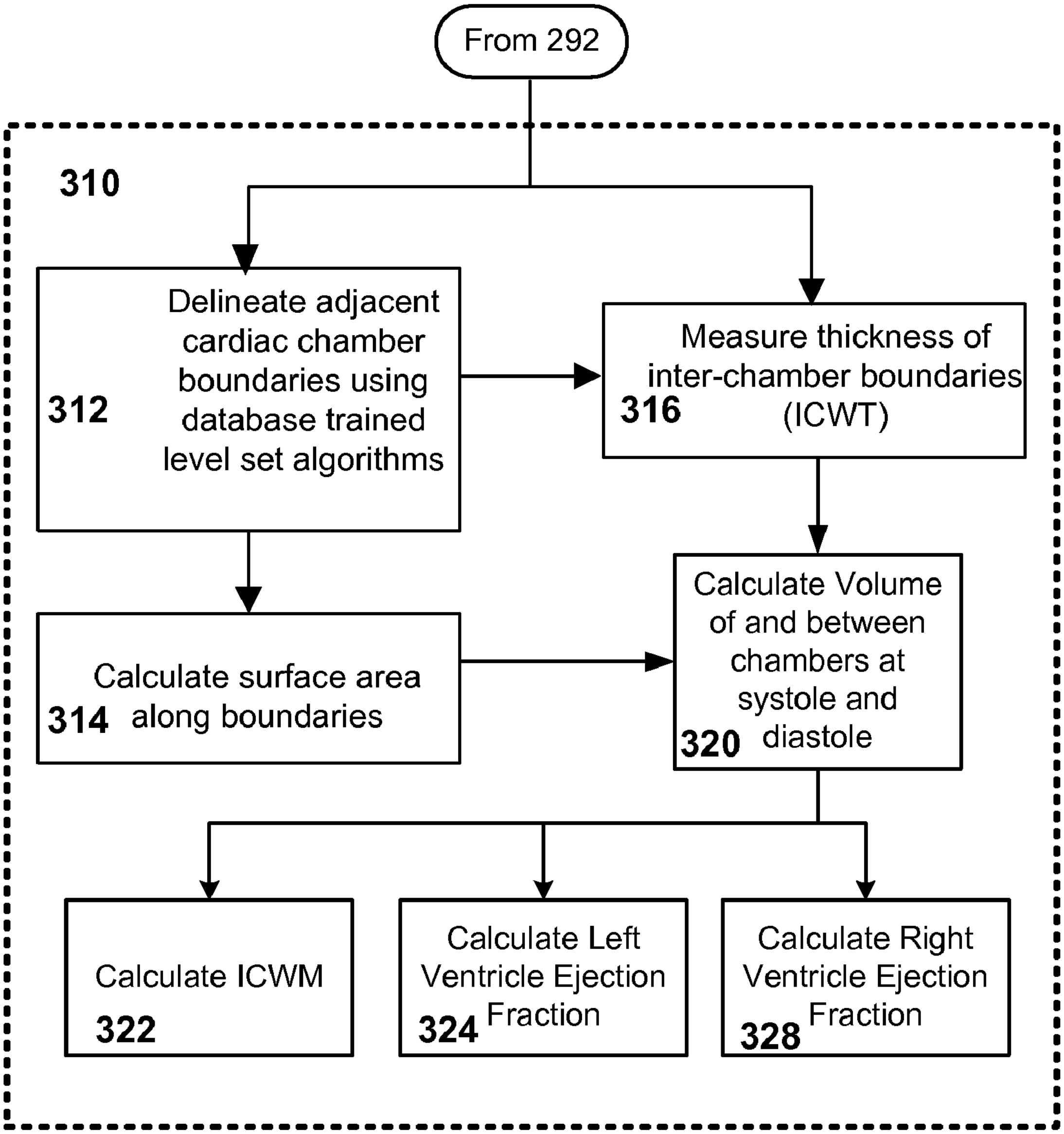
Figure 26:
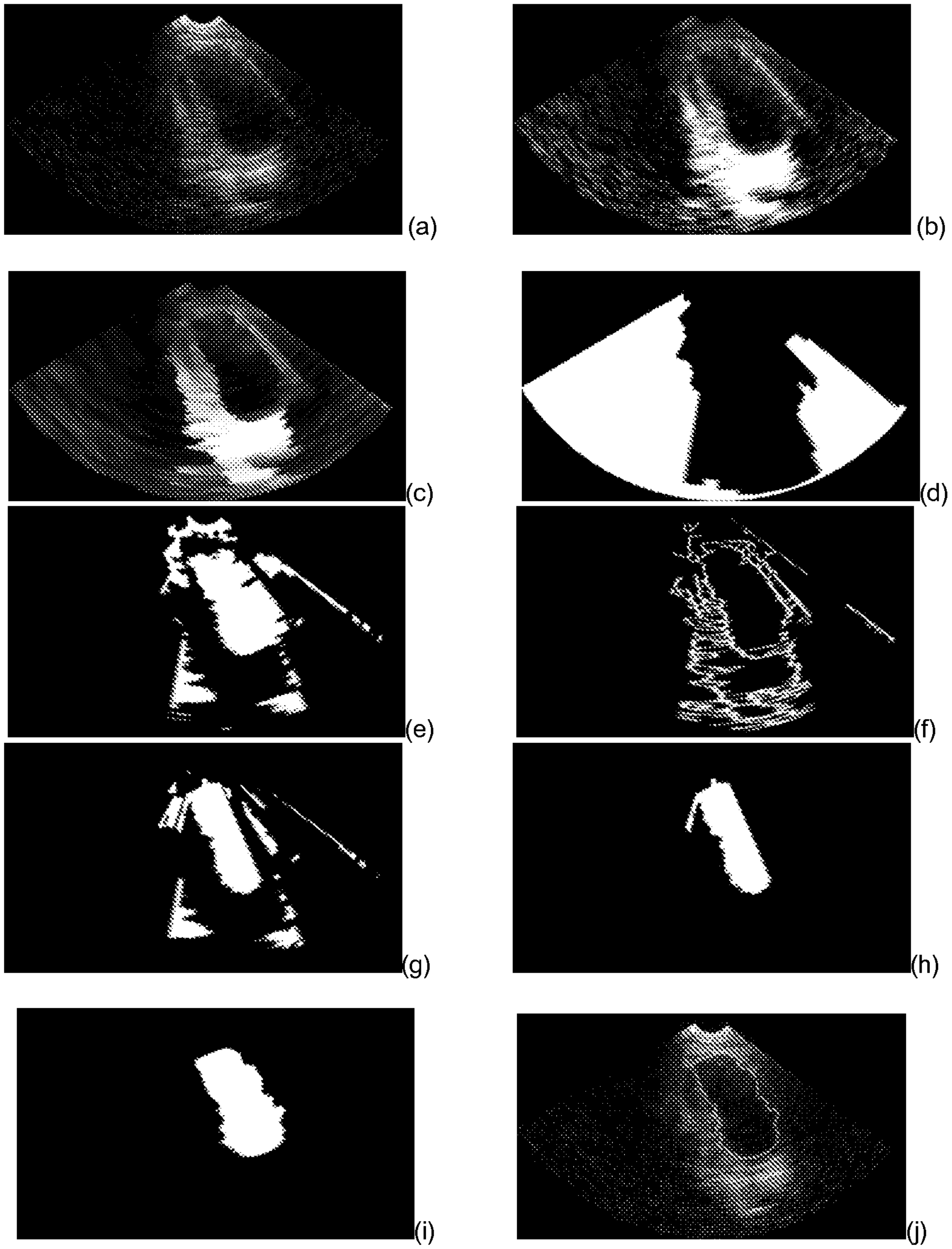
Figure 27:
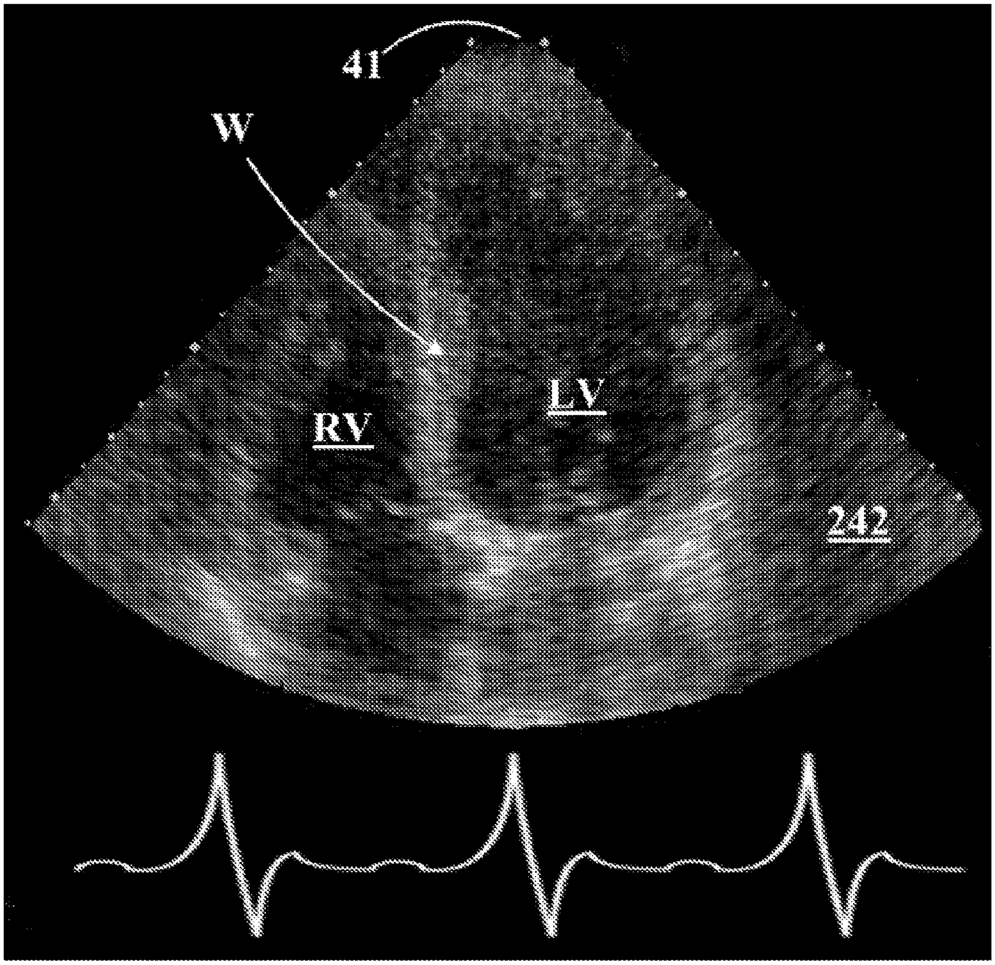
Figure 28:
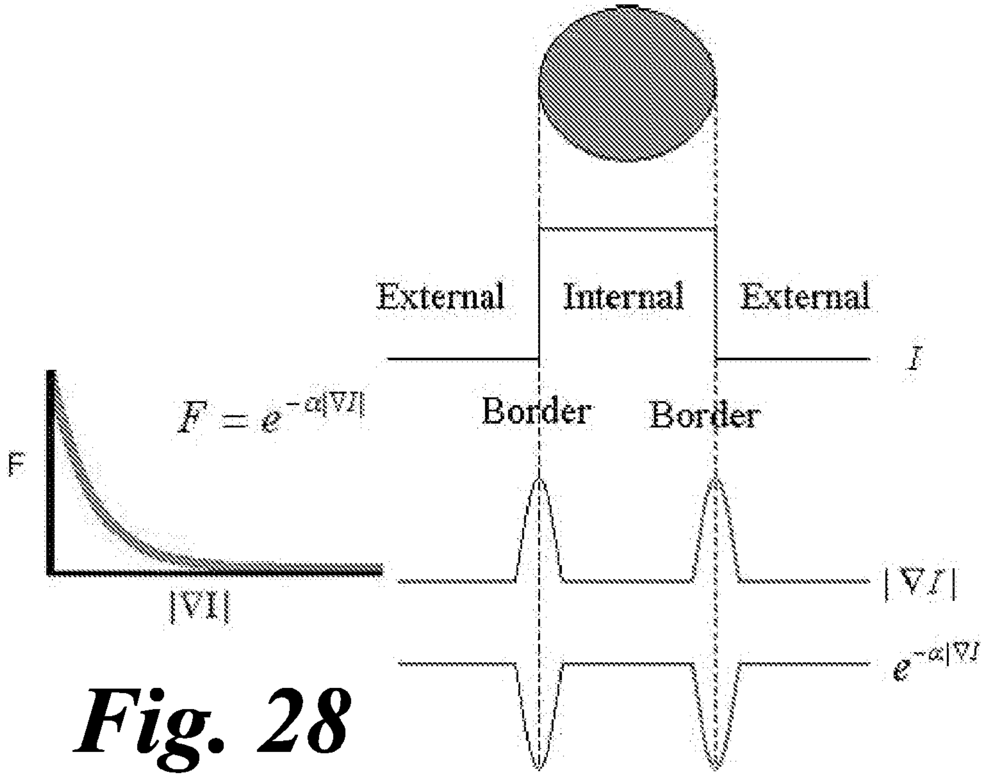
Figure 29:
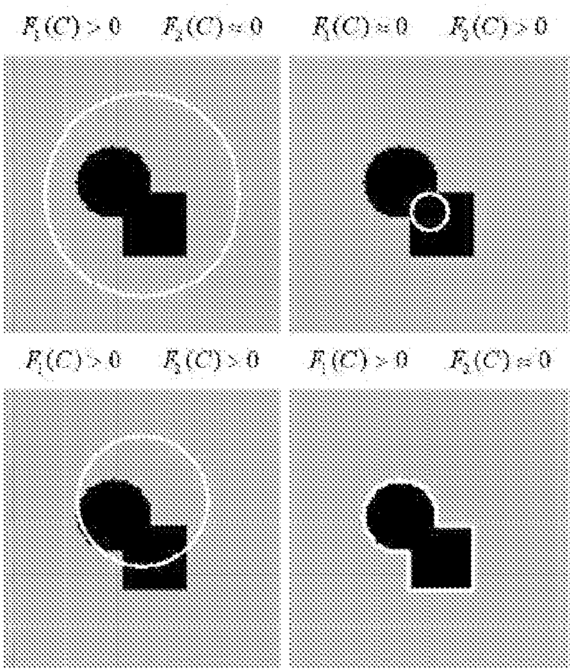

and timing to acquire RFUS images at cardiac systole and diastole to help determine the cardiac ejection fractions of the left and/or right ventricles;

FIG. 12 depicts an alternate embodiment of the cardiac imaging system using an electrocardiograph in communication with a wireless ultrasound transceiver displaying an off-centered cardiac region of interest (ROI);

FIG. 13 depicts an alternate embodiment of the cardiac imaging system using an electrocardiograph in communication with a wireless ultrasound transceiver displaying a centered cardiac ROI;

FIG. 14 depicts an alternate embodiment of the cardiac imaging system using an electrocardiograph in communication with a wired connected ultrasound transceiver;

FIG. 15 schematically depicts an alternate embodiment of the cardiac imaging system during Doppler targeting with microphone equipped transceivers 10A-D;

FIG. 16 schematically depicts an alternate embodiment of the cardiac imaging system during Doppler targeting of a transceiver with a speaker equipped electrocardiograph;

FIG. 17 schematically depicts an alternate embodiment of the cardiac imaging system during Doppler targeting of a speaker-less transceiver 10E with a speaker equipped electrocardiograph;

FIG. 18 is a schematic illustration and partial isometric view of a network connected cardio imaging ultrasound system 100 in communication with ultrasound imaging systems 60A-D;

FIG. 19 is a schematic illustration and partial isometric view of an Internet connected cardio imaging ultrasound system 110 in communication with ultrasound imaging systems 60A-D;

FIG. 20 is an algorithm flowchart 200 for the method to measure and determine heart chamber volumes, changes in heart chamber volumes, ICWT and ICWM;

FIG. 21 is an expansion of sonographer-executed sub-algorithm 204 of flowchart in FIG. 20 that utilizes a 2-step enhancement process;

FIG. 22 is an expansion of sonographer-executed sub-algorithm 224 of flowchart in FIG. 20 that utilizes a 3-step enhancement process;

FIG. 23A is an expansion of sub-algorithm 260 of flowchart algorithm depicted in FIG. 20;

FIG. 23B is an expansion of sub-algorithm 300 of flowchart algorithm depicted in FIG. 20 for application to non-database images acquired in process block 280;

FIG. 24 is an expansion of sub-algorithm 280 of flowchart algorithm 200 in FIG. 20;

FIG. 25 is an expansion of sub-algorithm 310 of flowchart algorithm 200 in FIG. 20;

FIG. 26 is an 8-image panel exemplary output of segmenting the left ventricle by processes of sub-algorithm 220;

FIG. 27 presents a scan plane image with ROI of the heart delineated with echoes returning from 3.5 MHz pulsed ultrasound;

FIG. 28 is a schematic of application of snakes processing block of sub-algorithm 220 to an active contour model;

FIG. 29 is a schematic of application of level-set processing block of sub-algorithm 260 of FIG. 23 to an active contour model.

Figure 30:
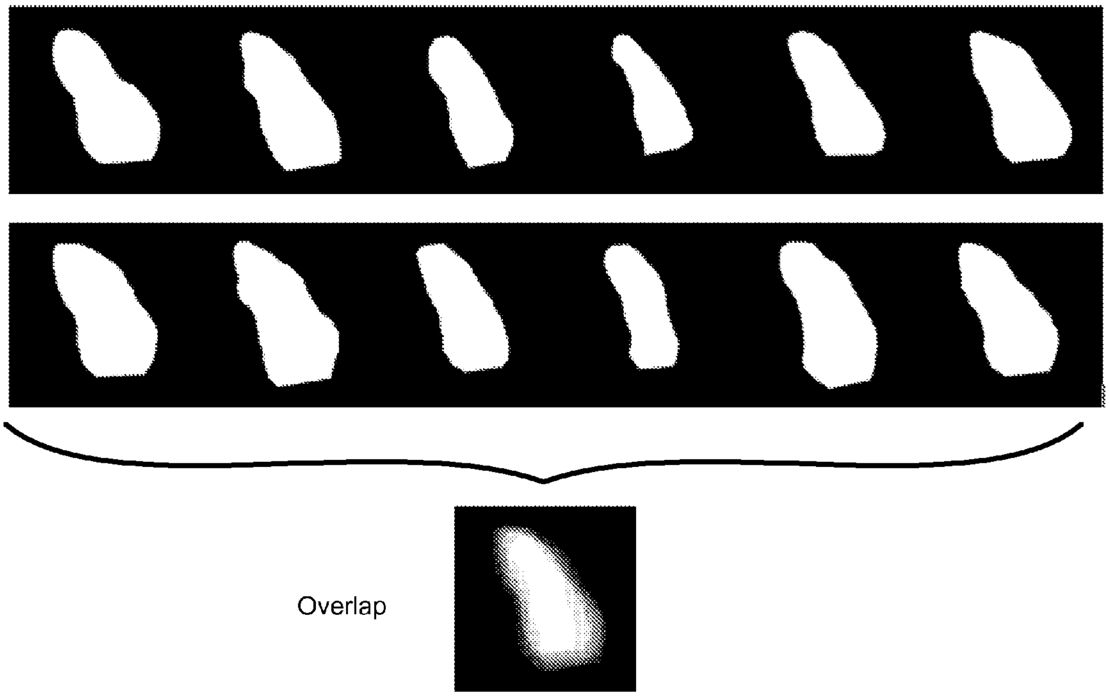
Figure 31:
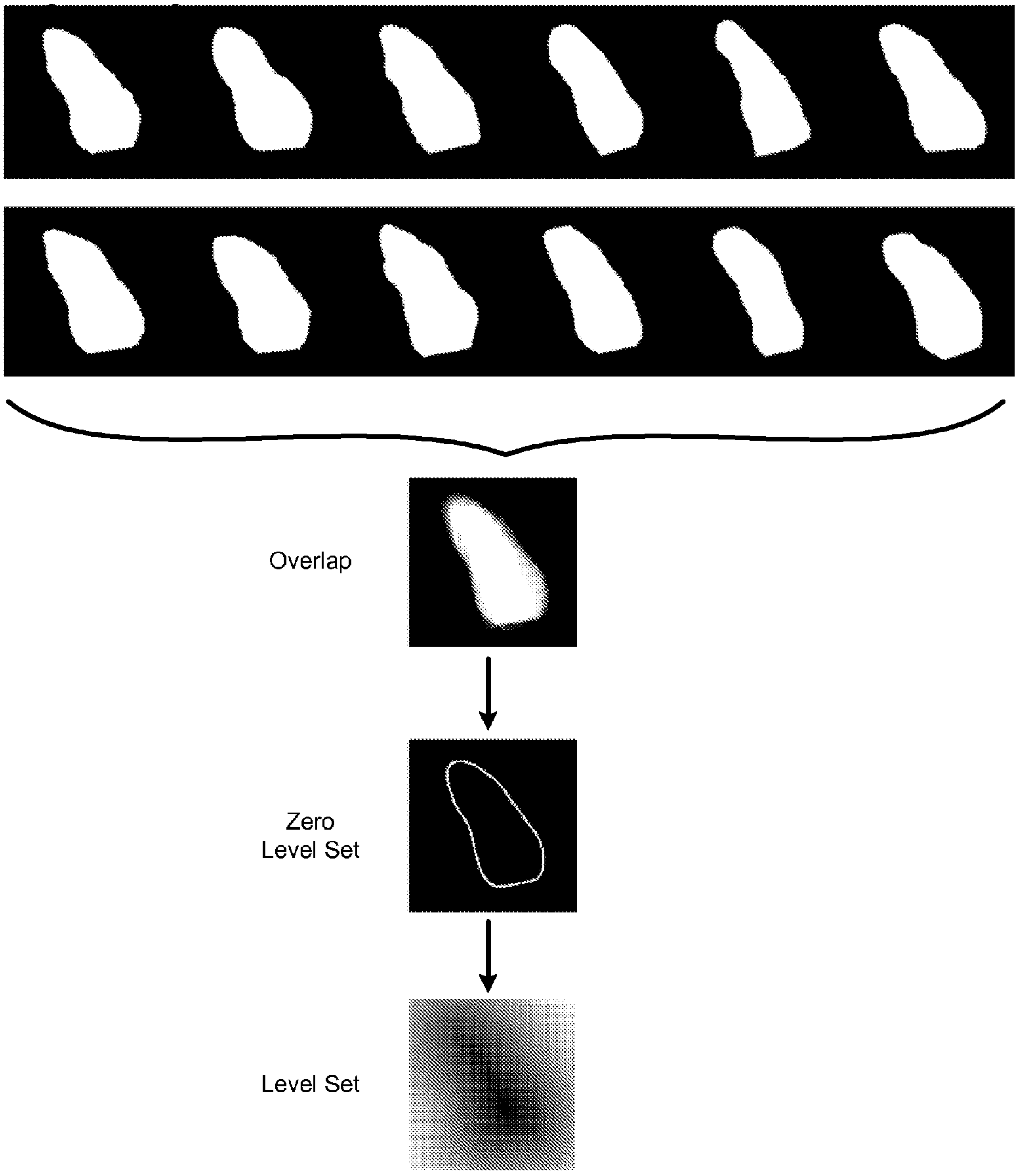
Figure 32:
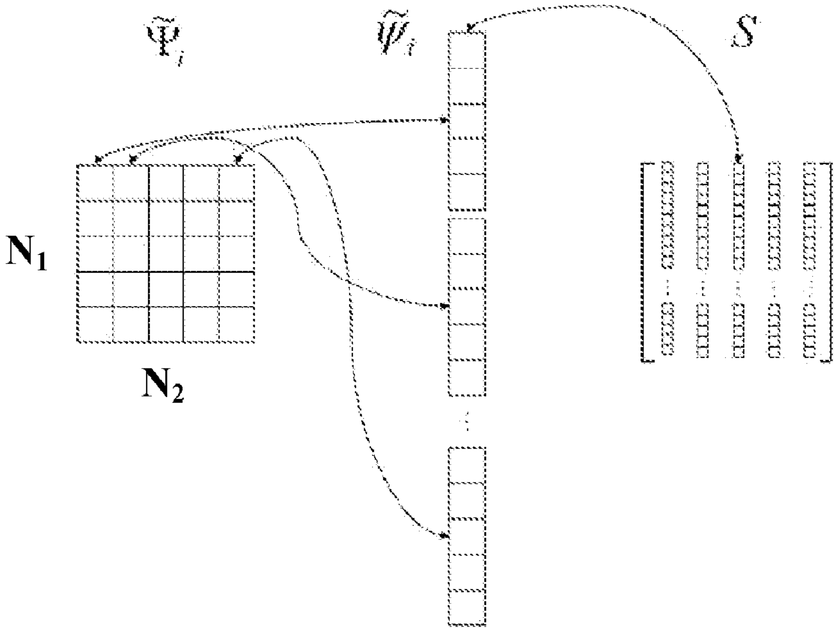
Figure 33:
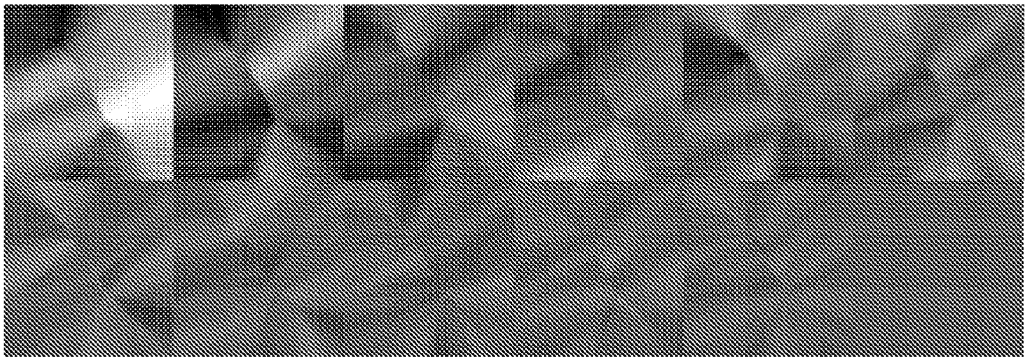
Figure 34:
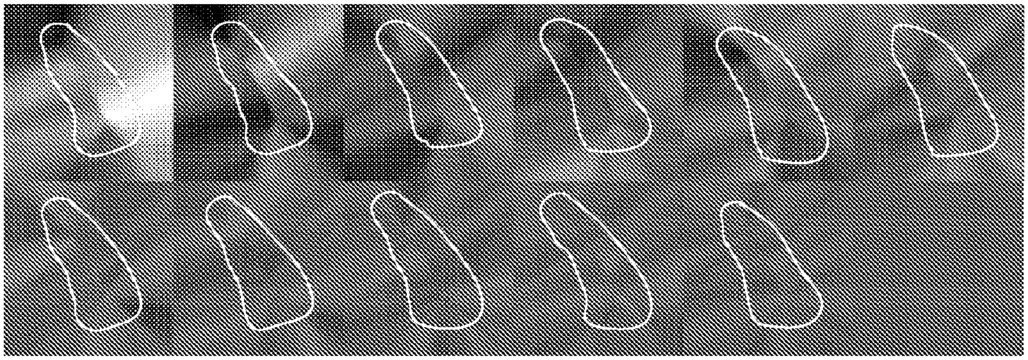
Figure 35:
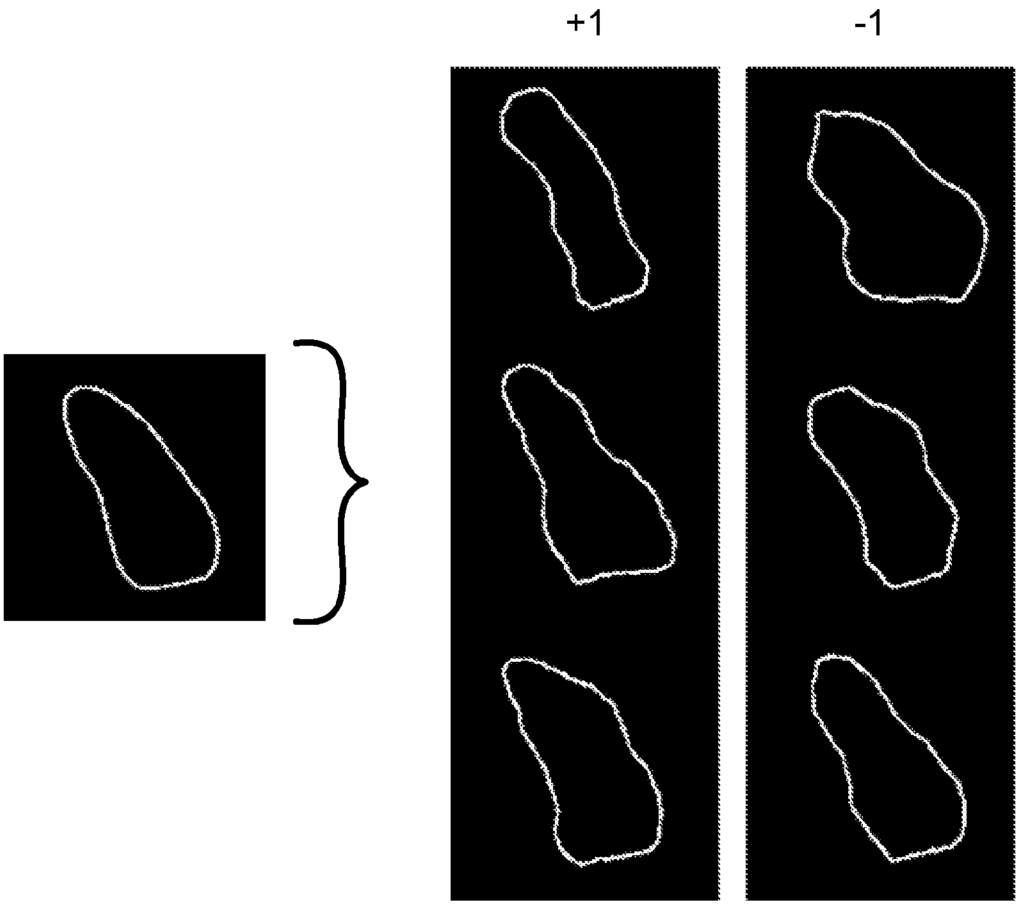
Figure 36:
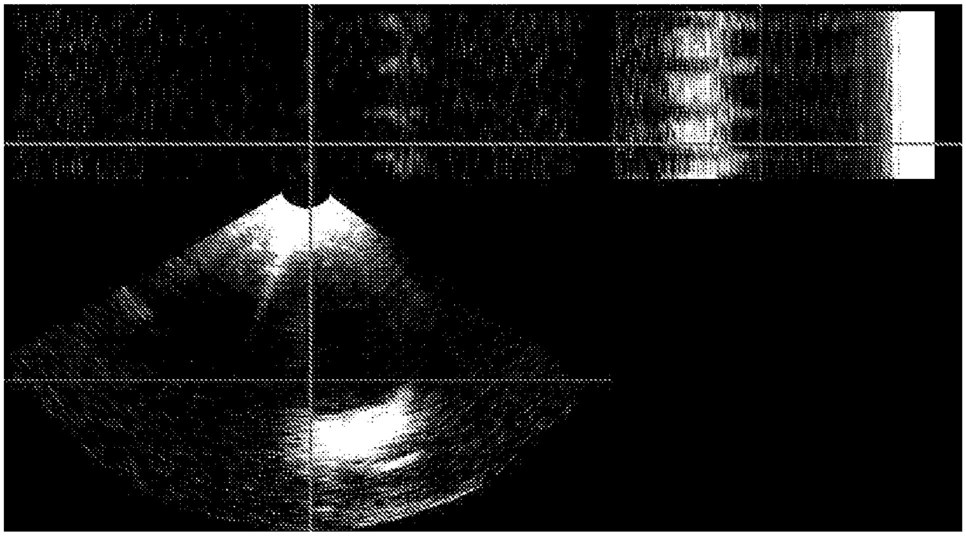
Figure 37:
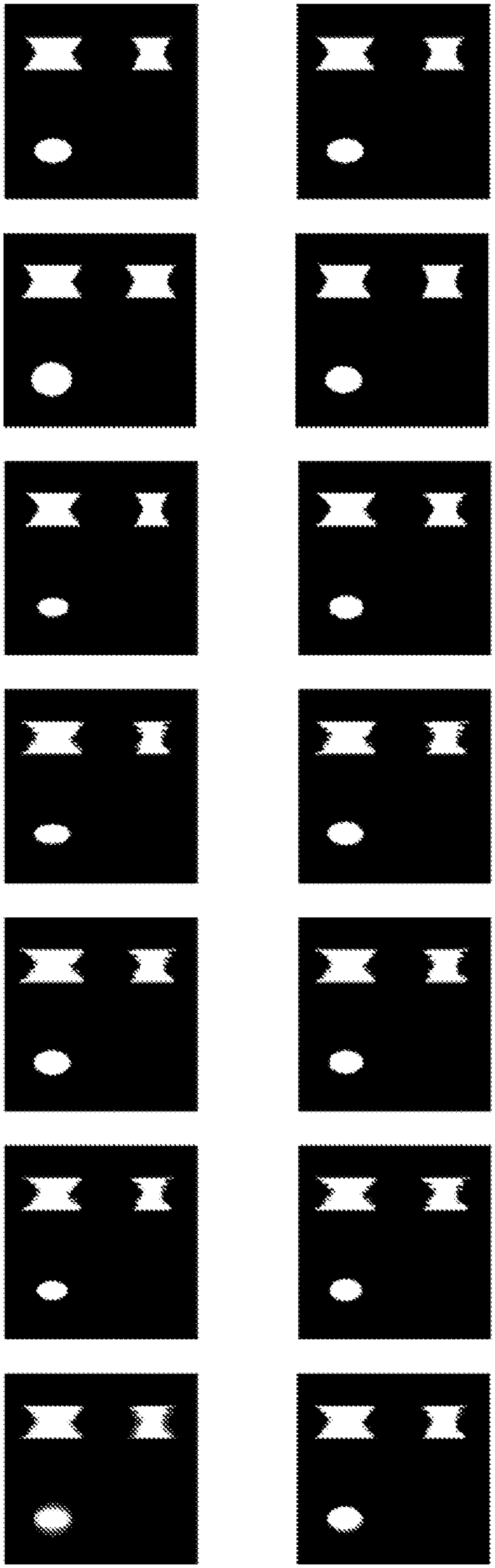
Figure 38:
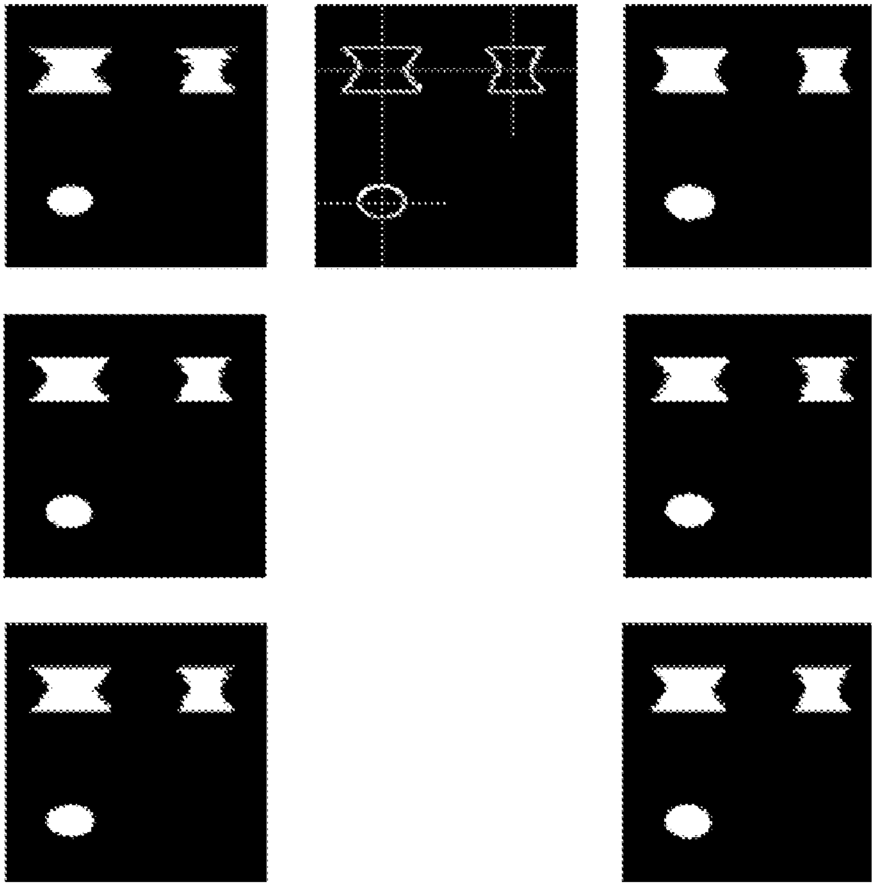
Figure 39:
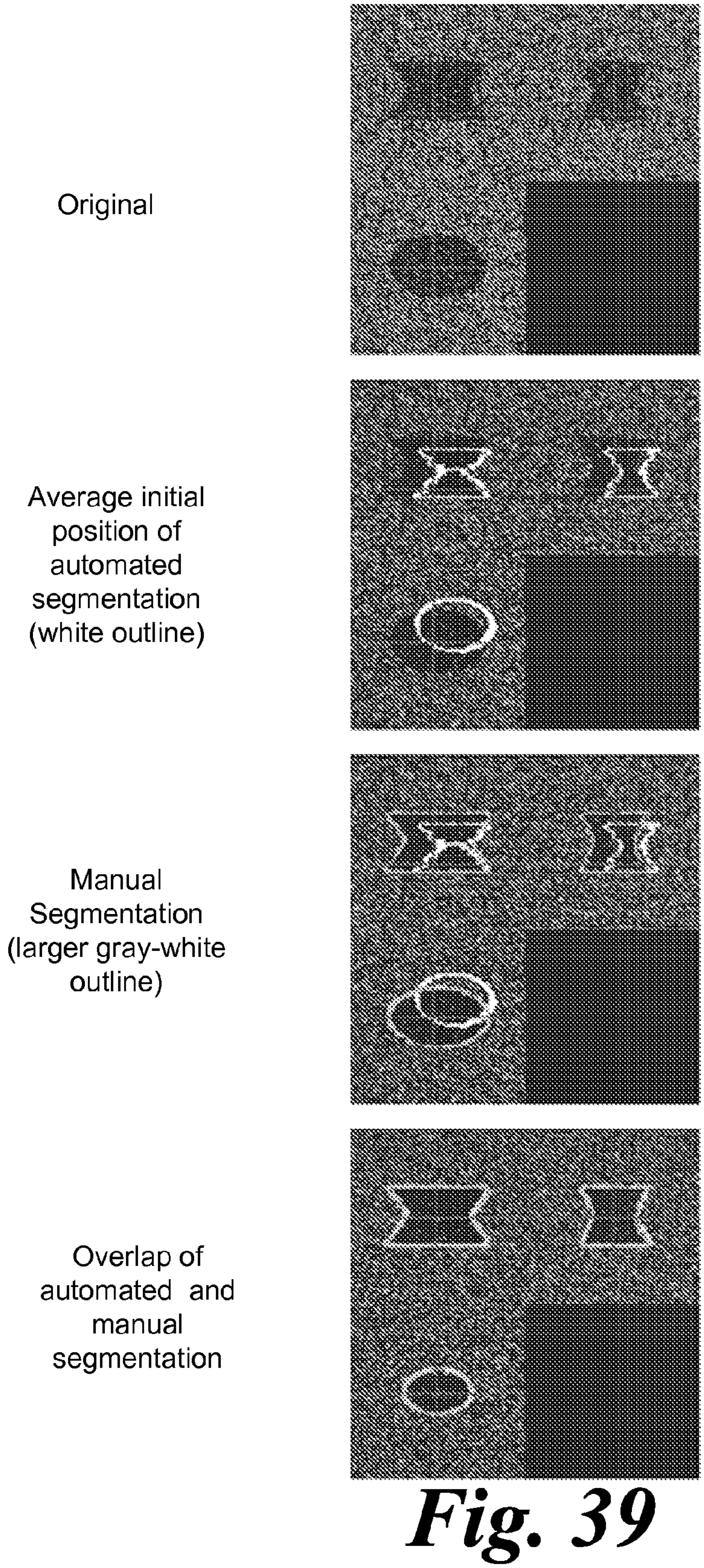
Figure 40:
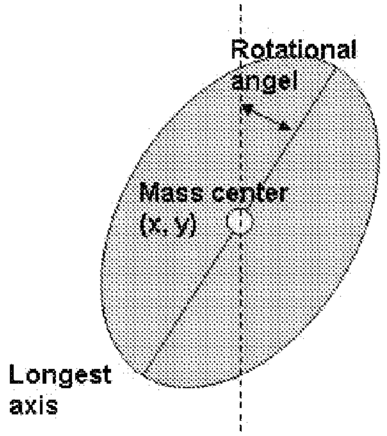
Figure 41:
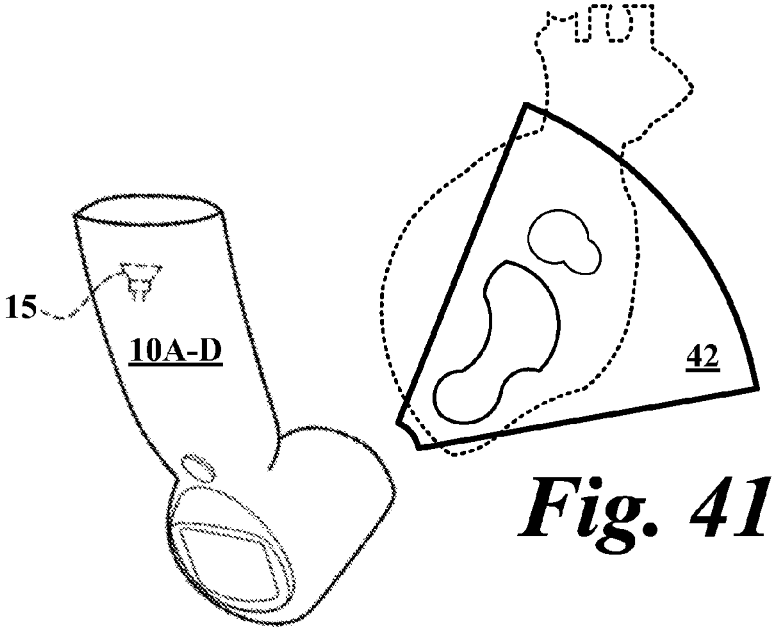
Figure 42:
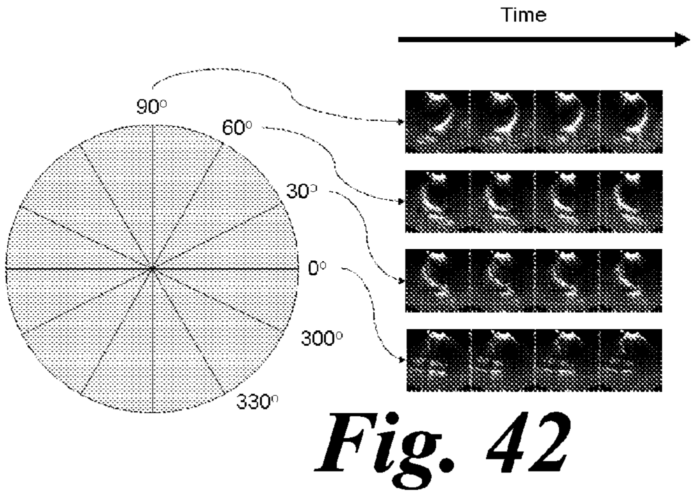
Figure 43:
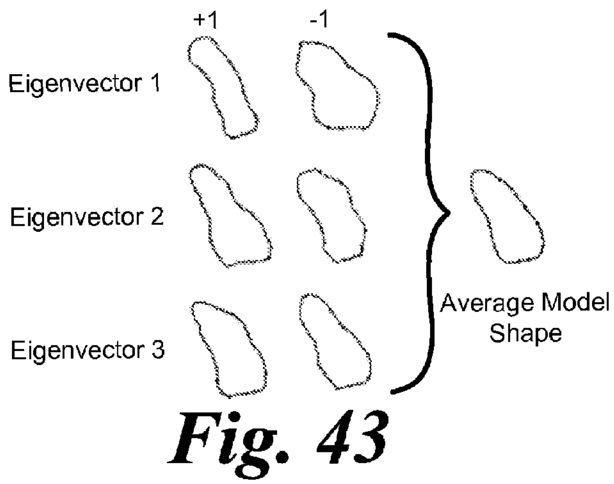
Figure 44:
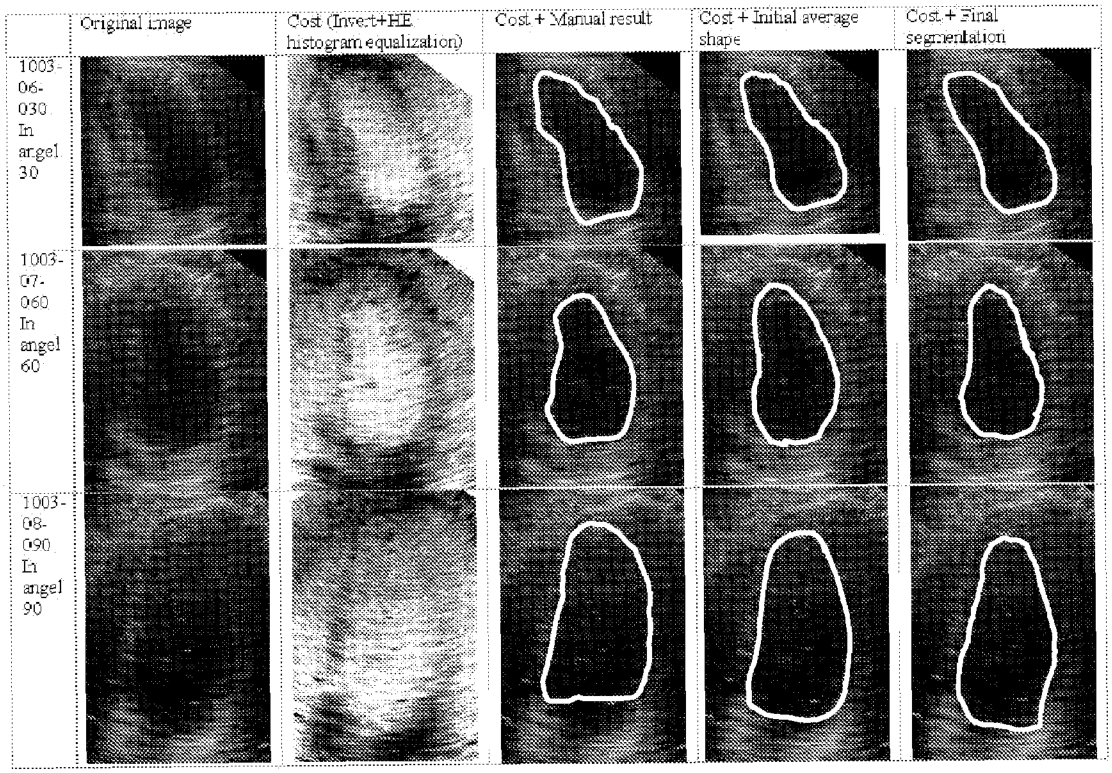
Figure 45:
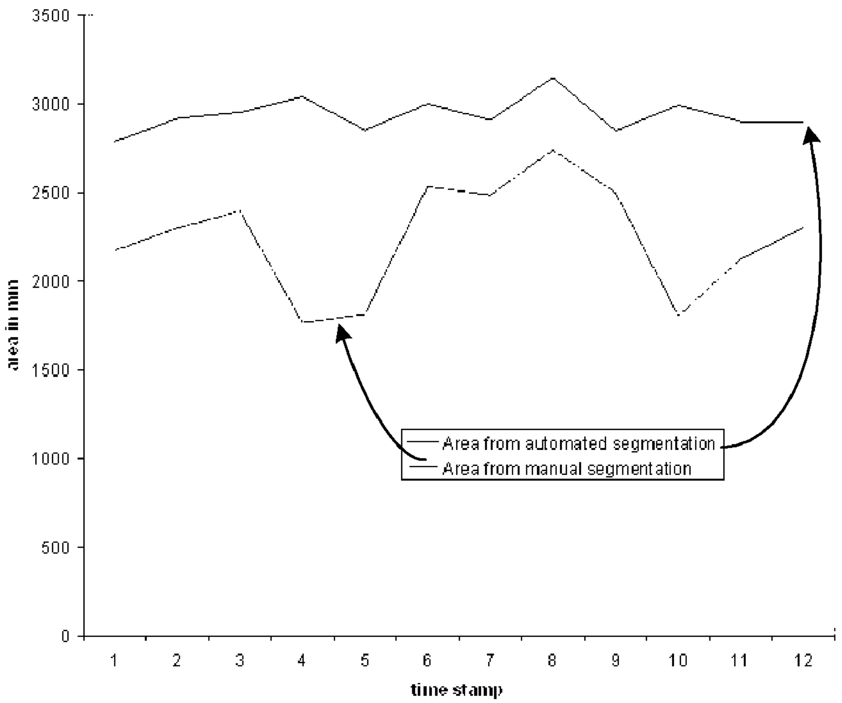
Figure 46:
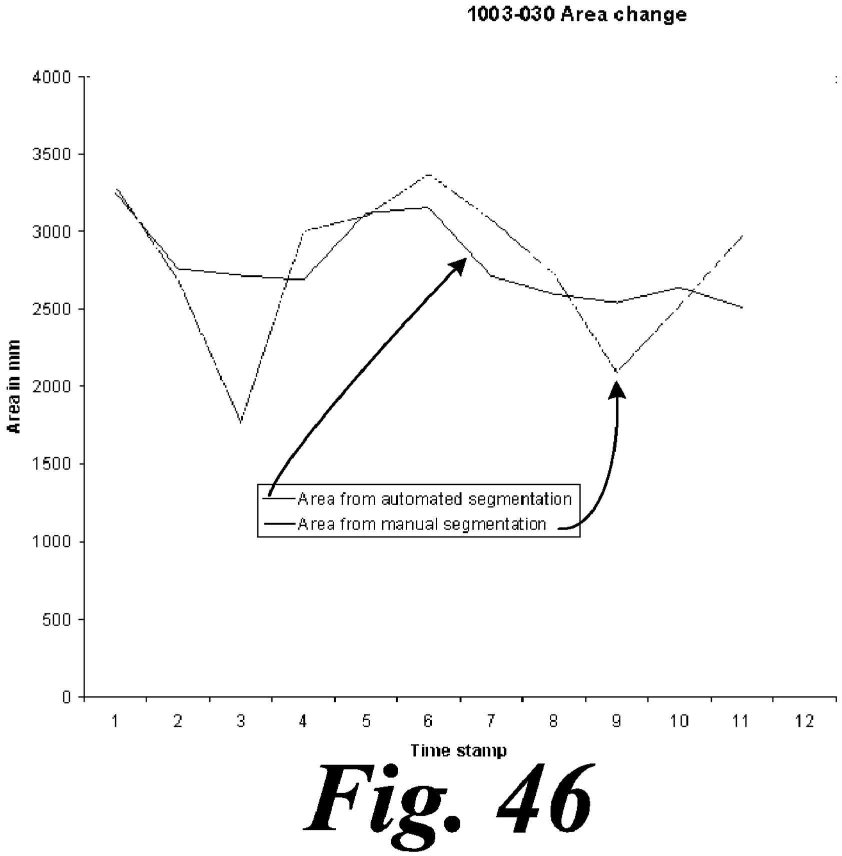
Figure 47:
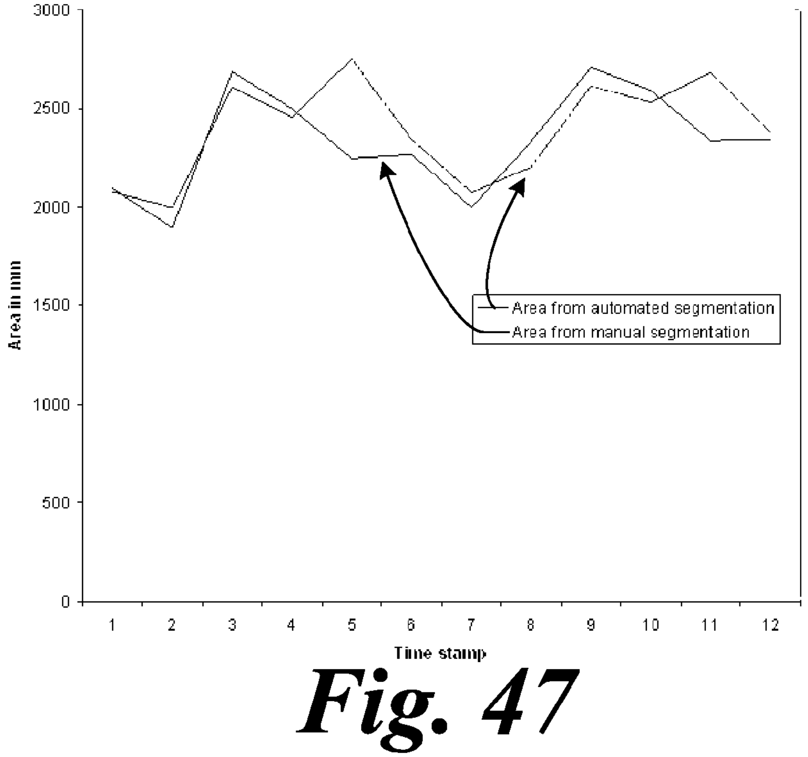
Figure 48:
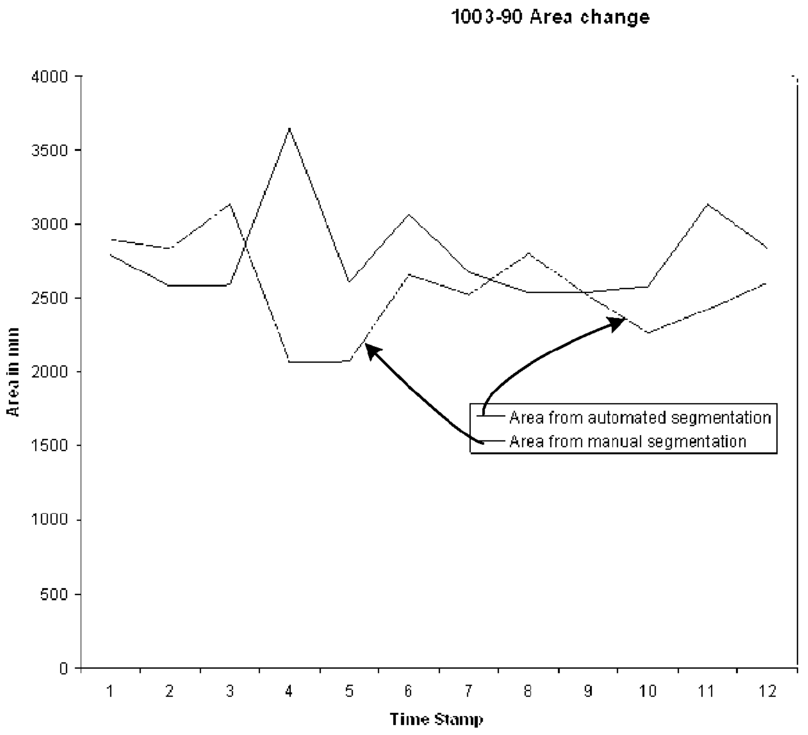
Figure 49:
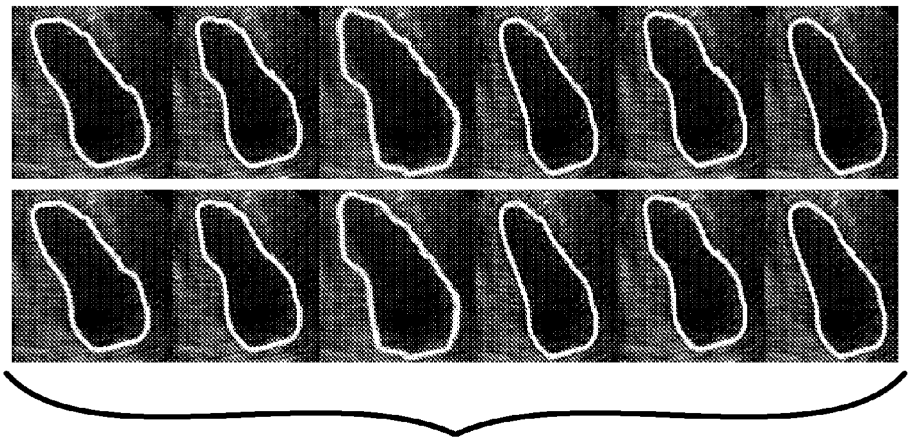
Figure 49:
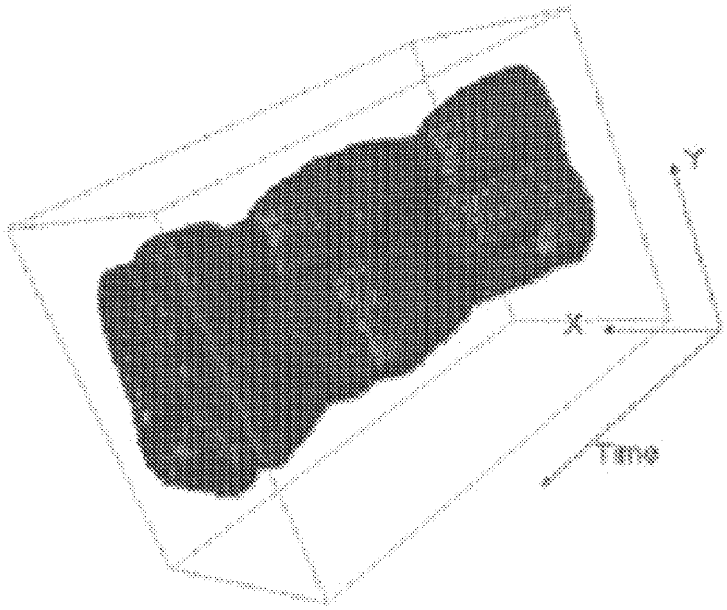
Figure 50:
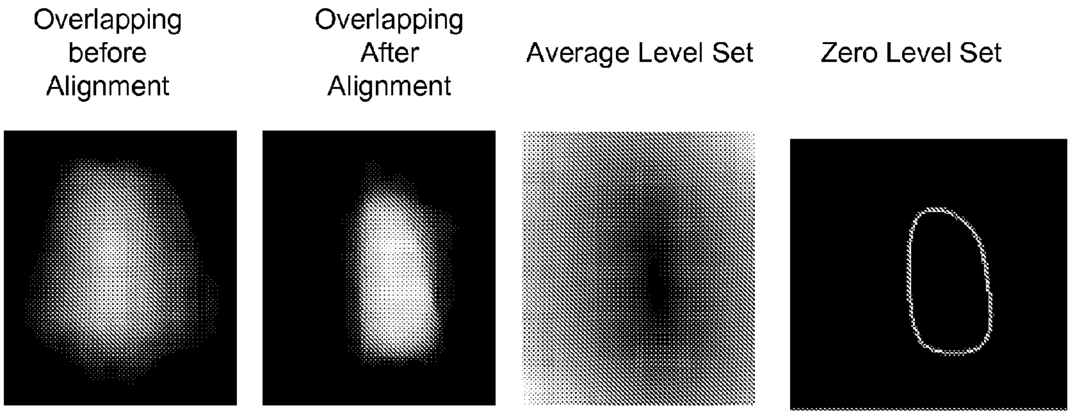
Figure 51:
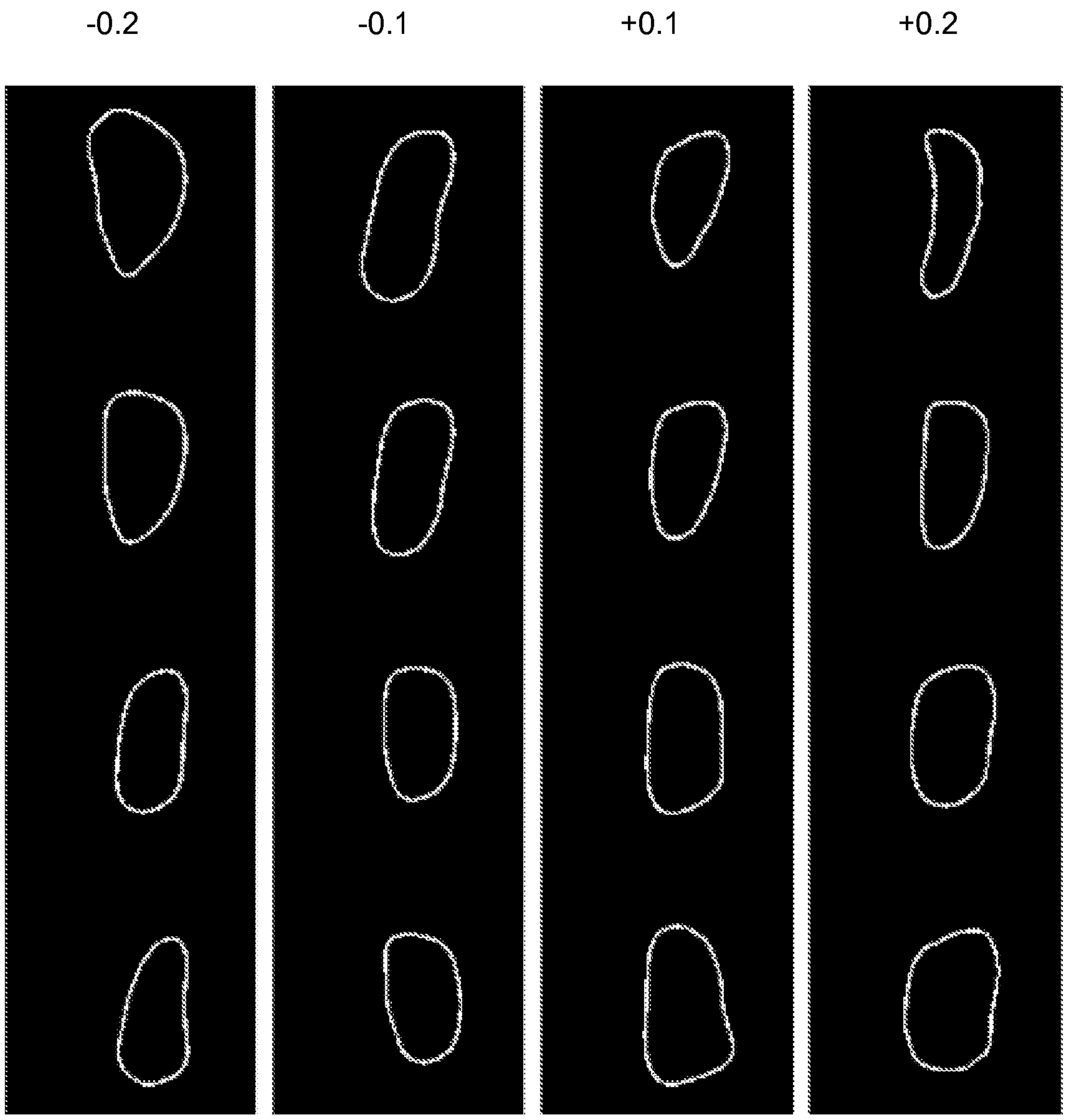
Figure 52:
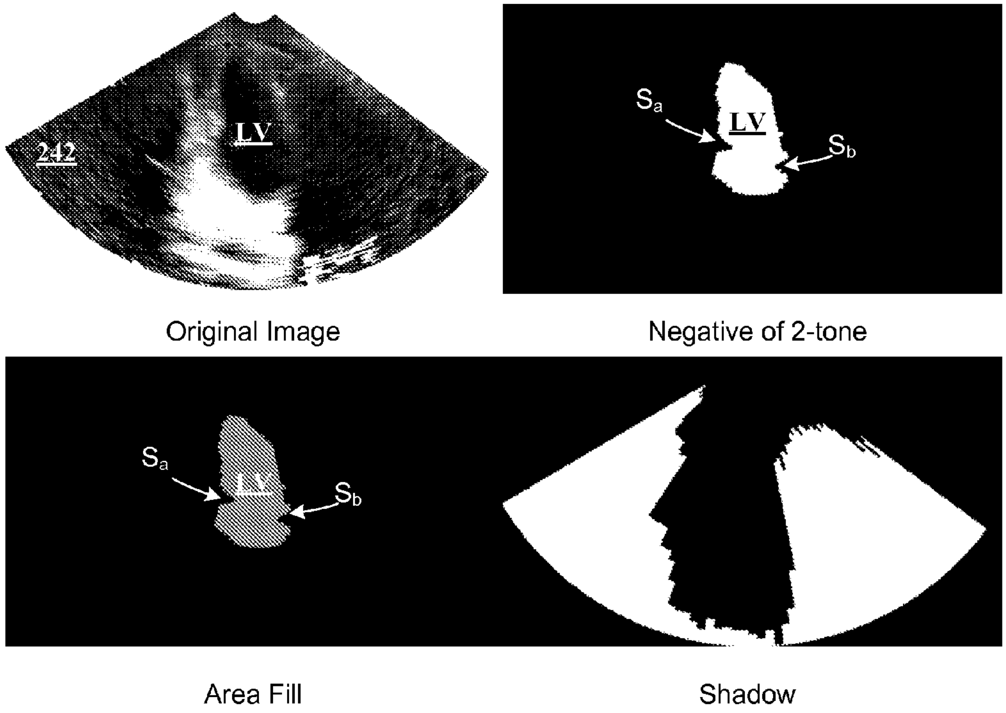
Figure 54:
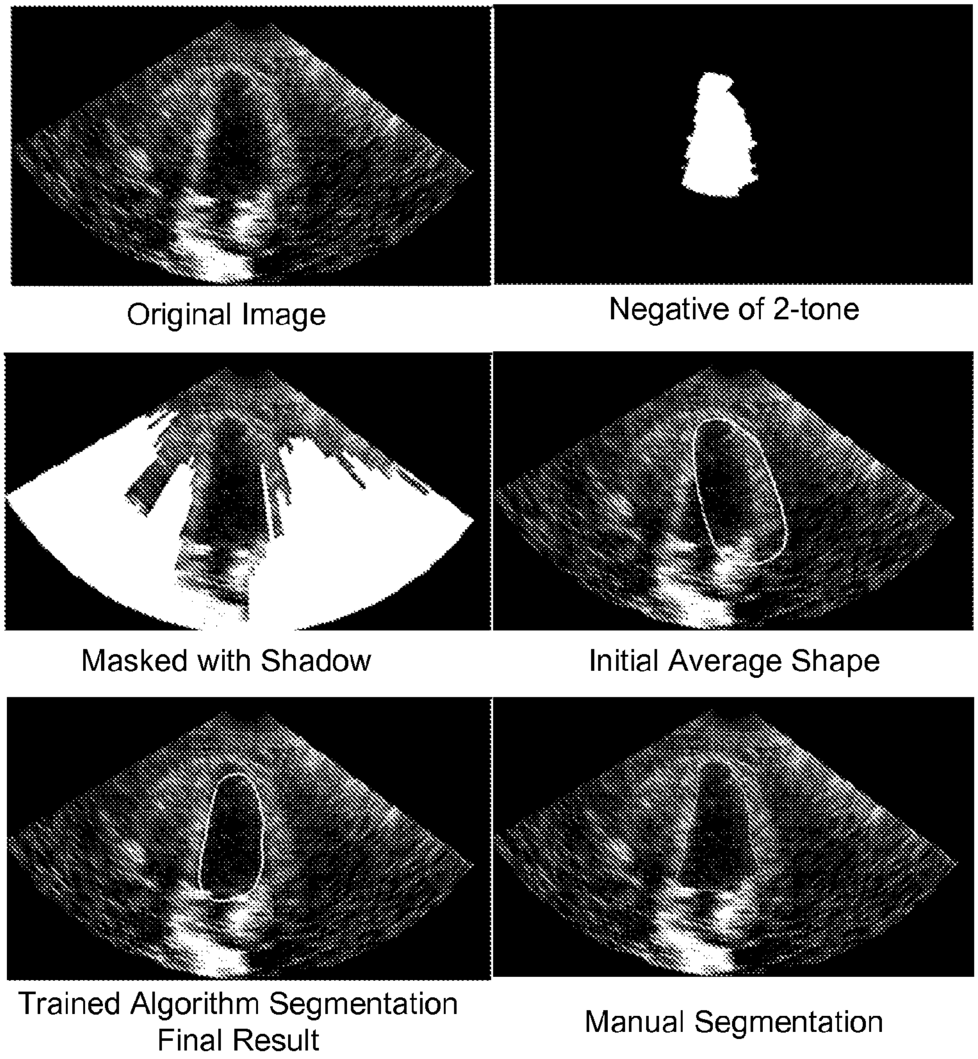
Figure 55:
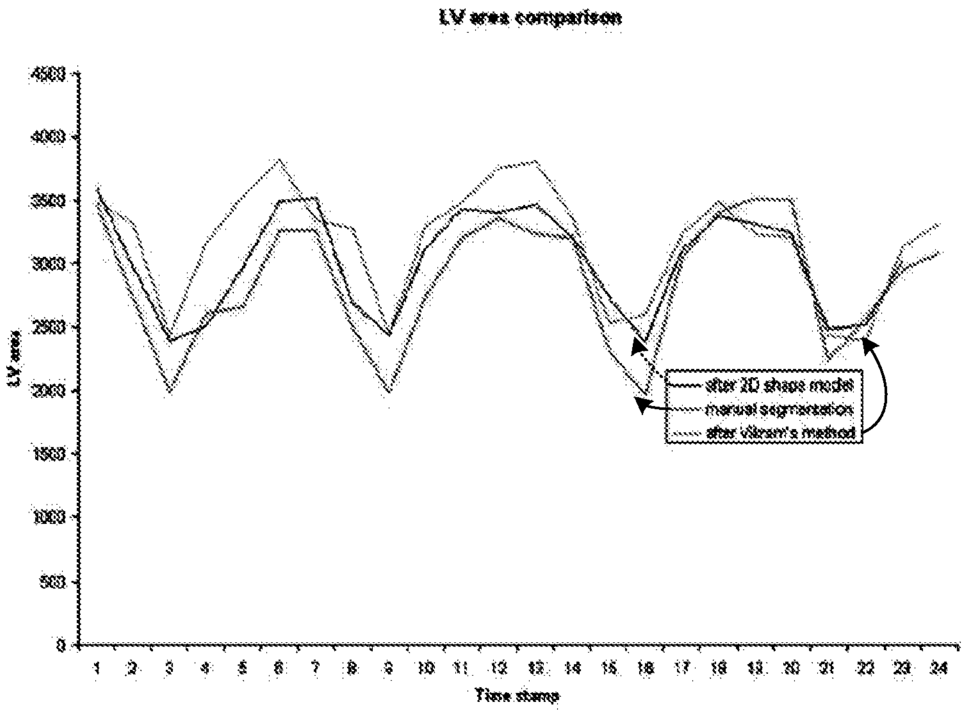
Figure 56:
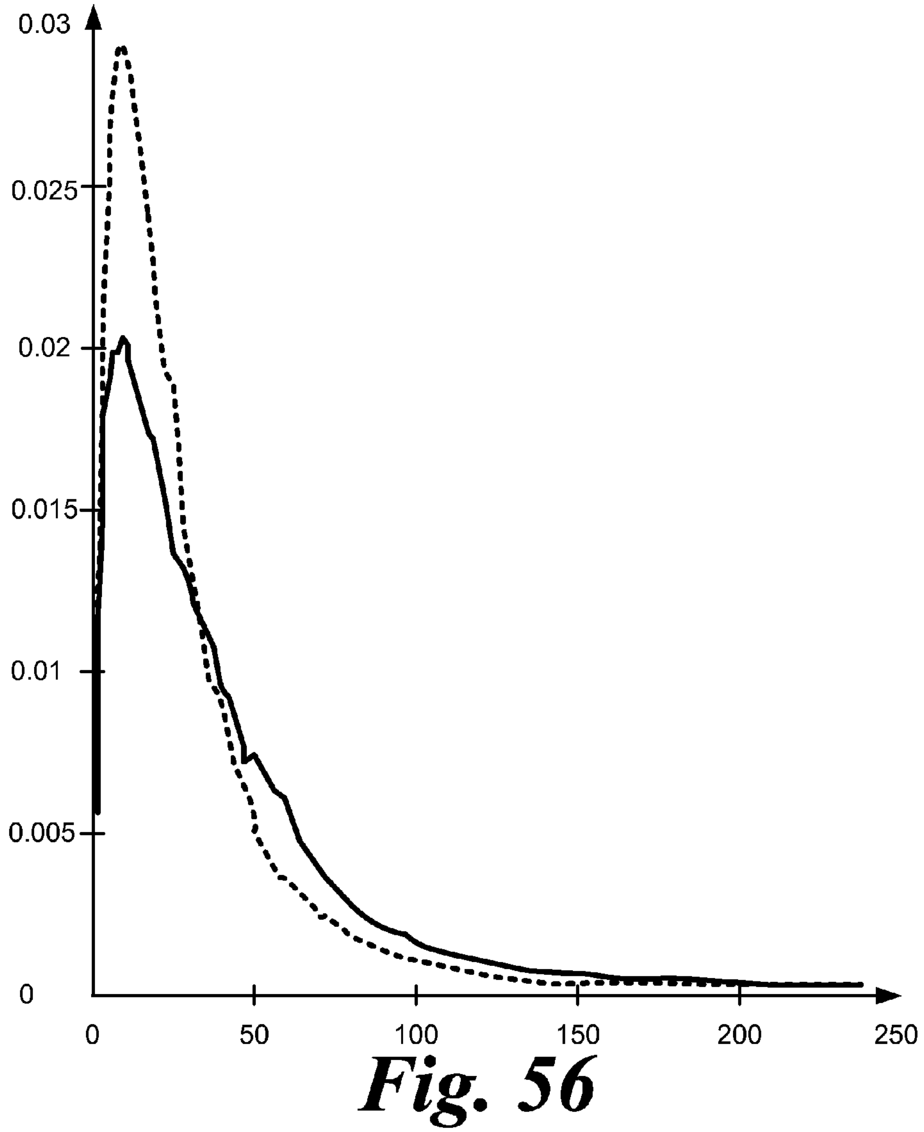
Figure 57:
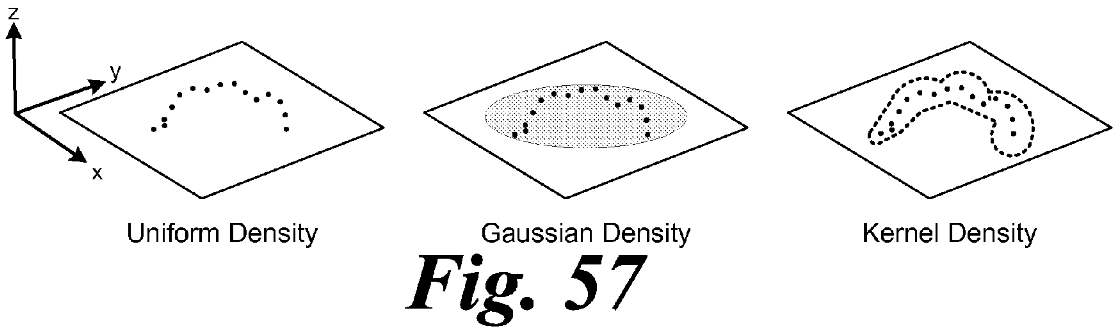
Figure 58:
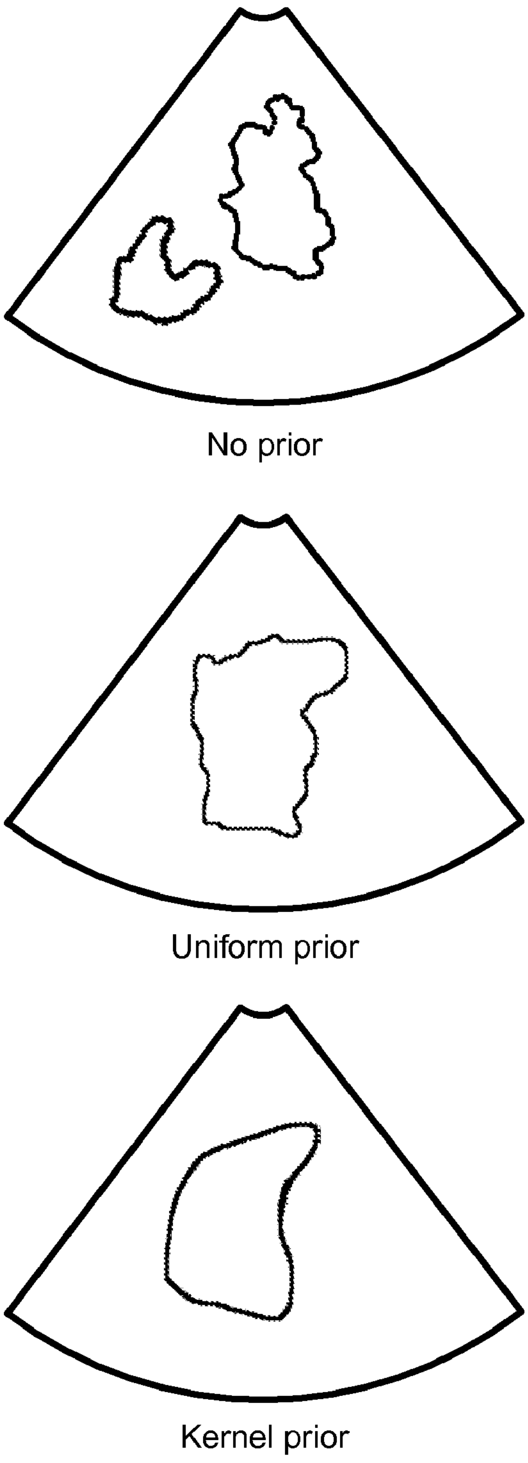
Figure 59:
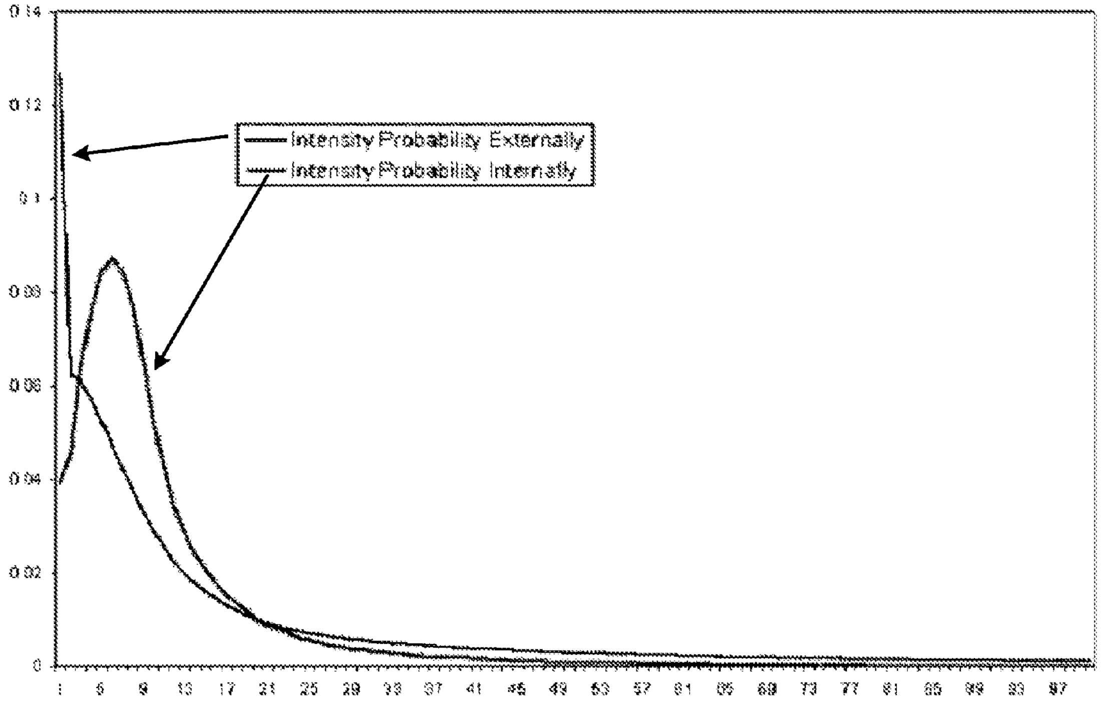
Figure 60:
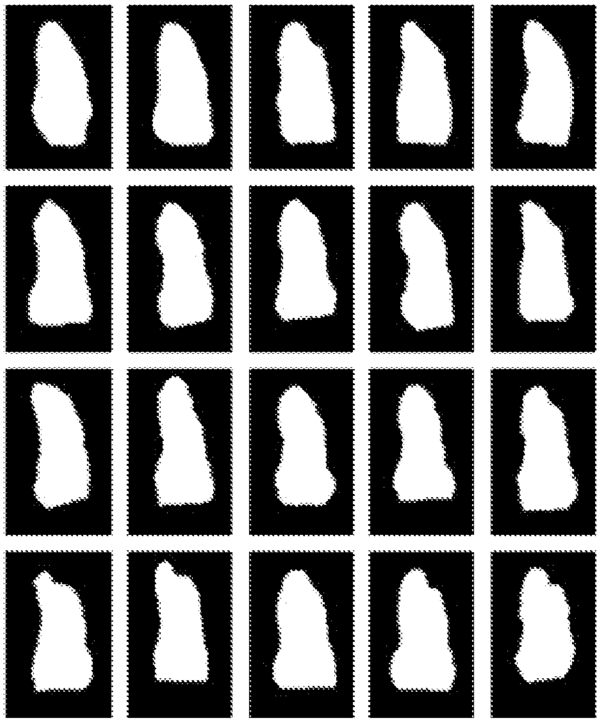
Figure 61:
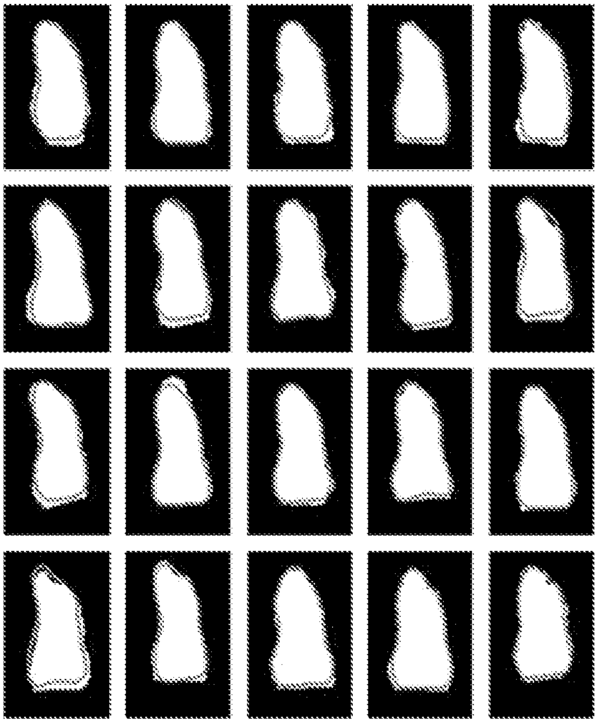
Figure 62:
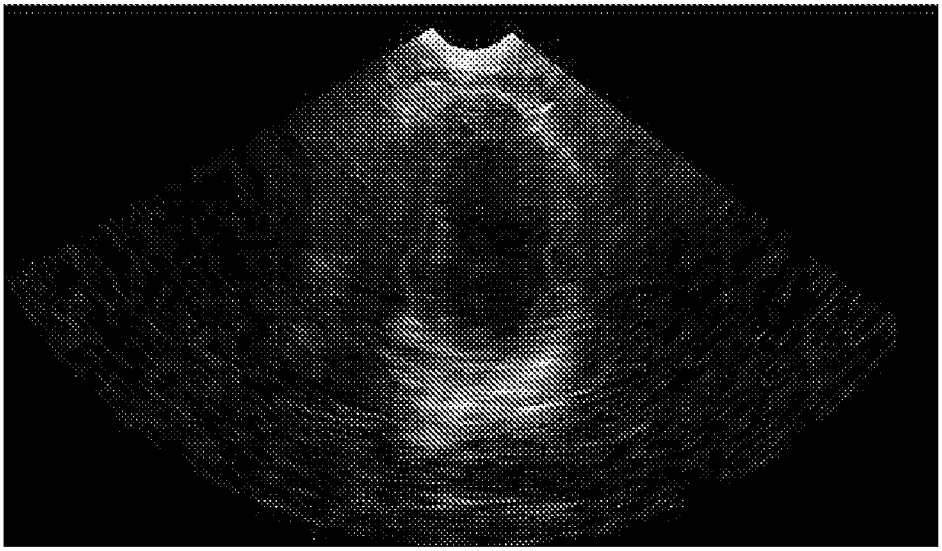
Figure 63:
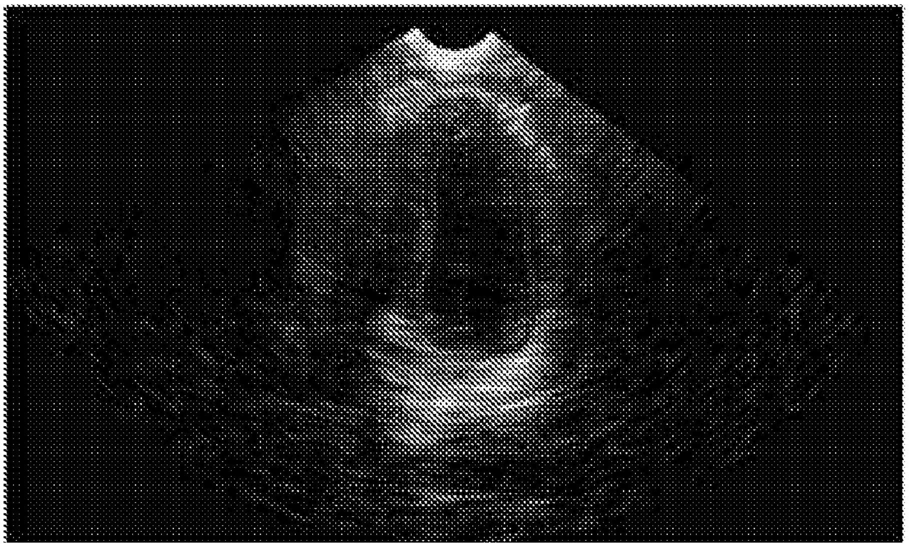

FIG. 30 illustrates a 12-panel outline of a left ventricle determined by an experienced sonographer overlapped before alignment by gradient descent;

FIG. 31 illustrates a 12-panel outline of a left ventricle determined by an experienced sonographer that are overlapped by gradient decent alignment between zero and level set outlines;

FIG. 32 illustrates the procedure for creation of a matrix S of a $N_1 \times N_2$ rectangular grid;

FIG. 33 is illustrates a training 12-panel eigenvector image set generated by distance mapping per process block 268 to extract mean eigen shapes;

FIG. 34 illustrates the 12-panel training eigenvector image set wherein ventricle boundary outlines are overlapped;

FIG. 35 illustrated the effects of using different W or k-eigenshapes to control the appearance and newly generated shapes;

FIG. 36 is an image of variation in 3D space affected by changes in 2D measurements over time;

FIG. 37 is a 7-panel phantom training image set compared with a 7-panel aligned set;

FIG. 38 is a phantom training set comprising variations in shapes;

FIG. 39 illustrates the restoration of properly segmented phantom measured structures from an initially compromised image using the aforementioned particular embodiments;

FIG. 40 schematically depicts a particular embodiment to determine shape segmentation of a ROI;

FIG. 41 illustrates an exemplary transthoracic apical view of two heart chambers;

FIG. 42 illustrates other exemplary transthoracic apical views as panel sets associated with different rotational scan plane angles;

FIG. 43 illustrates a left ventricle segmentation from different weight values w applied to a panel of eigenvector shapes;

FIG. 44 illustrates exemplary Left Ventricle segmentations using the trained level-set algorithms;

FIG. 45 is a plot of the level-set automated left ventricle area vs. the sonographer or manually measured area of angle 1003-000 from Table 3;

FIG. 46 is a plot of the level-set automated left ventricle area vs. the sonographer or manually measured area of angle 1003-030 from Table 4;

FIG. 47 is a plot of the level-set automated left ventricle area vs. the sonographer or manually measured area of angle 1003-060 from Table 5;

FIG. 48 is a plot of the level-set automated left ventricle area vs. the sonographer or manually measured area of angle 1003-090 from Table 6;

FIG. 49 illustrates the 3D-rendering of a portion of the Left Ventricle from 30 degree angular view presented from six scan planes obtained at systole and diastole;

FIG. 50 illustrates 4 eigenvector images undergoing different shape variations from a set of varying weight values w applied to the eigenvectors. A total of 16 shape variations are created with w values of −0.2, −0.1, +1, and +2;

FIG. 51 illustrates a series of Left Ventricle images undergoing shape alignment of the 16 eigenvector panel of FIG. 50 using the training sub-algorithm 264 of FIG. 23;

FIG. 52 presents an image result showing boundary artifacts of a left ventricle that arises by employing the estimate shadow regions algorithm 234 of FIG. 22;

FIG. 54 illustrates another panel of exemplary images showing the incremental effects of application of an alternate embodiment of the level-set sub-algorithm 260 of FIG. 23;

FIG. 54 illustrates another panel of exemplary images showing the incremental effects of application of level-set sub-algorithm 260 of FIG. 23;

FIG. 55 presents a graphic of Left Ventricle area determination as a function of 2D segmentation with time (2D+time) between systole and diastole by application of the particular and alternate embodiments of the level set algorithms of FIG. 23;

FIG. 56 illustrates cardiac ultrasound echo histograms of the left ventricle;

FIG. 57 depicts three panels in which schematic representations of a curved shaped eigenvector of a portion of a left ventricle is progressively detected when applied under uniform, Gaussian, and Kernel density pixel intensity distributions;

FIG. 58 depicts segmentation of the left ventricle arising from different a-priori model assumptions;

FIG. 59 is a histogram plot of 20 left ventricle scan planes to determine boundary intensity probability distributions employed for establishing segmentation within training data sets of the left ventricle;

FIG. 60 depicts a panel of aligned training shapes of the left ventricle from the data contained in Table 3;

FIG. 61 depicts the overlaying of the segmented left ventricle to the 20-image panel training set obtained by the application of level set algorithm generated eigen vectors of Table 6;

FIG. 62 depicts application of a non-model segmentation to an image of a subject's left ventricle; and FIG. 63 depicts application of a kernel-model segmentation to the same image of the subject's left ventricle.

DETAILED DESCRIPTION OF THE PREFERRED EMBODIMENTS

In general, systems and/or methods of image processing are described for automatically segmenting, i.e. automatically detecting the boundaries of shapes within a region of interest (ROI) of a single or series of images undergoing dynamic change. Particular and alternate embodiments provide for the subsequent measurement of areas and/or volumes of the automatically segmented shapes within the image ROI of a singular image multiple images of an image series undergoing dynamic change.

Methods include creating an image database having manually segmented shapes within the ROI of the images stored in the database, training computer readable image processing algorithms to duplicate or substantially reproduce the appearance of the manually segmented shapes, acquiring a non-database image, and segmenting shapes within the ROI of the non-database image by using the database-trained image processing algorithms.

In particular, as applied to sonographic systems, ultrasound systems and/or methods employing the acquisition of 3D transthoracic echocardiograms (TTE) are described to non-invasively measure heart chamber volumes and/or wall thicknesses between heart chambers during and/or between systole and/or diastole from 3D data sets acquired at systole and/or diastole. The measurements are obtained by using computer readable media employing image processing algorithms applied to the 3D data sets.

Moreover, these ultrasound systems and/or methods are further described to non-invasively measure heart chamber volumes, for example the left and/or right ventricle, and/or wall thicknesses and/or masses between heart chambers during and/or between systole and/or diastole from 3D data sets acquired at systole and/or diastole through the use of computer readable media having microprocessor executable image processing algorithms applied to the 3D data sets. The image processing algorithm utilizes trainable segmentation sub-algorithms. The changes in cardiac or heart chamber volumes may be expressed as a quotient of the difference between a given cardiac chamber volume occurring at systole and/or diastole and/or the volume of the given cardiac chamber at diastole. When the given cardiac chamber is the left ventricle, the changes in the left ventricle volumes may be expressed as an ejection fraction defined to be the quotient of the difference between the left ventricle volume occurring at systole and/or diastole and/or the volume of the left ventricle chamber at diastole.

The systems for cardiac imaging includes an ultrasound transceiver configured to sense the mitral valve of a heart by Doppler ultrasound, an electrocardiograph connected with a patient and synchronized with the transceiver to acquire ultrasound-based 3D data sets during systole and/or diastole at a transceiver location determined by Doppler ultrasound affected by the mitral valve, and a computer readable medium configurable to process ultrasound imaging information from the 3D data sets communicated from the transceiver and being synchronized with transceiver so that electrocardiograph connected with a patient that is configurable to determine an optimal location to acquire ultrasound echo 3D data sets of the heart during systole and/or diastole; utilize ultrasound transducers equipped with a microphone to computer readable mediums in signal communication with an electrocardiograph.

The image processing algorithms delineate the outer and/or inner walls of the heart chambers within the heart and/or determine the actual surface area, S, of a given chamber using a modification of the level set algorithms, as described below, and utilized from the VTK Library maintained by Kitware, Inc. (Clifton Park, N.Y., USA), incorporated by reference herein. The selected heart chamber, the thickness t of wall between the selected heart chamber and adjacent chamber, is then calculated as the distance between the outer and the inner surfaces of selected and adjacent chambers. Finally, as shown in equation E1, the inter-chamber wall mass (ICWM) is estimated as the product of the surface area, the interchamber wall thickness (ICWT) and cardiac muscle specific gravity, ρ:

$$ICWM = S \times ICWT \times \rho. \quad \text{E1}$$

One benefit of the embodiments of the present invention is that it produces more accurate and consistent estimates of selected heart chamber volumes and/or inter-chamber wall masses. The reasons for higher accuracy and consistency include:

1. The use of three-dimensional data instead of two-dimensional data to calculate the surface area and/or thickness. In another embodiment, the outer anterior wall of the heart chamber is delineated to enable the calculation of the inter-chamber wall thickness (ICWT);
2. The use of the trainable segmentation sub-algorithms in obtaining measured surface area instead of using surface area based upon a fixed model; and
3. The automatic and consistent measurement of the ICWT.

Additional benefits conferred by the embodiments also include its non-invasiveness and its ease of use in the ICWT is measured over a range of chamber volumes, thereby eliminating the need to invasively probe a patient.

FIGS. 1A-D depicts a partial schematic and partial isometric view of a transceiver, a scan cone array of scan planes, and a scan plane of the array.

Figures 1A, 1B, 1C, 1D:
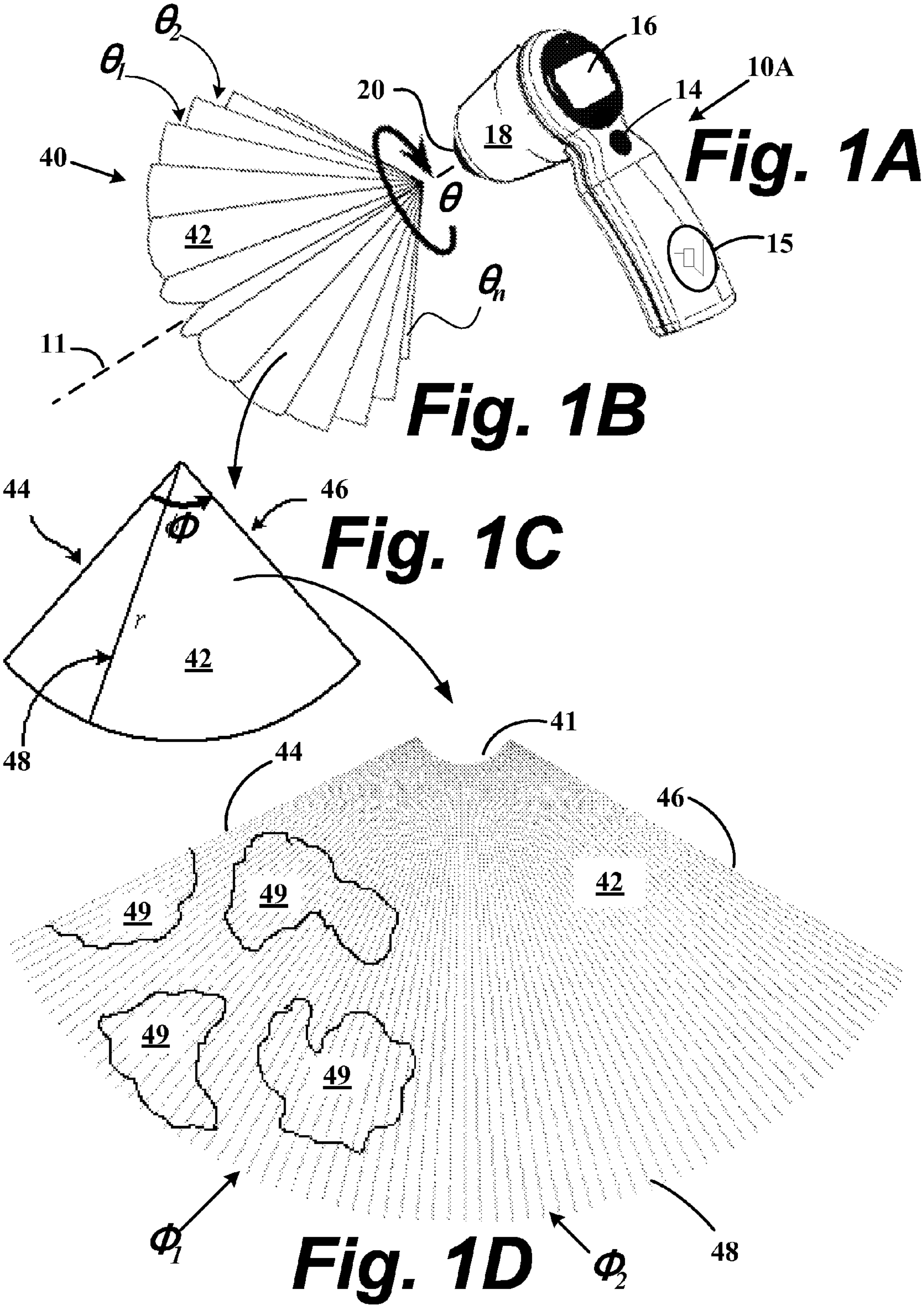
FIGS. 1A-D depicts a partial schematic and a partial isometric view of a transceiver, a scan cone comprising a rotational array of scan planes, and a scan plane of the array.

FIG. 1A depicts a transceiver 10A having an ultrasound transducer housing 18 and a transceiver dome 20 from which ultrasound energy emanates to probe a patient or subject upon pressing the button 14. Doppler or image information from ultrasound echoes returning from the probed region is presented on the display 16. The information may be alphanumeric, pictorial, and describe positional locations of a targeted organ, such as the heart, or other chamber-containing ROI. A speaker 15 conveys audible sound indicating the flow of blood between and/or from heart chambers. Characteristic sounds indicating blow flow through and/or from the mitral valve are used to reposition the transceiver 10A for the centered acquisition of image 3D data sets obtained during systole and/or diastole.

FIG. 1B is a graphical representation of a plurality of scan planes 42 that contain the probing ultrasound. The plurality of scan planes 42 defines a scan cone 40 in the form of a three-dimensional (3D) array having a substantially conical shape that projects outwardly from the dome 20 of the transceivers 10A.

The plurality of scan planes 42 are oriented about an axis 11 extending through the transceivers 10A. One or more, or alternately each of the scan planes 42 are positioned about the axis 11, which may be positioned at a predetermined angular position θ. The scan planes 42 are mutually spaced apart by angles $\theta_1$ and $\theta_2$ whose angular value may vary. That is, although the angles $\theta_1$ and $\theta_2$ to $\theta_n$ are depicted as approximately equal, the θ angles may have different values. Other scan cone configurations are possible. For example, a wedge-shaped scan cone, or other similar shapes may be generated by the transceiver 10A.

FIG. 1C is a graphical representation of a scan plane 42. The scan plane 42 includes the peripheral scan lines 44 and 46, and an internal scan line 48 having a length r that extends outwardly from the transceivers 10A and between the scan lines 44 and 46. Thus, a selected point along the peripheral scan lines 44 and 46 and the internal scan line 48 may be defined with reference to the distance r and angular coordinate values ϕ and θ. The length r preferably extends to approximately 18 to 20 centimeters (cm), although other lengths are possible. Particular embodiments include approximately seventy-seven scan lines 48 that extend outwardly from the dome 20, although any number of scan lines may be used.

FIG. 1D a graphical representation of a plurality of scan lines 48 emanating from the ultrasound transceiver forming a single scan plane 42 extending through a cross-section of portions of an internal bodily organ. The scan plane 42 is fan-shaped, bounded by peripheral scan lines 44 and 46, and has a semi-circular dome cutout 41. The number and/or location of the internal scan lines emanating from the transceivers 10A within a given scan plane 42 may be distributed at different positional coordinates about the axis line 11 to sufficiently visualize structures or images within the scan plane 42. As shown, four portions of an off-centered region-of-interest (ROI) are exhibited as irregular regions 49 of the internal organ. Three portions are viewable within the scan plane 42 in totality, and one is truncated by the peripheral scan line 44.

As described above, the angular movement of the transducer may be mechanically effected and/or it may be electronically or otherwise generated. In either case, the number of lines 48 and/or the length of the lines may vary, so that the tilt angle ϕ (FIG. 1C) sweeps through angles approximately between −60° and +60° for a total arc of approximately 120°. In one particular embodiment, the transceiver 10A is configured to generate approximately about seventy-seven scan lines between the first limiting scan line 44 and a second limiting scan line 46. In another particular embodiment, each of the scan lines has a length of approximately about 18 to 20 centimeters (cm). The angular separation between adjacent scan lines 48 (FIG. 1B) may be uniform or non-uniform. For example, and in another particular embodiment, the angular separation $\phi_1$ and $\phi_2$ to $\phi_n$ (as shown in FIG. 1B) may be about 1.5°. Alternately, and in another particular embodiment, the angular separation $\phi_1$, $\phi_2$, $\phi_n$ may be a sequence wherein adjacent angles are ordered to include angles of 1.5°, 6.8°, 15.5°, 7.2°, and so on, where a 1.5° separation is between a first scan line and a second scan line, a 6.8° separation is between the second scan line and a third scan line, a 15.5° separation is between the third scan line and a fourth scan line, a 7.2° separation is between the fourth scan line and a fifth scan line, and so on. The angular separation between adjacent scan lines may also be a combination of uniform and non-uniform angular spacings, for example, a sequence of angles may be ordered to include 1.5°, 1.5°, 1.5°, 7.2°, 14.3°, 20.2°, 8.0°, 8.0°, 8.0°, 4.3°, 7.8°, and so on.

Figure 2:
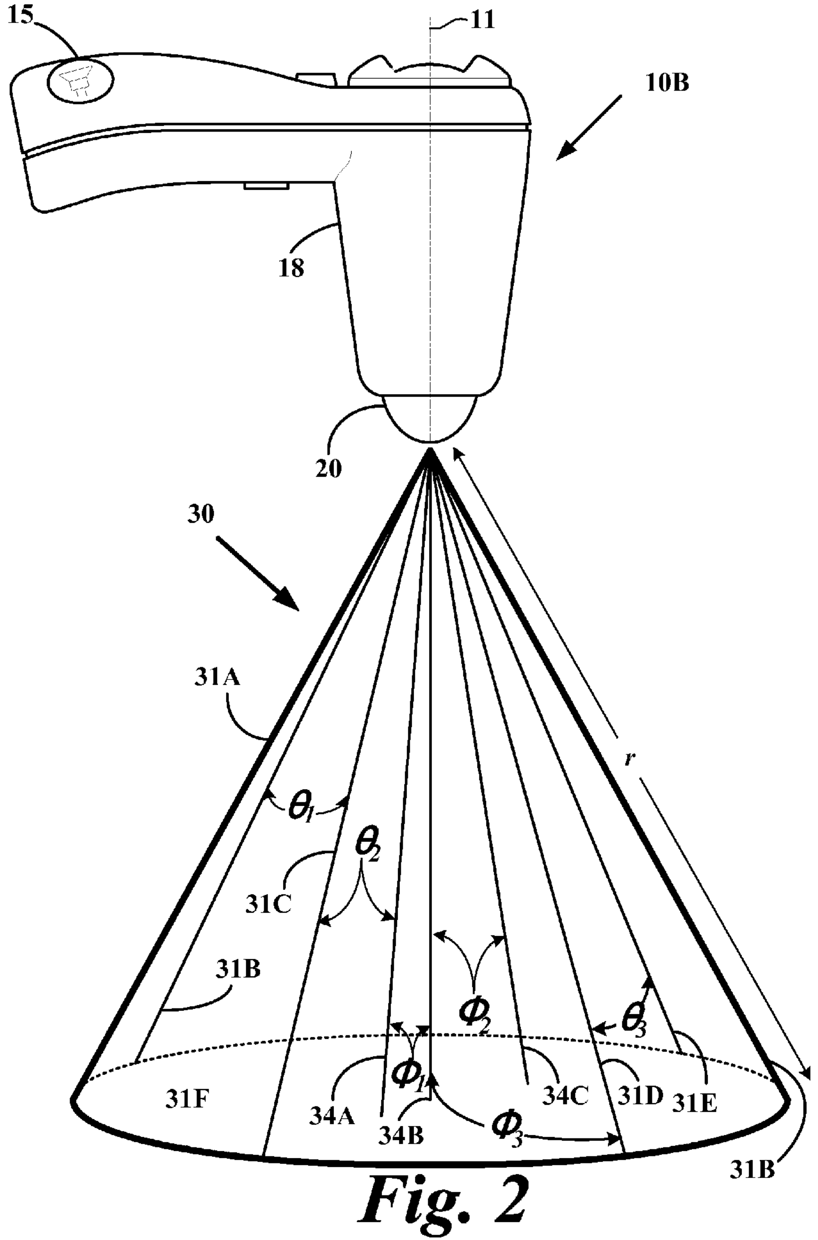
FIG. 2 depicts a partial schematic and partial isometric and side view of a transceiver, and a scan cone array comprised of 3D-distributed scan lines.

FIG. 2 depicts a partial schematic and partial isometric and side view of a transceiver 10B, and a scan cone array 30 comprised of 3D-distributed scan lines. Each of the scan lines have a length r that projects outwardly from the transceiver 10B. As illustrated the transceiver 10B emits 3D-distributed scan lines within the scan cone 30 that are one-dimensional ultrasound A-lines. Taken as an aggregate, these 3D-distributed A-lines define the conical shape of the scan cone 30. The ultrasound scan cone 30 extends outwardly from the dome 20 of the transceiver 10B and centered about the axis line 11 (FIG. 1B). The 3D-distributed scan lines of the scan cone 30 include a plurality of internal and peripheral scan lines that are distributed within a volume defined by a perimeter of the scan cone 30. Accordingly, the peripheral scan lines 31A-31F define an outer surface of the scan cone 30, while the internal scan lines 34A-34C are distributed between the respective peripheral scan lines 31A-31F. Scan line 34B is generally collinear with the axis 11, and the scan cone 30 is generally and coaxially centered on the axis line 11.

The locations of the internal and/or peripheral scan lines may be further defined by an angular spacing from the center scan line 34B and between internal and/or peripheral scan lines. The angular spacing between scan line 34B and peripheral or internal scan lines are designated by angle Φ and angular spacings between internal or peripheral scan lines are designated by angle Ø. The angles $\Phi_1$, $\Phi_2$, and $\Phi_3$ respectively define the angular spacings from scan line 34B to scan lines 34A, 34C, and 31D. Similarly, angles $Ø_1$, $Ø_2$, and $Ø_3$ respectively define the angular spacing between scan line 31B and 31C, 31C and 34A, and 31D and 31E.

With continued reference to FIG. 2, the plurality of peripheral scan lines 31A-E and the plurality of internal scan lines 34A-D are three dimensionally distributed A-lines (scan lines) that are not necessarily confined within a scan plane, but instead may sweep throughout the internal regions and/or along the periphery of the scan cone 30. Thus, a given point within the scan cone 30 may be identified by the coordinates r, Φ, and Ø whose values generally vary. The number and/or location of the internal scan lines 34A-D emanating from the transceiver 10B may thus be distributed within the scan cone 30 at different positional coordinates to sufficiently visualize structures or images within a region of interest (ROI) in a patient. The angular movement of the ultrasound transducer within the transceiver 10B may be mechanically effected, and/or it may be electronically generated. In any case, the number of lines and/or the length of the lines may be uniform or otherwise vary, so that angle Φ may sweep through angles approximately between −60° between scan line 34B and 31A, and +60° between scan line 34B and 31B. Thus, the angle Φ may include a total arc of approximately 120°. In one embodiment, the transceiver 10B is configured to generate a plurality of 3D-distributed scan lines within the scan cone 30 having a length r of approximately 18 to 20 centimeters (cm). Repositioning of the transceiver 10B to acquire centered cardiac images derived from 3D data sets obtained at systole and/or diastole may also be affected by the audible sound of mitral valve activity caused by Doppler shifting of blood flowing through the mitral valve that emanates from the speaker 15.

Figure 3:
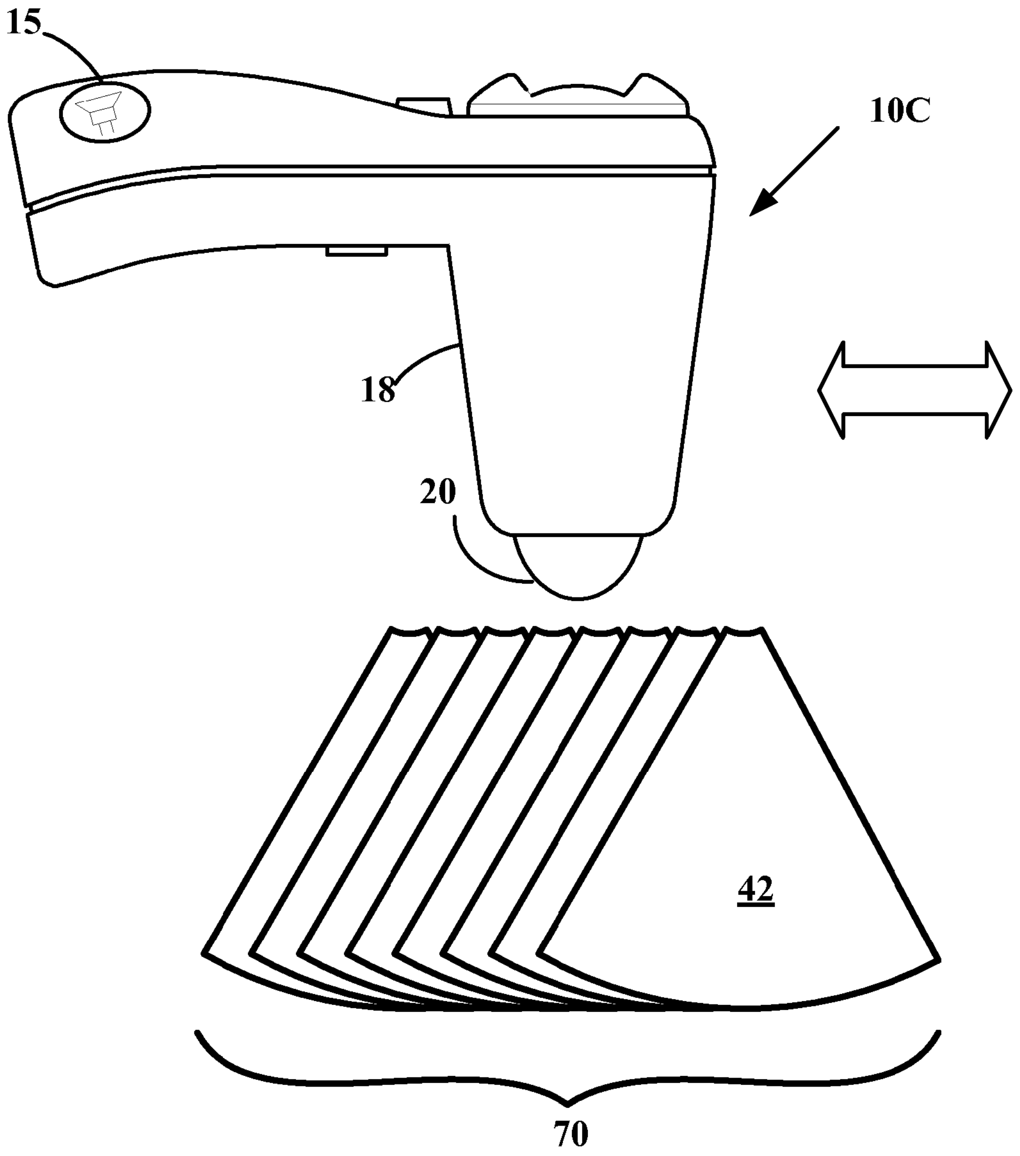
FIG. 3 depicts a transceiver 10C acquiring a translation array 70 of scanplanes 42.

FIG. 3 depicts a transceiver 10C acquiring a translation array 70 of scanplanes 42. The translation array 70 is acquired by successive, linear freehand movements in the direction of the double headed arrow. Sound emanating from the speaker 15 helps determine the optimal translation position arising from mitral valve blood flow Doppler shifting for acquisition of 3D image data sets during systole and/or diastole.

Figure 4:
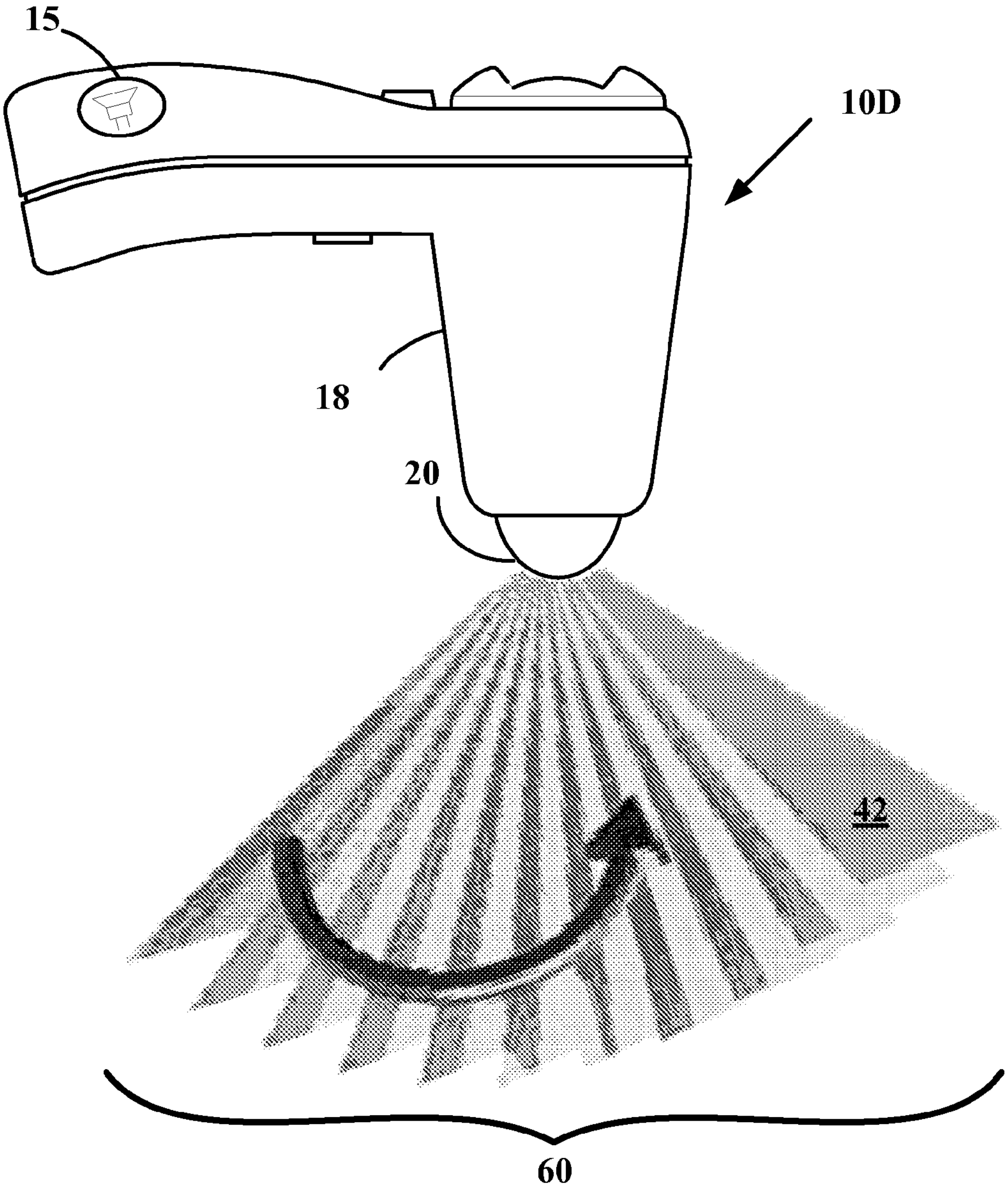
FIG. 4 depicts a transceiver 10D acquiring a fan array 60 of scanplanes 42.
Figure 5:
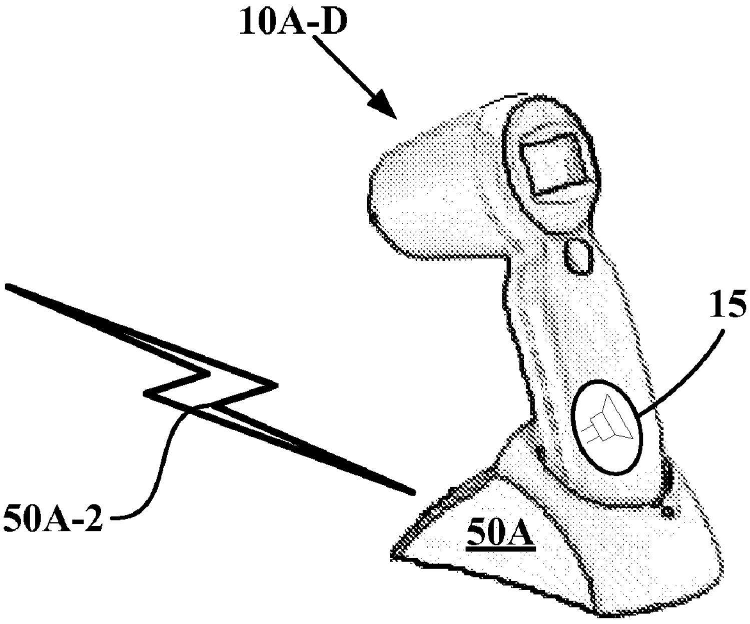
FIG. 5 depicts the transceivers 10A-D (FIG. 1) removably positioned in a communications cradle 50A that is operable to communicate the data wirelessly uploaded to the computer or other microprocessor device (not shown)

FIG. 4 depicts a transceiver 10D acquiring a fan array 60 of scanplanes 42. The fan array 60 is acquired by successive, incremental pivoting movement of the ultrasound transducer along the direction of the curved arrow. Sound emanating from the speaker 15 helps determine the optimal translation position arising from mitral valve blood flow Doppler shifting for acquisition of 3D image data sets during systole and/or diastole.

Figure 6:
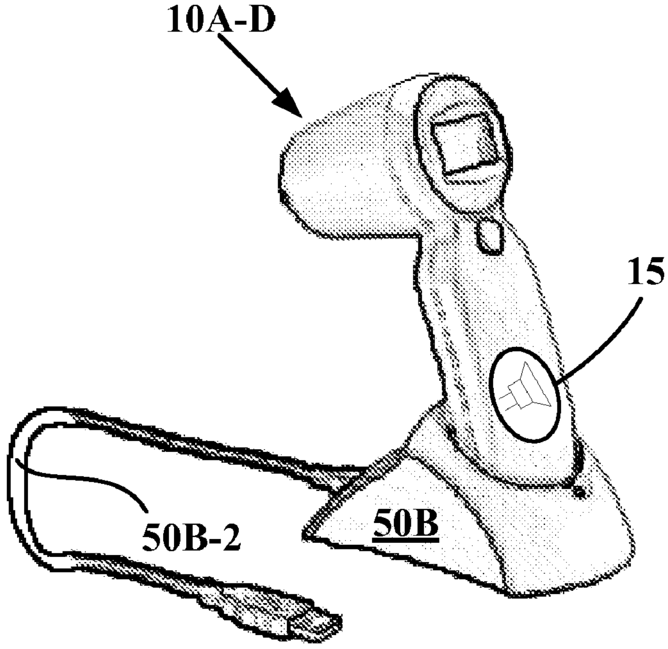
FIG. 6 depicts the transceivers 10A-D removably positioned in a communications cradle to communicate imaging data by wire connections uploaded to the computer or other microprocessor device (not shown)

FIG. 6 depicts the transceivers 10A-D removably positioned in a communications cradle to communicate imaging data by wire connections uploaded to the computer or other microprocessor device (not shown). The data is uploaded securely to the computer or to a server via the computer where it is processed by a bladder weight estimation algorithm that will be described in greater detail below. The transceiver 10B may be similarly housed in the cradle 50A. In this wireless embodiment, the cradle 50A has circuitry that receives and converts the informational content of the scan cone 40 or scan cone 30 to a wireless signal 50A-2.

FIG. 6 depicts the transceivers 10A-D removably positioned in a communications cradle 50B where the data is uploaded by an electrical connection 50B-2 to the computer or other microprocessor device (not shown). The data is uploaded securely to the computer or to a server via the computer where it is processed by the bladder weight estimation algorithm. In this embodiment, the cradle 50B has circuitry that receives and converts the informational content of the scan cones 30/40, translation array 70, scanplane fan 60, scanplane to a non-wireless signal that is conveyed in conduit 50B-2 capable of transmitting electrical, light, or sound-based signals. A particular electrical embodiment of conduit 50B-2 may include a universal serial bus (USB) in signal communication with a microprocessor-based device.

Figure 7A:
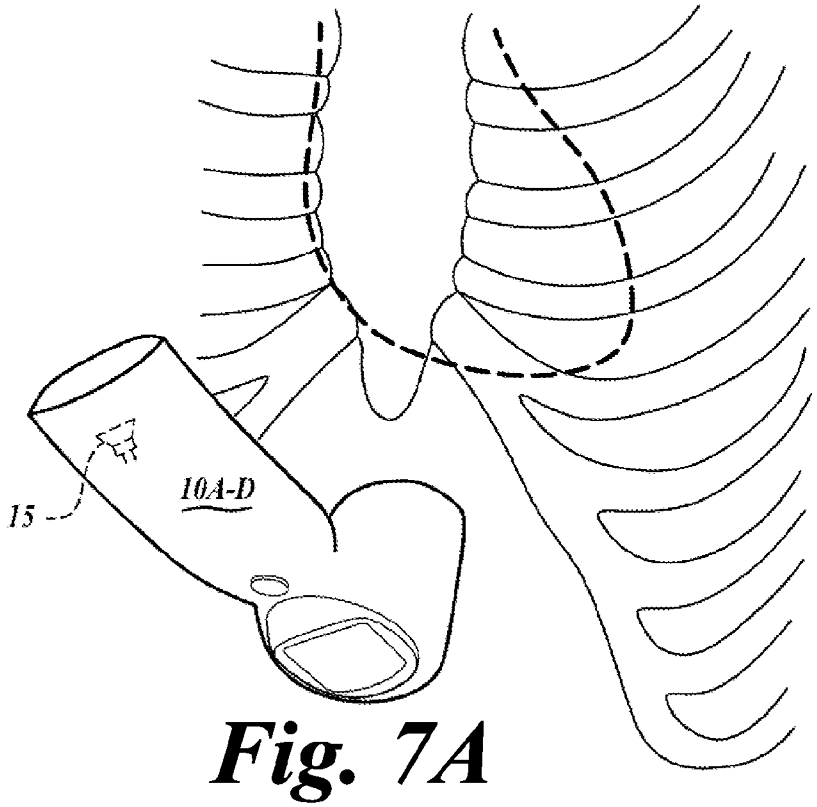
FIG. 7A depicts an image showing the chest area of a patient 68 being scanned by a transceivers 10A-D at a first freehand position and the data being wirelessly uploaded to a personal computer during initial targeting of a cardiac region of interest (ROI)

FIG. 7A depicts an image showing the chest area of a patient 68 being scanned by a transceivers 10A-D and the data being wirelessly uploaded to a personal computer during initial targeting of a region of interest (ROI) of the heart (dashed lines) during an initial targeting or aiming phase. The heart ROI is targeted underneath the sternum between the thoracic rib cages at a first freehand position. Confirmation of target positioning is determined by the characteristic Doppler sounds emanating from the speaker 15.

Figure 7B:
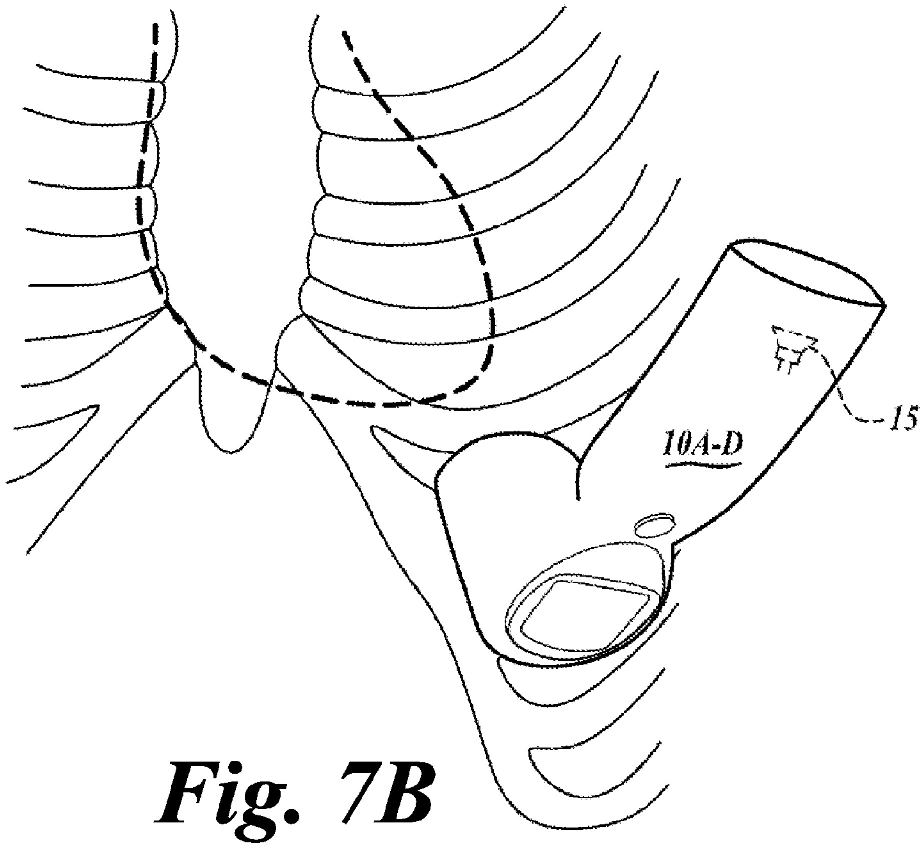
FIG. 7B depicts an image showing the chest area of the patient 68 being scanned by a transceiver 10A-D at a second freehand position where the transceiver 10A-D is aimed toward the cardiac ROI between ribs of the left side of the thoracic cavity.

FIG. 7B depicts an image showing the chest area of the patient 68 being scanned by a transceiver 10A-D at a second freehand position where the transceiver 10A-E is aimed toward the cardiac ROI between ribs of the left side of the thoracic cavity. Similarly, confirmation of target positioning is determined by the characteristic Doppler sounds emanating from the speaker 15.

Figure 8:
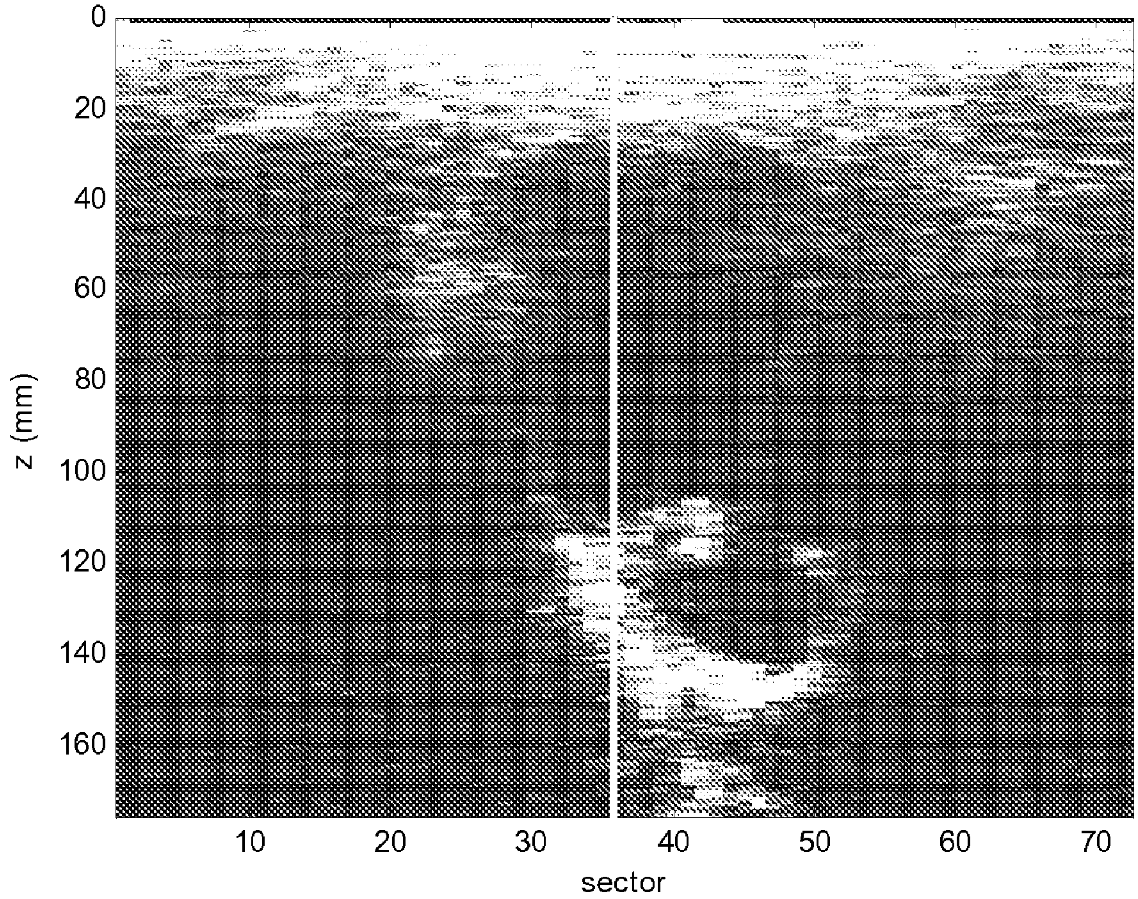
FIG. 8 depicts the centering of the heart for later acquisition of 3D image sets based upon the placement of the mitral valve near the image center as determined by the characteristic Doppler sounds from the speaker 15 of transceivers 10A-D.

FIG. 8 depicts the centering of the heart for later acquisition of 3D image sets based upon the placement of the mitral valve near the image center as determined by the characteristic Doppler sounds from the speaker 15 of transceivers 10A-D. A white broadside scan line on the pre-scan-converted image is visible. Along this line, the narrow band signals are transmitted and the Doppler signals are acquired.

When the ultrasound scanning device is in an aiming mode, the transducer is fixed at the broadside scan line position. The ultrasound scanning device repeats transmitting and receiving sound waves alternatively with the pulse repetition frequency, prf. The transmitting wave is narrow band signal which has large number of pulses. The receiving depth is gated between 8 cm and 15 cm to avoid the ultrasound scanning device's wall detecting of the motion artifacts from hands or organ (heartbeat).

Figure 9:
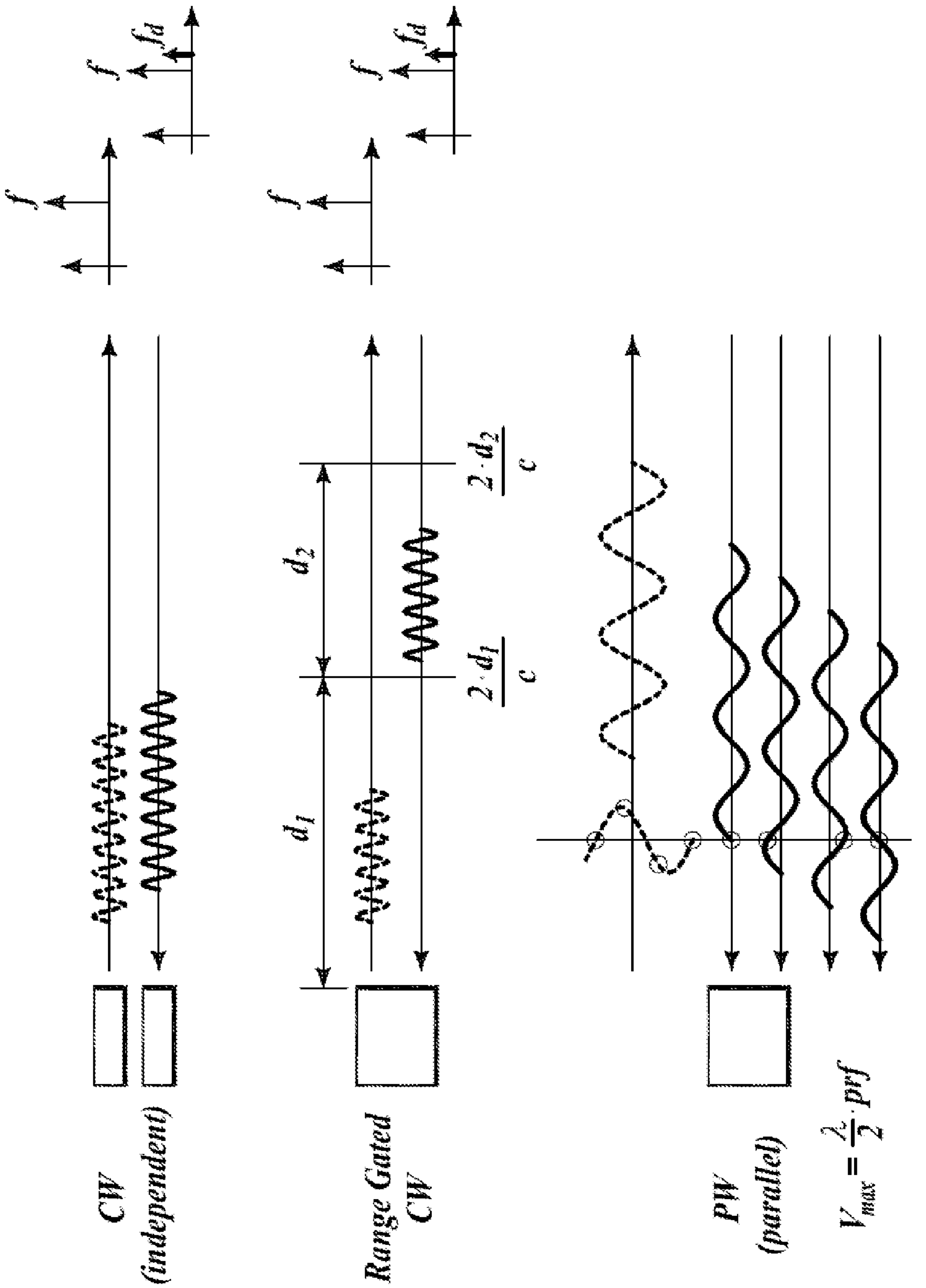
FIG. 9 is a schematic depiction of the Doppler operation of the transceivers 10A-D.

FIG. 9 is a schematic depiction of the Doppler operation of the transceivers 10A-D described in terms of independent, range-gated, and parallel. Waves are transmitting to tissue and reflected waves are returning from tissue. The frequency of the mitral valve opening is the same as the heart bit which is 1 Hz (normally 70 times per minute). The speed of open/close motion which will relate to the Doppler frequency is approximately 10 cm/s (maximum of 50 cm/s). The interval between acquired RFUS lines represents the prf. For the parallel or pulse wave (PW) case, the relationship between the maximum mitral valve velocity, $V_{max}$, and prf not to have aliasing is $V_{max}=(\lambda/2)\cdot prf$. Therefore, in order to detect the maximum velocity 50 cm/s using 3.7 MHz transmit frequency while avoiding aliasing, at least 2.5 KHz prf may be used.

The CW (Continuous Wave-independent) Doppler as shown in FIG. 9 can estimate the velocities independently, i.e., each scanline has its Doppler frequency shift information. CW does not include information about the depth where the motion occurs. The range gated CW Doppler can limit the range to some extent but still should keep the number of pulses to be narrow band signal to separate the Doppler frequency from the fundamental frequency. In order to get the detailed depth with reasonable axial resolution, PW Doppler technique is used. The consecutive pulse-echo scanlines are compared parallel direction to get the velocity information.

In aiming, some range is desirable but detailed depth information is not required. Furthermore the transducer is used for imaging and the Doppler aiming, therefore, the range gated CW Doppler technique is appropriate.

The relationship between the Doppler frequency, $f_d$, and the object velocity, $v_0$, is according to equation E2:

$$f_d = f_0 \cdot \frac{v_0}{c + v_0} \approx f_0 \cdot \frac{v_0}{c} \qquad \text{E2}$$

where, $f_0$ is the transmit frequency and c is the speed of sound.

An average maximum velocity of the mitral valve is about 10 cm/s. If the transmit frequency, $f_0$, is 3.7 MHz and the speed of sound is 1540 m/s, the Doppler frequency, $f_d$, created by the mitral valve is about 240 Hz.

Figure 10:
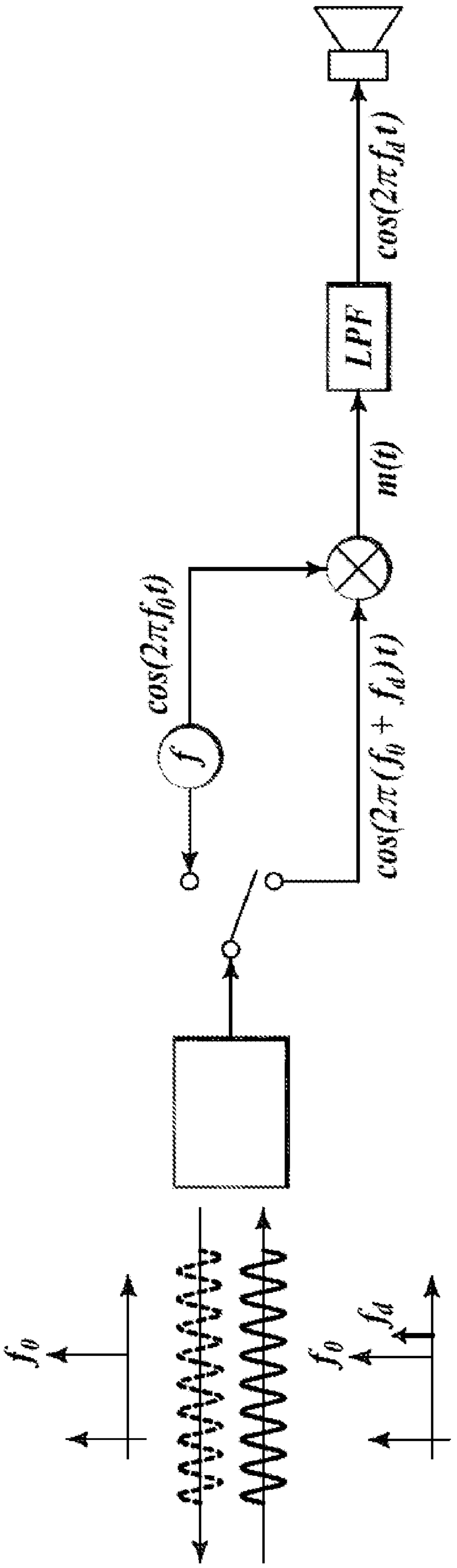
FIG. 10 is a system schematic of the Doppler-speaker circuit of the transceivers 10A-D.

FIG. 10 is a system schematic of the Doppler-speaker circuit of the transceivers 10A-D. The sinusoid wave, $\cos(2\pi f_0 t)$, is transmitted to tissue using a transducer. After certain range-gated time, the sinusoid wave with Doppler frequency component, $f_d$, is received by the transducer. The received signal can be defined as $\cos(2\pi(f_0+f_d)t)$, so that by multiplying the transmit signal and received signal, m(t) is expressed according to equation E3 as:

$$m(t)=\cos(2\pi(f_0+f_d)t)\cdot\cos(2\pi f_0 t) \qquad \text{E3}$$

Using the trigonometric Identity, $\cos x\cdot\cos y=\frac{1}{2}[\cos(x-y)+\cos(x+y)]$, m(t) can be rewritten as equation E4:

$$m(t)=\cos(2\pi(f_0+2f_d)t)+\cos(2\pi f_d t) \qquad \text{E4}$$

The frequency components of m(t) are $(f_0+2f_d)$ and $f_d$, which are a high frequency component and a low frequency component. Therefore using low pass filter whose cutoff frequency is higher than the Doppler frequency, $f_d$, but lower than the fundamental frequency, $f_0$, only the Doppler frequency, $f_d$, is remained, according to E5:

$$LPF\{m(t)\}=\cos(2\pi f_d t) \quad \text{E5}$$

The ultrasound scanning device's loud speaker produces the Doppler sound, when it is in the aiming mode. When the Doppler sound of the mitral valve is audible, the 3D acquisition may be performed.

Figure 11:
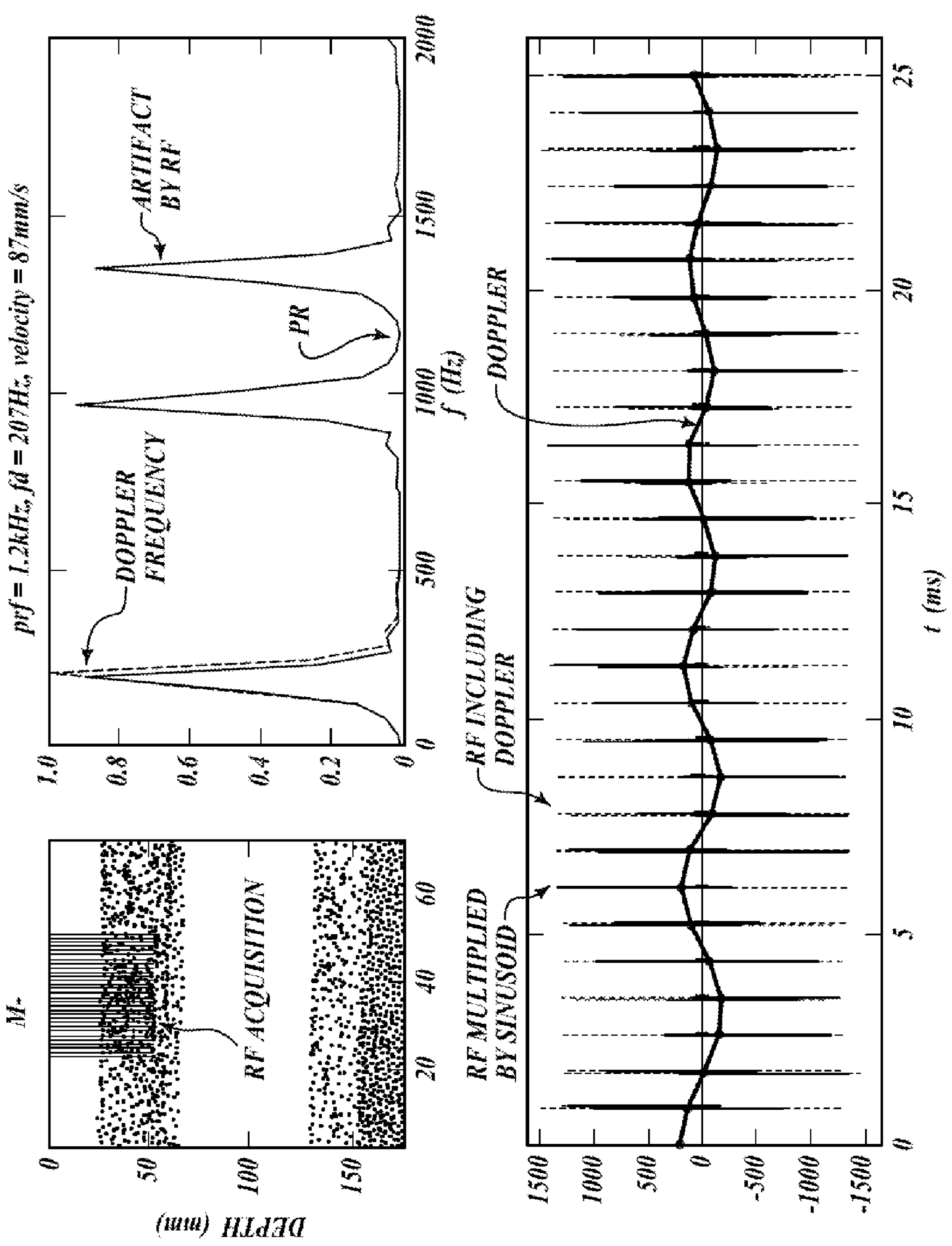
FIG. 11 presents three graphs describing the operation of image acquisition using radio frequency ultrasound (RFUS)

FIG. 11 presents three graphs describing the operation of image acquisition using radio frequency ultrasound (RFUS) and timing to acquire RFUS images at cardiac systole and/or diastole to help determine the cardiac ejection fractions of the left and/or right ventricles. An M-mode US display in the upper left graph is superimposed by the RFUS acquisition range and is presented in the upper right graph as a frequency response of the RFUS lines. The RFUs lines are multiplied by the input sinusoid and the result includes a RFUS discontinuity artifact. The green line in the bottom graph is the filtered signal using an average filter. The time domain representations are of RFUS, multiplied RFUS, and filtered Doppler signal.

FIG. 12 illustrates system 60A for beginning of acquiring 3D data sets acquired during 3D transthoracic echocardiogram procedures. The transceiver 10A-D is placed beneath the sternum at a first freehand position with the scan head 20 aimed slightly towards the apical region of the heart. The heart is shown beneath the sternum and rib cage as in a dashed outline. The three-dimensional ultrasound data is collected during systole and/or diastole at an image-centering position indicated by audible sounds characteristic of Doppler shifts associated with the mitral valve. In concert with the electrocardiograph as explained below, 3D image data sets are acquired at systole and/or diastole upon pressing the scan button 14 on the transceivers 10A-D. After the 3D data set scans are complete, the display 16 on the devices 10A-D displays aiming information in the form of arrows, or alternatively, by sound maxima arising from Doppler shifts. A flashing arrow indicates to the user to point the device in the arrow's direction and rescan at systole or diastole as needed. The scan is repeated until the device displays only a solid arrow or no arrow. The display 16 on the device may also display the calculated ventricular or atrial chamber volumes at systole and/or diastole. The aforementioned aiming process is more fully described in U.S. Pat. No. 6,884,217 to McMorrow et al., which is incorporated by reference as if fully disclosed herein. Once the systole and/or diastole image scanning is complete, the device may be placed on a communication cradle that is attached to a personal computer. Other methods and systems described below incorporate by reference U.S. Pat. Nos. 4,926,871; 5,235,985; 6,569,097; 6,110,111; 6,676,605; 7,004,904; and 7,041,059 as if fully disclosed herein.

The transceiver 10A-D has circuitry that converts the informational content of the scan cones 40/30, translational array 70, or fan array 60 to wireless signal 25C-1 that may be in the form of visible light, invisible light (such as infrared light) or sound-based signals. As depicted, the data is wirelessly uploaded to the personal computer 52 during initial targeting of the heart or other cavity-containing ROI. In a particular embodiment of the transceiver 10A-D, a focused 3.7 MHz single element transducer is used that is steered mechanically to acquire a 120-degree scan cone 42. On a display screen 54 coupled to the computer 52, a scan cone image 40A displays an off-centered view of the heart 56A that is truncated.

Expanding on the protocol described above, and still referring to FIG. 12 the system 60A also includes a personal computing device 52 that is configured to wirelessly exchange information with the transceiver 10C, although other means of information exchange may be employed when the transceiver 10C is used. In operation, the transceiver 10C is applied to a side abdominal region of a patient 68. The transceiver 10B is placed off-center from of the thoracic cavity of the patient 68 to obtain, for example a sub-sternum image of the heart. The transceiver 10B may contact the patient 68 through an ultrasound conveying gel pad that includes an acoustic coupling gel that is placed on the patient 68 sub sternum area. Alternatively, an acoustic coupling gel may be applied to the skin of the patient 68. The pad 67 advantageously minimizes ultrasound attenuation between the patient 68 and the transceiver 10B by maximizing sound conduction from the transceiver 10B into the patient 68.

Wireless signals 25C-1 include echo information that is conveyed to and processed by the image processing algorithm in the personal computer device 52. A scan cone 40 (FIG. 1B) displays an internal organ as partial image 56A on a computer display 54. The image 56A is significantly truncated and off-centered relative to a middle portion of the scan cone 40A due to the positioning of the transceiver 10B.

As shown in FIG. 12, the sub-sternum acquired images are initially obtained during a targeting phase of the imaging. During the initial targeting, a first freehand position may reveal an organ, for example the heart or other ROI 56A that is substantially off-center. The transceivers 10A-D are operated in a two-dimensional continuous acquisition mode. In the two-dimensional continuous mode, data is continuously acquired and presented as a scan plane image as previously shown and described. The data thus acquired may be viewed on a display device, such as the display 54, coupled to the transceivers 10A-D while an operator physically repositions the transceivers 10A-D across the chest region of the patient. When it is desired to acquire data, the operator may acquire data by depressing the trigger 14 of the transceivers 10A-D to acquire real-time imaging that is presented to the operator on the transceiver display 16. If the initial location of the transceiver is significantly off-center, as in the case of the freehand first position, results in only a portion of the organ or cardiac ROI 56A being visible in the scan plane 40A.

FIG. 13 depicts images showing the patient 68 being scanned by the transceivers 10A-D and the data being wirelessly uploaded to a personal computer of a properly targeted cardiac ROI in the left thoracic area between adjacent ribs showing a centered heart or cardiac ROI 56B as properly targeted. The isometric view presents the ultrasound imaging system 60A applied to a centered cardiac region of the patient. The transceiver 10A-D may be translated or moved to a freehand second position between ribs having an apical view of the heart. Wireless signals 25C-2 having information from the transceiver 10C are communicated to the personal computer device 52. An inertial reference unit positioned within the transceiver 10A-D senses positional changes for the transceiver 10C relative to a reference coordinate system. Information from the inertial reference unit, as described in greater detail below, permits updated real-time scan cone image acquisition, so that a scan cone 40B having a complete image of the organ 56B can be obtained.

FIG. 14 depicts an alternate embodiment 70A of the cardiac imaging system using an electrocardiograph in communication with a wireless ultrasound transceiver. System 70A includes the speaker 15 equipped transceiver 10A-D in wireless signal communication with an electrocardiograph 74 and the personal computer device 52. The electrocardiograph 74 includes a display 76 is in wired communication with the patient through electrical contacts 78. Cardio activity of the patient's heart is shown as a PQRST wave on display 76 in which the timing for acquisition of 3D datasets at systole and diastole may be undertaken when the heart 56B is centered within the scan cone 40B on the display 54 of the computing device 52. Wireless signal 80 from the electrocardiograph 74 signals the transceiver 10A-D for acquisition of 3D datasets at systole and diastole which in turn is wireless transmitted to the personal computer device 52. Other information from the electrocardiograph 74 to the personal computer device 52 may be conveyed via wireless signal 82.

FIG. 15 depicts an alternate embodiment 70B of the cardiac imaging system using an electrocardiograph in communication with a wired connected ultrasound transceiver. System 70B includes wired cable 84 connecting the electrocardiograph 74 and speaker-equipped transceivers 10A-D and cable 86 connecting the transceivers 10A-D to the computing device 52. Similar in operation to wireless system 70A, the electrocardiograph 74 signals the transceiver 10A-D for acquisition of 3D datasets at systole and diastole via cable 84 and information of the 3D datasets are conveyed to the computer device 52 via cable 86. Other information from the electrocardiograph 74 to the personal computer device 52 may be conveyed via wireless signal 82. Alternatively, the electrocardiograph 74 may convey signals directly to the computing device 52 by wired cables.

Alternate embodiments of systems 70A and 70B allow for different signal sequence communication between the transceivers 10A-D, 10E, electrocardiograph 74 and computing device 52. That is, different signal sequences may be used in executing the timing of diastole and systole image acquisition. For example, the electrocardiograph 74 may signal the computing device 52 to trigger the transceivers 10A-D and 10E to initiate image acquisition at systole and diastole.

FIG. 16 schematically depicts an alternate embodiment of the cardiac imaging system during Doppler targeting with microphone equipped transceivers 10A-D. Mitral valve mitigation of Doppler shifting is audibly recognizable as the user moves the transceiver A-D to different chest locations to find a chest region to acquire systole and/or diastole centered 3D data sets. Audible wave set 90 is heard by the sonographer emanating from transceiver's 10A-D speaker 15. The cardio activity PQRST is presented on display 76 of the electrocardiograph 74.

FIG. 17 schematically depicts an alternate embodiment of the cardiac imaging system during Doppler targeting of a speaker-less transceiver 10E with a speaker-equipped electrocardiograph. Similar in operation to the alternate embodiment of FIG. 16, in this schematic the alternate embodiment includes the speaker or speakers 74A located on the electrocardiograph 74. Upon a user moving the transceiver 10E to different chest locations, the mitral mitigating Doppler shift is heard from electrocardiograph speakers 74A released as audio wave sets 94 to indicate optimal mitral valve centering at a given patient chest location for subsequent acquisition of the systole and/or diastole centered 3D data sets.

FIG. 18 is a schematic illustration and partial isometric view of a network connected cardio imaging ultrasound system 100 in communication with ultrasound imaging systems 60A-D. The system 100 includes one or more personal computer devices 52 that are coupled to a server 56 by a communications system 55. The devices 52 are, in turn, coupled to one or more ultrasound transceivers 10A-D in systems 60A-B used with the 3D datasets downloaded to the computer 52 substantially operating simultaneously with the electrocardiographs, or transceivers 10A-E of systems 60C-D where the systole and/or diastole 3D data sets are downloaded from the cradles 50A-B sequentially and separate from the electrocardiographs. The server 56 may be operable to provide additional processing of ultrasound information, or it may be coupled to still other servers (not shown in FIG. 17) and devices, for examples transceivers 10E may be equipped with a snap on collars having speaker configured to audibly announce changes in mitral valve mitigated Doppler shifting. Once the systole and/or diastole scans are complete, the three-dimensional data may be transmitted securely to a server computer on a remote computer that is coupled to a network, such as the Internet.

Alternately, a local computer network, or an independent standalone personal computer may also be used. In any case, image processing algorithms on the computer analyze pixels within a 2D portion of a 3D image or the voxels of the 3D image. The image processing algorithms then define which pixels or voxels occupy or otherwise constitute an inner or outer wall layer of a given wall chamber. Thereafter, wall areas of the inner and outer chamber layers, and thickness between them, is determined. Inter-chamber wall weight is determined as a product of wall layer area, thickness between the wall layers, and density of the wall.

FIG. 19 is a schematic illustration and partial isometric view of an Internet connected cardio imaging ultrasound system 110 in communication with ultrasound imaging systems 60A-D. The Internet system 110 is coupled or otherwise in communication with the systems 60A-60D. The system 110 may also be in communication with the transceiver a snap on microphone collar described above.

FIG. 20 is an algorithm flowchart 200 for the method to measure and determine heart chamber volumes, changes in heart chamber volumes, ICWT and ICWM and begins with two entry points depending if a new training database of sonographer or manually segmented images is being created and/or expanded, or whether a pre-existing and developed sonographer database is being used. In the case wherein the sonographer database is being created and/or expanded, at entry point Start-1, an image database of manually segmented ROIs is created by an expert sonographer at process block 204. Alternatively, entry point Start-1 may begin at process block 224, wherein an image database of manually segmented ROIs is created that is enhanced by a Radon Transform by an expert sonographer. Thereafter, at process block 260, image-processing algorithms are trained to substantially reproduce the appearance of the manually segmented ROIs contained in the database by the use of created statistical shape models as further described below. Once the level set algorithms are trained on the manually segmented image collections, algorithm 200 continues at process block 280 where new or non-database images are acquired from 3D transthoracic echocardiographic procedures obtained from any of the aforementioned systems. The non-database images are composed of 3D data sets acquired during systole and diastole as further described below. If the combined database from process blocks 204 and 224 is already created and developed, an alternate entry point is depicted by entering algorithm flowchart 200 via Start-2 into process block 260 for acquisition of non-database images at systole and diastole. After acquisition of non-database images, algorithm 200 continues at process block 300 where structures within the ROI of the non-database 3D data sets are segmented using the trained image processing algorithms from process block 260. Finally, the algorithm 200 is completed at process block 310 where at least one of ICWT, ICWM, and the ejection fraction of at least one heart chamber is determined from information of the segmented structures of the non-database image.

FIG. 21 is an expansion of sonographer-executed sub-algorithm 204 of flowchart in FIG. 20 that utilizes a 2-step enhancement process. 3D data sets are entered at input data process block 206 which then undergoes a 2-step image enhancement procedure at process block 208. The 2-step image enhancement includes performing a heat filter to reduce noise followed by a shock filter to sharpen edges of structures within the 3D data sets. The heat and shock filters are partial differential equations (PDE) defined respectively in Equations E6 and E7 below:

$$\frac{\partial u}{\partial t} = \frac{\partial^2 u}{\partial x^2} + \frac{\partial^2 u}{\partial y^2} \text{ (Heat Filter)} \quad \text{E6}$$

$$\frac{\partial u}{\partial t} = -F(\lambda(u))\|\nabla u\| \text{ (Shock Filter)} \quad \text{E7}$$

Here u in the heat filter represents the image being processed. The image u is 2D, and is comprised of an array of pixels arranged in rows along the x-axis, and an array of pixels arranged in columns along the y-axis. The pixel intensity of each pixel in the image u has an initial input image pixel intensity (I) defined as $u_0$=I. The value of I depends on the application, and commonly occurs within ranges consistent with the application. For example, I can be as low as 0 to 1, or occupy middle ranges between 0 to 127 or 0 to 512. Similarly, I may have values occupying higher ranges of 0 to 1024 and 0 to 4096, or greater. For the shock filter u represents the image being processed whose initial value is the input image pixel intensity (I): $u_0$=I where the λ(u) term is the Laplacian of the image u, F is a function of the Laplacian, and ||∇u|| is the 2D gradient magnitude of image intensity defined by equation E8:

$$\|\nabla u\| = \sqrt{u^2_x + u^2_y} \quad \text{E8}$$

Where $u^2_x$=the square of the partial derivative of the pixel intensity (u) along the x-axis, $u^2_y$=the square of the partial derivative of the pixel intensity (u) along the y-axis, the Laplacian λ(u) of the image, u, is expressed in equation E9:

$$\lambda(u) = u_{xx}u_x^2 + 2u_{xy}u_xu_y + u_{yy}u_y^2 \quad \text{E9}$$

Equation E9 relates to equation E6 as follows:

$u_x$ is the first partial derivative $$\frac{\partial u}{\partial x}$$

of u along the x-axis, $u_x$ $u_y$ is the first partial derivative $$\frac{\partial u}{\partial y}$$

of u along the y-axis, $u_x$ $u_x^2$ is the square of the first partial derivative $$\frac{\partial u}{\partial x}$$

of u along the x-axis, $u_x$ $u_y^2$ is the square of the first partial derivative $$\frac{\partial u}{\partial y}$$

of u along the y-axis, $u_x$ $u_{xx}$ is the second partial derivative $$\frac{\partial^2 u}{\partial x^2}$$

of u along the x-axis, $u_x$ $u_{yy}$ is the second partial derivative $$\frac{\partial^2 u}{\partial y^2}$$

of u along the y-axis, $u_{xy}$ is cross multiple first partial derivative $$\frac{\partial u}{\partial xdy}$$

of u along the x and y axes, and $u_{xy}$ the sign of the function F modifies the Laplacian by the image gradient values selected to avoid placing spurious edges at points with small gradient values:

$$F(\lambda(u)) = \begin{cases} 1, & \text{if } \lambda(u) > 0 \text{ and } \|\nabla u\| > t \\ -1, & \text{if } \lambda(u) < 0 \text{ and } \|\nabla u\| > t \\ 0, & \text{otherwise} \end{cases}$$

where t is a threshold on the pixel gradient value ||∇u||.

The combination of heat filtering and shock filtering produces an enhanced image ready to undergo the intensity-based and edge-based segmentation algorithms as discussed below. The enhanced 3D data sets are then subjected to a parallel process of intensity-based segmentation at process block 210 and edge-based segmentation at process block 212. The intensity-based segmentation step uses a "k-means" intensity clustering technique where the enhanced image is subjected to a categorizing "k-means" clustering algorithm. The "k-means" algorithm categorizes pixel intensities into white, gray, and black pixel groups. Given the number of desired clusters or groups of intensities (k), the k-means algorithm is an iterative algorithm comprising four steps: Initially determine or categorize cluster boundaries by defining a minimum and a maximum pixel intensity value for every white, gray, or black pixels into groups or k-clusters that are equally spaced in the entire intensity range. Assign each pixel to one of the white, gray or black k-clusters based on the currently set cluster boundaries. Calculate a mean intensity for each pixel intensity k-cluster or group based on the current assignment of pixels into the different k-clusters. The calculated mean intensity is defined as a cluster center. Thereafter, new cluster boundaries are determined as mid points between cluster centers. The fourth and final step of intensity-based segmentation determines if the cluster boundaries significantly change locations from their previous values. Should the cluster boundaries change significantly from their previous values, iterate back to step 2, until the cluster centers do not change significantly between iterations. Visually, the clustering process is manifest by the segmented image and repeated iterations continue until the segmented image does not change between the iterations.

The pixels in the cluster having the lowest intensity value—the darkest cluster—are defined as pixels associated with internal regions of cardiac chambers, for example the left or right ventricles of the left and/or right atriums. For the 2D algorithm, each image is clustered independently of the neighboring images. For the 3D algorithm, the entire volume is clustered together. To make this step faster, pixels are sampled at 2 or any multiple sampling rate factors before determining the cluster boundaries. The cluster boundaries determined from the down-sampled data are then applied to the entire data.

The edge-based segmentation process block 212 uses a sequence of four sub-algorithms. The sequence includes a spatial gradients algorithm, a hysteresis threshold algorithm, a Region-of-Interest (ROI) algorithm, and a matching edges filter algorithm. The spatial gradient algorithm computes the x-directional and y-directional spatial gradients of the enhanced image. The hysteresis threshold algorithm detects salient edges. Once the edges are detected, the regions defined by the edges are selected by a user employing the ROI algorithm to select regions-of-interest deemed relevant for analysis.

Since the enhanced image has very sharp transitions, the edge points can be easily determined by taking x- and y-derivatives using backward differences along x- and y-directions. The pixel gradient magnitude $\|\nabla I\|$ is then computed from the x- and y-derivative image in equation E10 as:

$$\|\nabla I\| = \sqrt{I^2_x + I^2_y} \qquad \text{E10}$$

Where $I^2_x$=the square of x-derivative of intensity and $I^2_y$=the square of y-derivative of intensity along the y-axis.

Significant edge points are then determined by thresholding the gradient magnitudes using a hysteresis thresholding operation. Other thresholding methods could also be used. In hysteresis thresholding 530, two threshold values, a lower threshold and a higher threshold, are used. First, the image is thresholded at the lower threshold value and a connected component labeling is carried out on the resulting image. Next, each connected edge component is preserved which has at least one edge pixel having a gradient magnitude greater than the upper threshold. This kind of thresholding scheme is good at retaining long connected edges that have one or more high gradient points.

In the preferred embodiment, the two thresholds are automatically estimated. The upper gradient threshold is estimated at a value such that at most 97% of the image pixels are marked as non-edges. The lower threshold is set at 50% of the value of the upper threshold. These percentages could be different in different implementations. Next, edge points that lie within a desired region-of-interest are selected. This region of interest algorithm excludes points lying at the image boundaries and points lying too close to or too far from the transceivers 10A-D. Finally, the matching edge filter is applied to remove outlier edge points and fill in the area between the matching edge points.

The edge-matching algorithm is applied to establish valid boundary edges and remove spurious edges while filling the regions between boundary edges. Edge points on an image have a directional component indicating the direction of the gradient. Pixels in scanlines crossing a boundary edge location can exhibit two gradient transitions depending on the pixel intensity directionality. Each gradient transition is given a positive or negative value depending on the pixel intensity directionality. For example, if the scanline approaches an echo reflective bright wall from a darker region, then an ascending transition is established as the pixel intensity gradient increases to a maximum value, i.e., as the transition ascends from a dark region to a bright region. The ascending transition is given a positive numerical value. Similarly, as the scanline recedes from the echo reflective wall, a descending transition is established as the pixel intensity gradient decreases to or approaches a minimum value. The descending transition is given a negative numerical value.

Valid boundary edges are those that exhibit ascending and descending pixel intensity gradients, or equivalently, exhibit paired or matched positive and negative numerical values. The valid boundary edges are retained in the image. Spurious or invalid boundary edges do not exhibit paired ascending-descending pixel intensity gradients, i.e., do not exhibit paired or matched positive and negative numerical values. The spurious boundary edges are removed from the image.

For cardiac chamber volumes, most edge points for blood fluid surround a dark, closed region, with directions pointing inwards towards the center of the region. Thus, for a convex-shaped region, the direction of a gradient for any edge point, the edge point having a gradient direction approximately opposite to the current point represents the matching edge point. Those edge points exhibiting an assigned positive and negative value are kept as valid edge points on the image because the negative value is paired with its positive value counterpart. Similarly, those edge point candidates having unmatched values, i.e., those edge point candidates not having a negative-positive value pair, are deemed not to be true or valid edge points and are discarded from the image.

The matching edge point algorithm delineates edge points not lying on the boundary for removal from the desired dark regions. Thereafter, the region between any two matching edge points is filled in with non-zero pixels to establish edge-based segmentation. In a preferred embodiment of the invention, only edge points whose directions are primarily oriented co-linearly with the scanline are sought to permit the detection of matching front wall and back wall pairs of a cardiac chamber, for example the left or right ventricle.

Referring again to FIG. 21, results from the respective segmentation procedures are then combined at process block 214 and subsequently undergoes a cleanup algorithm process at process block 216. The combining process of block 214 uses a pixel-wise Boolean AND operator step to produce a segmented image by computing the pixel intersection of two images. The Boolean AND operation represents the pixels of each scan plane of the 3D data sets as binary numbers and the corresponding assignment of an assigned intersection value as a binary number 1 or 0 by the combination of any two pixels. For example, consider any two pixels, say $pixel_A$ and $pixel_B$, which can have a 1 or 0 as assigned values. If $pixel_A$'s value is 1, and $pixel_B$'s value is 1, the assigned intersection value of $pixel_A$ and $pixel_B$ is 1. If the binary value of $pixel_A$ and $pixel_B$ are both 0, or if either $pixel_A$ or $pixel_B$ is 0, then the assigned intersection value of $pixel_A$ and $pixel_B$ is 0. The Boolean AND operation takes the binary any two digital images as input, and outputs a third image with the pixel values made equivalent to the intersection of the two input images.

After combining the segmentation results, the combined pixel information in the 3D data sets In a fifth process is cleaned at process block 216 to make the output image smooth and to remove extraneous structures not relevant to cardiac chambers or inter-chamber walls. Cleanup 216 includes filling gaps with pixels and removing pixel groups unlikely to be related to the ROI undergoing study, for example pixel groups unrelated to cardiac structures. Segmented and clean structures are then outputted to process block 262 of FIG. 23 below, and/or processed in block 218 for determination of ejection fraction of ventricles or atria, or to calculate other cardiac parameters (ICWT, ICWM). The calculation of ejection fractions or inter-chamber wall masses in block 218 may require the area or the volume of the segmented region-of-interest to be computed by multiplying pixels by a first resolution factor to obtain area, or voxels by a second resolution factor to obtain volume. For example, for pixels having a size of 0.8 mm by 0.8 mm, the first resolution or conversion factor for pixel area is equivalent to 0.64 $mm^2$, and the second resolution or conversion factor for voxel volume is equivalent to 0.512 $mm^3$. Different unit lengths for pixels and voxels may be assigned, with a proportional change in pixel area and voxel volume conversion factors.

FIG. 22 is an expansion of sonographer-executed sub-algorithm 224 of flowchart in FIG. 20 that utilizes a 3-step enhancement process, radon transform enhancement, 3D data sets are entered at input data process block 226 which then undergoes a 3-step image enhancement procedure at process blocks 228 (radon transform), 230 (heat filter), and 232 (shock filter). The heat and shock filters 230 and 232 are substantially the same as the heat and shock filters of the image enhancement process block 208 of FIG. 21. The radon transform enhancement block 228 improves the contrast of the image sets by the application of horizontal and vertical filters to the pixels by applying an integral function across scan lines within the scan planes of the 3D data sets. The effect of the radon transform is to provide a reconstructed image from multi-planar scans and presents an image construct as a collection of blurred sinusoidal lines with different amplitudes and phases. After performing the radon transform, the reconstructed image is then subjected to the respective sequence of the heat filter 230 followed the shock filter 232. Thereafter, segmentation via parallel procedures are respectively undertaken with a 3-step region-based segmentation comprising blocks 234 (estimate shadow regions), 236 (automatic region threshold) and 238 (remove shadow regions) in parallel with and a 2-step edge-based segmentation comprising blocks 240 (spatial gradients) and 242 (hysteresis threshold of gradients).

The estimate shadow regions 234 looks for structures hidden in dark or shadow regions of scan planes within 3D data sets that would complicate the segmentation of heart chambers (for example, the segmentation of the left ventricle boundary) were they not known and segmentation artifacts or noise accordingly compensated before determining ejection fractions (See FIG. 53 below for example of boundary artifacts that appear by engaging the estimate shadow regions algorithm 234). The automatic region threshold 236 block, in a particular embodiment, automatically estimates two thresholds, an upper and a lower gradient threshold. The upper gradient threshold is estimated at a value such that at most 97% of the image pixels are marked as non-edges. The lower threshold is set at 50% of the value of the upper threshold. These percentages could be different in alternate embodiments. Next, edge points that lie within a desired region-of-interest are selected and those points lying at the image boundaries or too close or too far from the transceivers 10A-D are excluded. Finally, shadow regions are removed at process block 238 by removing image artifacts or interferences from non-chamber regions of the scan planes. For example, wall artifacts are removed from the left ventricle.

The spatial gradient 240 computes the x-directional and y-directional spatial gradients of the enhanced image. The hysteresis threshold 242 algorithm detects significant edge points of salient edges. The edge points are determined by thresholding the gradient magnitudes using a hysteresis thresholding operation. Other thresholding methods could also be used. In the hysteresis thresholding 242 block, two threshold values, a lower threshold and a higher threshold, are used. First, the image is thresholded at the lower threshold value and a connected component labeling is carried out on the resulting image. Next, each connected edge component is preserved which has at least one edge pixel having a gradient magnitude greater than the upper threshold. This kind of thresholding scheme is good at retaining long connected edges that have one or more high gradient points. Once the edges are detected, the regions defined by the edges are selected by employing the sonographer's expertise in selecting a given ROI deemed relevant by the sonographer for further processing and analysis.

Referring still to FIG. 22, a combine region and edges algorithm 244 is applied to parallel segmentation processes above in a manner substantially similar to the combine block 214 of FIG. 21. The combined results from process block 244 are then subjected to a morphological cleanup process 246 in which cleanup is achieved by removing pixel sets whose size is smaller than a structuring pixel element of a pixel group cluster. Thereafter, a snakes-based cleanup block 248 is applied to the morphologically cleaned data sets wherein the snakes cleanup is not limited to using a stopping edge-function based on the gradient of the image for the stopping process, but instead can detect contours both with and without gradients. For example, shapes having very smooth boundaries or discontinuous boundaries. In addition, the snake-base cleanup block 248 includes a level set formulation to allow the automatic detection of interior contours with the initial curve positionable anywhere in the image. Thereafter, at terminator block 250, the segmented image is outputted to block 262 of FIG. 23.

FIG. 23A is an expansion of sub-algorithm 260 of flowchart algorithm depicted in FIG. 20. Sub-algorithm 260 employs level set algorithms and constitutes a training phase section comprised of four process blocks. The first process block 262, acquire training shapes, is entered from either segmented image cleanup block 216 of FIG. 21 or output segmented image block 250 of FIG. 22. Once training shapes are acquired, the training phase continues with level set algorithms employed in blocks 264 (align shape by gradient descent), 266 (generate signed distance map), and 268 (extract mean shape and Eigen shapes). The training phase is then concluded and exits to process block 280 for acquiring a non-database image further described in FIG. 24 below.

FIG. 23B is an expansion of sub-algorithm 300 of flowchart algorithm depicted in FIG. 20 for application to non-database images acquired in process block 280. Sub-algorithm 300 constitutes the segmentation phase of the trained level set algorithms and begins by entry from process 280 wherein the non-database images are first subjected to intensity gradient analysis in a minimize shape parameters by gradient descent block 302. After gradient descent block 302, an Update shape image value Φ block 304 using level set algorithms described by equations E11-E19 below. Once the image Φ value has been updated, then at process block 306, the inside and outside curvature C-lines from the updated image value Φ is determined. Thereafter, a decision diamond 308 presents the query "Do inside and outside C-lines converge?"—and if the answer is negative, sub-algorithm 300 returns to process block 302 for re-iteration of the segmentation phase. If the answer is affirmative, then the segmentation phase is complete and sub-algorithm 300 then exits to process block 310 of algorithm 200 for determination of at least one of ICWT, ICWM, and ejection fraction using the segmentation results of the non-database image obtained by application of the trained level set algorithms.

FIG. 24 is an expansion of sub-algorithm 280 of flowchart 280 flowchart in FIG. 20. Entering from process 276, the speaker-equipped ultrasound transceiver 10A-D is positioned over the chest wall to scan at least a portion of the heart and receive ultrasound echoes returning from the exterior and internal surfaces of the heart per process block 282. Alternatively, the non-speaker equipped transceiver 10E is positioned over the chest wall and Doppler sounds characteristic for detecting maximum mitral valve centering is heard from speakers connected with the electrocardiograph 74. At process block 284, Doppler signals are generated in proportion to the echoes, and the Doppler signals are processed to sense the presence of the mitral valve. At decision diamond 286, a query "Is heart sufficiently targeted" is presented. If affirmative for sufficient targeting because Doppler sounds emanating from the transceiver 10A-D speaker 15 (or speakers of electrocardiograph 74) is indicative of sufficient detection of the mitral valve, then sub-algorithm 280 proceeds to process block 290 wherein 3D data sets are acquired at systole and diastole. If negative for sufficient heart targeting, the at process block 288 the transceiver 10A-D or transceiver 10E is repositioned over the chest wall to a location that generates Doppler signals indicating the maximum likelihood of mitral valve detection and centering so that acquisition of 3D data sets per step 290 may proceed. After acquisition of systole and diastole 3D data sets, the 3D data sets are then processed using trained level set algorithms per process block 292. Sub-algorithm 280 is completed and exits to sub-algorithm 300.

FIG. 25 is an expansion of sub-algorithm 310 of flowchart in FIG. 20. Entering from process block 292, adjacent cardiac chamber boundaries are delineated at process block 312 using the database trained level set algorithms. Alternatively, the ICWT is measured at block 316, or may be measured after block 312. The surface areas along the heart chamber volumes are calculated at process block 314. Thereafter, the volume between the heart chambers and the volume of the heart chambers at systole and diastole are determined at process block 320 knowing the surface area from block 314 and the thickness from block 316. From block 320, the ICWM, Left Ventricle ejection fraction, and Right Ventricle Ejection fraction may be respectively calculated at process blocks 322, 324, and 328. In the case of the Left or right Atria, the respective volumes and ejection fractions may be calculated as is done for the Left and Right Ventricles.

FIG. 26 is an 8-image panel exemplary output of segmenting the left ventricle by processes of sub-algorithm 220. The 8-image panel represents an exemplary output of segmenting the left ventricle by processes of sub-algorithm 220. Panel images include (a) Original Image, (b) After radon-transform-based image enhancement, (c) After heat & shock-based image enhancement (d) Shadow region detection result (c) Intensity segmentation result (f) Edge-detection segmentation result (g) Combination of intensity and edge-based segmentation results (h) After morphological cleanup, (i) after snakes-based cleanup (j) segmented region overlaid on the original image.

FIG. 27 presents a scan plane image with ROI of the heart delineated with echoes returning from 3.5 MHz pulsed ultrasound. Here the right ventricle (RV) and left ventricle (LV) is shown as dark chambers with an echogenic or brighter appearing wall (W) interposed between the ventricles. Beneath the bottom fan portion of the scan plane 242 is a PQRST cardiac wave tracing to help determine when 3D data sets can be acquired at systole and/or diastole.

FIG. 28 is a schematic of application of snakes processing block of sub-algorithm 248 to an active contour model. Here an abrupt transition between a circularly shaped dark region from external bright regions is mitigated by an edge function curve F. The snakes processing block relies upon edge-function F to detect objects defined by a gradient $-\alpha|VI|$ that produces an asymptotic curve distribution $e^{-\alpha|VI|}$ in the plot off F vs. $|VI|$. Depending on the image gradient, the curve evolution becomes limited. Geometric active contours are represented implicitly as level set functions and evolve according to an Eulerian formulation. These geometric active contours are intrinsic and advantageously are independent of the parameterization of evolving contours since parameterization doesn't occur until the level set function is completed, thereby avoiding having to add or remove nodes from an initial parameterization or to adjust the spacing of the nodes as in parametric models. The intrinsic geometric properties of the contour such as the unit normal vector and the curvature can be easily computed from the level set function. This contrasts with the parametric case, where inaccuracies in the calculations of normals and curvature result from the discrete nature of the contour parameterization. Third, the propagating contour can automatically change topology in geometric models (e.g., merge or split) without requiring an elaborate mechanism to handle such changes as in parametric models. Fourth, the resulting contours do not contain self-intersections, which are computationally costly to prevent in parametric deformable models.

There are many advantages of geometric deformable models among them the Level Set Methods are increasingly used for image processing in a variety of applications. Front evolving geometric models of active contours are based on the theory of curve evolution, implemented via level set algorithms. The automatically handle changes in topology when numerically implemented using level sets. Hence, without resorting to dedicated contour tracking, unknown numbers of multiple objects can be detected simultaneously. Evolving the curve C in normal direction with speed F amounts to solve the differential equation according to equation E11:

$$\frac{\partial \Phi}{\partial t} = |\nabla \Phi| F,\ \Phi(0, x, y) = \Phi_0(x, y) \qquad \text{E11}$$

$$\frac{\partial \Phi}{\partial t} = |\nabla \Phi| g(|\nabla u_0|)\left(\operatorname{div}\left(\frac{\nabla \Phi}{|\nabla \Phi|}\right) + \gamma\right) \qquad \text{E12}$$

A geodesic model has been proposed. This is a problem of geodesic computation in a Riemannian space, according to a metric induced by the image. Solving the minimization problem consists in finding the path of minimal new length in that metric according to equation E13:

$$J(C) = 2\int_0^1 |C'(s)| \cdot g(|\nabla u_0(C(s))|)\,ds \qquad \text{E13}$$

where the minimizer C can be obtained when $g(|\nabla u_0 (C(s))|)$ vanishes, i.e., when the curve is on the boundary of the object. The geodesic active contour model also has a level set formulation as following, according to equation E14:

$$\frac{\partial \Phi}{\partial t} = |\nabla \Phi|\left(div\left(g(|\nabla u_0|)\frac{\nabla \Phi}{|\nabla \Phi|}\right) + vg(|\nabla u_0|)\right) \quad \text{E14}$$

The geodesic active contour model is based on the relation between active contours and the computation of geodesics or minimal distance curves. The minimal distance curve lies in a Riemannian space whose metric is defined by the image content. This geodesic approach for object segmentation allows connecting classical "snakes" based on energy minimization and geometric active contours based on the theory of curve evolution. Models of geometric active contours are used, allowing stable boundary detection when their gradients suffer from large variations.

In practice, the discrete gradients are bounded and then the stopping function is not zero on the edges, and the curve may pass through the boundary. If the image is very noisy, the isotropic smoothing Gaussian has to be strong, which can smooth the edges too. This region based active contour method is a different active contour model, without a stopping edge-function, i.e. a model which is not based on the gradient of the image for the stopping process. A kind of stopping term is based on Mumford-Shah segmentation techniques. In this way, the model can detect contours either with or without gradient, for instance objects with very smooth boundaries or even with discontinuous boundaries. In addition, the model has a level set formulation, interior contours are automatically detected, and the initial curve can be anywhere in the image. The original Mumford-Shah functional (D. Mumford and J. Shah, "Optimal approximations by piecewise smooth functions and associated variational problems", Comm. Pure App. Math., vol. 42, pp. 577-685, 1989) is defined by equation E15:

$$F^{MS}(u, C) = \mu \mathrm{Length}(C) + \lambda\int_{\Omega}|u_0(x, y) - u(x, y)|^2 dxdy + \lambda\int_{\Omega\setminus C}|\nabla u(x, y)|^2 dxdy \quad \text{E15}$$

The smaller the Mumford-Shah F, the segmentation improves as $u_0$ approximates original image u, $u_0$ does not vary too much on each segmented region $R_i$, and the boundary C is as short as possible. Under these conditions $u_0$ it becomes a new image of the original image u drawn with sharp edges. The objects are drawn smoothly without texture. These new images are perceived correctly as representing the same scene as a simplification of the scene containing most of its features.

FIG. 29 is a schematic of application of level-set processing block of sub-algorithm 250 to an active contour model depicted by a dark circle partially merged with a dark square. Here the level set approach may solve the modified Mumford-Shah functional. In order to explain the model clearly, the evolving curve C is defined in terms of Ω, as for example, the boundary of an open subset w of Ω. In what follows, inside(C) denotes the region w, and outside(C) denotes the region $\Omega/\overline{w}$. The method is the minimization of an energy based-segmentation. Assume that the image $u_0$ is formed by two regions of approximately piecewise-constant intensities, of distinct values $u_0^i$ and $u_0^0$. Assume further that the object to be detected is represented by the region with the value $u_0^i$. Let denote its boundary by $C_0$. Then we have $u_0 \approx u_0^i$ inside the object [or inside ($C_0$)], and $u_0 \approx u_0^0$ outside the object [or outside ($C_0$)] where $\mu \geqq 0$, $v \geqq 0$, $\lambda_1, \lambda_2 \geqq 0$. In Chan and Vese's approach, $\lambda_1 = \lambda_2 = 1$ and $v = 0$ (T. F. Chan and L. A. Vese. Active Contours Without Edges. IEEE Transactions on Image Processing, 10:266-277, 2001).

The level set functions are defined by equations E16-E19:

$$\left\{\begin{array}{l} C = \partial w = \{(x, y) \in \Omega : \Phi(x, y) = 0\} \\ inside(C) = w = \{(x, y) \in \Omega : \Phi(x, y) > 0\} \\ outside(C) = \Omega \setminus \overline{w} = \{(x, y) \in \Omega : \Phi(x, y) < 0\} \end{array}\right\} \quad \text{E16}$$

$$H(z) = \begin{cases} 1, & (z \geq 0) \\ 0, & (z < 0) \end{cases}, \quad \delta_0 = \frac{dH(z)}{dz}. \quad \text{E17}$$

The functional may be solved using following equation, E18:

$$F(c_1, c_2, \Phi) = \mu\int_{\Omega}\delta(\Phi(x,y))|\nabla\Phi(x,y)|dxdy + v\int_{\Omega}H(\Phi(x,y))dxdy + \lambda_1\int_{inside(C)}|u_0(x,y) - c_1|^2 H(\Phi(x,y))dxdy + \lambda_2\int_{outside(C)}|u_0(x,y) - c_2|^2(1 - H(\Phi(x,y)))dxdy \quad \text{E18}$$

And, according to equation E19:

$$\frac{\partial \Phi}{\partial t} = \delta(\Phi)\left[\mu div\left(\frac{\nabla \Phi}{|\nabla \Phi|}\right) - v - \lambda_1(u_0 - c_1)^2 + \lambda_2(u_0 - c_2)^2\right]. \quad \text{E19}$$

Image segmentation using shape prior missing or diffuse boundaries is a very challenging problem for medical image processing, which may be due to patient movements, low SNR of the acquisition apparatus or being blended with similar surrounding tissues. Under such conditions, without a prior model to constrain the segmentation, most algorithms (including intensity-and curve-based techniques) fail-mostly due to the under-determined nature of the segmentation process. Similar problems arise in other imaging applications as well and they also hinder the segmentation of the image. These image segmentation problems demand the incorporation of as much prior information as possible to help the segmentation algorithms extract the tissue of interest.

A number of model-based image segmentation algorithms are used to correct boundaries in medical images that are smeared or missing. Alternate embodiments of the segmentation algorithms employ parametric point distribution models for describing segmentation curves. The alternate embodiments include using linear combinations of appearance derived eigenvectors that incorporate variations from the mean shape to correct missing or smeared boundaries, including those that arise from variations in transducer angular viewing or alterations of subject pose parameters. These aforementioned point distribution models are determined to match the points to those having significant image gradients. A particular embodiment employs a statistical point model for the segmenting curves by applying principal component analysis (PCA) in a maximum a-posteriori Bayesian framework that capture the statistical variations of the covariance matrices associated with landmark points within a region of interest. Edge-detection and boundary point correspondence within the image gradients are determined within the framework of the region of interest to calculate segmentation curves under varying poses and shape parameters. The incorporated shape information as a prior model restricts the flow of geodesic active contours so that prior parametric shape models are derived by performing PCA on a collection of signed distance maps of the training shape. The segmenting curve then evolves according to the gradient force of the image and the force exerted by the estimated shape. An "average shape" serves as the shape prior term in their geometric active contour model.

Implicit representation of the segmenting curve has been proposed in and calculated the parameters of the implicit model to minimize the region-based energy based on Mumford-Shah functional for image segmentation. The proposed method gives a new and efficient frame work for segmenting image contaminated by heavy noise and delineating structures complicated by missing or diffuse boundaries.

The shape model training phase of FIG. 23 begins with acquiring a set of training shapes per process block 262. Here a set of binary images $\{B^1, B^2, \ldots, B^n\}$, each is with 1 as object and 0 as the background. In order to extract the accurate shape information, alignment is applied. Alignment is a task to calculate the following pose parameters $p=[a,b,h,\theta]^T$ and correspondingly these four parameters are for translation in x, y, scale and rotation, according to equation E20:

$$T(p) = \begin{bmatrix} 1 & 0 & a \\ 0 & 1 & b \\ 0 & 0 & 1 \end{bmatrix} \begin{bmatrix} h & 0 & 0 \\ 0 & h & 0 \\ 0 & 0 & h \end{bmatrix} \begin{bmatrix} \cos(\theta) & -\sin(\theta) & 0 \\ \sin(\theta) & \cos(\theta) & 0 \\ 0 & 0 & 1 \end{bmatrix} \quad \text{E20}$$

The strategy to compute the pose parameters for n binary images is to use gradient descent method to minimize the special designed energy functional $E^{align}$ for each binary image corresponding to the fixed one, say the first binary image $B^1$ and the energy is defined as the following equation, according to equation E21:

$$E_{align}^j = \frac{\int\int_\Omega (\tilde{B}_j - B_1)^2 dA}{\int\int_\Omega (\tilde{B}_j + B_1)^2 dA} \quad \text{E21}$$

where $\Omega$ denotes the image domain, $B_j$ denotes the transformed image of $B_j$ based on the pose parameters p. Minimizing this energy is equivalent to minimizing the difference between current binary image and the fixed image in the training database. The normalization term in the denominator is employed to prevent the images from shrinking to alter the cost function. Hill climbing or Rprop method could be applied for the gradient descent.

FIG. 30 illustrates a 12-panel outline of a left ventricle determined by an experienced sonographer overlapped before alignment by gradient decent. The 12-panel images are overlapped via gradient decent into an aligned shape composite per process block 266 of FIG. 23.

FIG. 31 illustrates a 12-panel outline of a left ventricle determined by an experienced sonographer that is overlapped by gradient decent alignment between zero and level set outlines. Once gradient decent alignment has been accomplished per process block 264 of FIG. 23, additional procedures leading to Principle Components Analysis (PCA) may be performed for acquiring implicit parametric shape parameters from which the segmentation phase may be undertaken.

One approach to represent shapes is via point models where a set of marker points is used to describe the boundaries of the shape. This approach suffers from problems such as numerical instability, inability to accurately capture high curvature locations, difficulty in handling topological changes, and the need for point correspondences. In order to overcome these problems, an Eulerian approach to shape representation based on the level set methods could be utilized.

The signed distance function is chosen as the representation for shape. In particular, the boundaries of each of the aligned shapes are embedded as the zero level set of separate signed distance functions $\{\Psi_1, \Psi_2, \ldots, \Psi_n\}$ with negative distances assigned to the inside and positive distances assigned to the outside of the object. The mean level set function describing the shape value parameters $\Phi$ defined in process block 272 of FIG. 23 may be applied to the shape database as the average of these signed distance functions of process block 266, can be computed as shown in equation E22:

$$\overline{\Phi} = \frac{1}{n}\sum_{i=1}^n \Psi_i. \quad \text{E22}$$

To extract the shape variabilities, $\overline{\Phi}$ is subtracted from each of the n signed distance functions to create n mean-offset functions $\{\tilde{\psi}_1, \tilde{\psi}_2, \ldots, \tilde{\psi}_n\}$. These mean-offset functions are analyzed and then used to capture the variabilities of the training shapes.

Specifically, n column vectors are created, $\tilde{\psi}_i$, from each $\tilde{\Psi}_i$. A natural strategy is to utilize the $N_1 \times N_2$ rectangular grid of the training images to generate $N=N_1 \times N_2$ lexicographically ordered samples (where the columns of the image grid are sequentially stacked on top of one other to form one large column). Next, define the shape-variability matrix S as: $S=[\tilde{\psi}_1, \tilde{\psi}_2, \ldots, \tilde{\psi}_n]$.

FIG. 32 illustrates the procedure for creation of a matrix S of a $N_1 \times N_2$ rectangular grid. From this grid an eigenvalue decomposition is employed as shown in equation E23:

$$\frac{1}{n}SS^T = U\Sigma U^T \quad \text{E23}$$

Here U is a matrix whose columns represent the orthogonal modes of variation in the shape $\Sigma$ is a diagonal matrix whose diagonal elements represent the corresponding nonzero eigenvalues. The N elements of the ith column of U, denoted by $U_i$, are arranged back into the structure of the $N_1 \times N_2$ rectangular image grid (by undoing the earlier lexicographical concatenation of the grid columns) to yield $\Phi_i$, the ith principal mode or eigenshape. Based on this approach, a maximum of n different eigenshapes $\{\Phi_1, \Phi_2, \ldots, \Phi_n\}$ are generated. In most cases, the dimension of the matrix $$\frac{1}{n}SS^T$$

is large so the calculation of the eigenvectors and eigenvalues of this matrix is computationally expensive. In practice, the eigenvectors and eigenvalues of $$\frac{1}{n}SS^T$$

can be efficiently computed from a much smaller n×n matrix W given by $$\frac{1}{n}S^TS.$$

It is straightforward to show that if d is an eigenvector of W with corresponding eigenvalue λ, then Sd is an eigenvector of $$\frac{1}{n}SS^T$$

with eigenvalue λ.

For segmentation, it is not necessary to use all the shape variabilities after the above procedure. Let k≦n, which is selected prior to segmentation, be the number of modes to consider, k may be chosen large enough to be able to capture the main shape variations present in the training set.

FIG. 33 illustrates a 12-panel training eigenvector image set generated by distance mapping per process block 268 to extract mean eigen shapes.

FIG. 34 illustrates the 12-panel training eigenvector image set wherein ventricle boundary outlines are overlapped.

The corresponding eigenvalues for the 12-panel training images from FIG. 33 are 1054858.250000, 302000.843750, 139898.265625, 115570.250000, 98812.484375, 59266.875000, 40372.125000, 27626.216797, 19932.763672, 12535.892578, 7691.1406, and 0.000001.

From these shapes and values the shape knowledge for segmentation is able to be determined via a new level set function defined in equation E24:

$$\Phi[w](x, y) = \overline{\Phi}(\tilde{x}, \tilde{y}) + \sum_{i=1}^{k} w_i \Phi_i(\tilde{x}, \tilde{y}) \quad \text{E24}$$

Here $w=\{w_1, w_2, \ldots, w_k\}$ are the weights for the k eigenshapes with the variances of these weights $\{\sigma_1^2, \sigma_2^2, \ldots, \sigma_k^2\}$ given by the eigenvalues calculated earlier. Now we can use this newly constructed level set function Φ as the implicit representation of shape as shape values. Specifically, the zero level set of Φ describes the shape with the shape's variability directly linked to the variability of the level set function. Therefore, by varying w, Φ can be changed which indirectly varies the shape. However, the shape variability allowed in this representation is restricted to the variability given by the eigenshapes.

FIG. 35 illustrated the effects of using different w or k-eigenshapes to control the appearance and newly generated shapes. Here one shape generates a 6-panel image variation composed of three eigen value pairs in +1 and −1 signed values.

The segmentation shape modeling of FIG. 23 begins with process block 270 to undergo addition processes to account for shape variations or differences in poses. To have implicit representation the flexibility of handling pose variations, p is added as another parameter to the level set function according to equation E25:

$$\Phi[w, p](x, y) = \overline{\Phi}(\tilde{x}, \tilde{y}) + \sum_{i=1}^{k} w_i \Phi_i(\tilde{x}, \tilde{y}) \quad \text{E25}$$

As a segmentation using shape knowledge, the task is to calculate the w and pose parameters p. The strategy for this calculation is quite similar as the image alignment for training. The only difference is the special defined energy function for minimization. The energy minimization is based on Chan and Vese's active model (T. F. Chan and L. A. Vese. Active contours without edges. IEEE Transactions on Image Processing, 10: 266-277, 2001) as defined by following equations E26-E35:

$$R^u=\{(x, y)\in R^2:\Phi(x, y<0)\}$$

$$R^v=\{(x, y)\in R^2:\Phi(x, y>0)\} \quad \text{E26}$$

$$R^u:A_u=\int\int_\Omega H(-\Phi[w, p])dA \quad \text{area in E27}$$

$$R^v:A_v=\int\int_\Omega H(\Phi[w, p])dA \quad \text{area in E28}$$

$$R^u:S_u=\int\int_\Omega IH(-\Phi[w, p])dA \quad \text{sum intensity in E29}$$

$$R^v:S_v=\int\int_\Omega IH(\Phi[w, p])dA \quad \text{sum intensity in E30}$$

average intensity in E31:

$$R^u:\mu=\frac{S_u}{A_u}$$

average intensity in E32:

$$R^v:\nu=\frac{S_v}{A_v}$$

where E33:

$$H(\Phi[w, p]) = \begin{cases} 1, & \text{if } \Phi[w, p] \geq 0 \\ 0 & \text{if } \Phi[w, p] < 0 \end{cases}$$

$$E_{cv}=\int_{R^u}(I-\mu)^2dA+\int_{R^v}(I-\nu)^2dA \quad \text{E34}$$

E35:

$$E_{cv} = -(\mu^2 A_u + \nu^2 A_v) = -\left(\frac{S_u^2}{A_u} + \frac{S_v^2}{A_v}\right)$$

The definition of the energy could be modified for specific situation. In a particular embodiment, the design of the energy includes the following factors in addition to the average intensity, the standard deviation of the intensity inside the region.

Once the 3D volume image data could be reconstructed, a 3D shape model could also be defined in other particular embodiments having modifications of the 3D signed distance, the Degrees of Freedom (DOFs) (for example the DOF could be changed to nine, including transition in x, y, z, rotation α, β, θ, scaling factor sx, sy, sz), and modifications of the principle component analysis (PCA) to generate other decomposition matrixes in 3D space. One particular embodiment for determining the heart chamber ejection fractions is also to access how the 3D space could be affected by 2D measurements obtained over time for the same real 3D volume.

FIG. 36 is an image of variation in 3D space affected by changes in 2D measurements over time. Presented are three views of 2D+time echocardiographic data collected by transceivers 10A-E. The images are based on 24 frames taken at different time points, has a scaling factor in time dimension as 10 and is tri-linear interpolated in a 3D data set with pixel size as 838 by 487 by 240.

FIG. 37 is a 7-panel phantom training image set compared with a 7-panel aligned set. The left column are original 3D training data set in three views and the right column is a 7-panel image set of the original 3D training data set after alignment in three views. The phantom is synthesized as a simulation for the 2D+time echocardiographic data.

FIG. 38 is a phantom training set comprising variations in shapes. The left 3-panel column presenting an average shape −0.5 variation, the right 3-panel column presenting an average shape +0.5 variation, the middle image with overlapping crosshairs represents the average extracted shape from the phantom measurements.

FIG. 39 illustrates the restoration of properly segmented phantom measured structures from an initially compromised image using the aforementioned particular image training and segmentation embodiments. The top image has two differently sized and shaped hourglasses and an oval that is lacks boundary delineation. The second image from the top depicts the initial position of the average shape in the original 3D image, which is presented in a white outline and is off-center from the respective shapes. The second image from the top depicts the final segmentation result but still off-centered. The bottom image depicts a comparison between manual segmentation and automated segmentation. Here there is virtual overlap and shape alignment for the manually segmented and the automatic segmented shapes.

FIG. 40 schematically depicts a particular embodiment to determine shape segmentation of a ROI. An ROI is defined and gives the initialization of the shape based segmentation. The mass area (shown in light shadow), center, and longest axis of the ROI are computed. There after, the area of ROI is determined of to help decide the initial scaling factor. The scaling factor is defined as the square root of the quotient of the ROI area and the area's average shape. The direction of the longest axis (theta based on the y-axis) is used to determine the initial rotational angle. The center of the mass determines the initial transition in the x and in y-axes. Thereafter the detected shadow is used to remove the interference from the non-LV region and the average contour from training system on the mass center is computed from the ROI into a created object sub image. The region based segmentation within the sub region is undertaken by the aforementioned method particular embodiments.

FIG. 41 illustrates an exemplary transthoracic apical view of two heart chambers. The hand-held transceivers 10A-D substantially captures two chambers of a heart (outlined in dashed line) within scan plane 42. The two chamber view within the single scan plane 42 of a 3D dataset is collected at maximum mitral valve centering as described for FIG. 8 by procedures undertaken in sub-algorithm 280 of FIG. 24.

FIG. 42 illustrates other exemplary transthoracic apical views as panel sets associated with different rotational scan plane angles. The panel sets illustrated are associated with rotational scan planes θ angles 0, 30, 60 and 90 degrees.

FIG. 43 illustrates a left ventricle segmentation from different weight values w applied to a panel of eigenvector shapes. Here a panel of three eigenvectors pairs are weighted at w=+1 and w=−1 for a total of six segmentation shapes. The mean or average model segmentation shape from the six-segmented shapes is shown.

FIG. 44 illustrates exemplary Left Ventricle segmentations using the trained level-set algorithms. The segmentations are from a collection of 2D scan planes contained within a 3D data set acquired during an echocardiographic procedure in particular embodiments previously described by the systems illustrated in FIGS. 12-19 and methods in FIGS. 20-25. Scan planes are 30, 60, and 90 degrees and show the original image, the image as resulting from procures having some computational cost (Inverted with histogram equalization), the original image modified with sonographer-overlaid segmentation, the original image modified by the computational cost and initial average segmented shape associated with the trained level-set algorithms, and final average segmented shape as determined by the trained level-set algorithms. Other echocardiographic particular embodiments may obtain initial and final segmentation as determined by the trained level-set algorithms under a 2D+ time analysis image acquisition mode to more readily handle pose variations described above and to compensate for segmentation variation and the correspondingly Left ventricle area variation arising during movement of the heart while beating.

Validation data for determining volumes of heart chambers using the level-set algorithms is shown in the Table 1 for 33 data sets and compared with manual segmentation values. For each angle, there are 24 time-based that provide 864 2D-segmentations (=24×36).

TABLE 1

| | 1002 | 1003 | 1006 | 1007 | 1012 | 1016 | 1017 | Total frames (Data sets) |
|---|---|---|---|---|---|---|---|---|
| Angle 0 | | ✓ | ✓ | ✓ | ✓ | ✓ | ✓ | 144 (6) |
| Angle 30 | ✓ | ✓ | ✓ | ✓ | ✓ | ✓ | ✓ | 168 (7) |
| Angle 60 | ✓ | ✓ | | ✓ | ✓ | ✓ | ✓ | 144 (6) |
| Angle 90 | | ✓ | ✓ | ✓ | ✓ | ✓ | ✓ | 144 (6) |
| Angle 300 | | | ✓ | ✓ | ✓ | ✓ | ✓ | 120 (5) |
| Angle 330 | ✓ | | ✓ | ✓ | ✓ | ✓ | ✓ | 144 (6) |
| | | | | | | | | 864 (36) |

The manual segmentation is stored in .txt file, in which the expert-identified landmarks are stored. The .txt file is with the name as following format: **-XXX-outline.txt where ** is the data set number and XXX is the angle. Table 2 below details segmentation results by the level-set algorithms. When these landmarks are used for segmentation, linear interpolation may be used to generate closed contour.

TABLE 2

| Sonographer-located landmark | Level-set algorithm determined X-axis landmark location | Level-set algorithm determined Y-axis landmark location | Time stamp (frame number) for landmark placement |
|---|---|---|---|
| 1 | 395 | 313 | 1 |
| 2 | 380 | 312 | 1 |
| 41 | 419 | 315 | 1 |
| 42 | 407 | 307 | 2 |
| 73 | 446 | 304 | 2 |
| 74 | 380 | 301 | 3 |
| 110 | 459 | 295 | 3 |
| 860 | 435 | 275 | 24 |

Training the level-set algorithm's segmentation methods to recognize shape variation from different data sets having different phases and/or different viewing angles is achieved by processing data outline files. The outline files are classified into different groups. For each angle within the outline files, the corresponding outline files are combined into a single outline file. At the same time, another outline file is generated including all the outline files. Segmentation training also involves several schemes. The first scheme trains part of the segmentation for each data set (fixed angle). The second scheme trains via the segmentation for fixed angle from all the data sets. The third scheme trains via the segmentation for all the segmentation for all angles.

For a validation study 75-2D segmentation results were selected from 3D datasets collected for different angles from Table 1. The angles randomly selected are 1002 1003 1007 1016.

Validation methods include determining positioning, area errors, volume errors, and/or ejection fraction errors between the level-set computer readable medium-generated contours and the sonographer-determined segmentation results. Area errors of the 2D scan use the following definitions: A denotes the automatically-identified segmentation area, M the manually-identified segmentation area determined by the sonographer. Ratios of overlapping areas were assessed by applying the similarity Kappa index (KI) and the overlap index, which are defined as:

$$KI = 2 \times \frac{AIM}{A + M}$$

$$overlap = \frac{AIM}{AYM}$$

Volume error: (3D) After 3D reconstruction, the volume of the manual segmentation and automated segmentation are compared using the similar validation indices as the area error.

Ejection fraction (EF) error in 4D (2D+time) is computed using the 3D volumes at different heart phases. The EF from manual segmentation with the EF from auto segmentation are compared.

Results: The training is done using the first 12 images for the 4 different angles of data set 1003. Collected training sets for 4 different angles, 0, 30, 60 and 90 are created. The segmentation was done for the last 12 image for the 4 different angles of data set 1003. Subsequently, the segmentation for 4 different angles, 0, 30, 60 and 90 degrees was collected and are respectively presented in Tables 3-6 below.

TABLE 3

(angle 1003-000):

| Data 1003-000 | unsigned positioning error (in mms) | signed positioning error (in mms) | Auto area (in mms) | Manual area (in mms) | Overlapping area (in mms) | KI 2*O/(A + M) | Overlapping O/(A or M) |
|---|---|---|---|---|---|---|---|
| frame 13 | 3.661566 | 3.344212 | 2788.387 | 2174.345486 | 2138.234448 | 0.861717 | 0.757032 |
| frame 14 | 3.634772 | 3.222219 | 2918.387 | 2299.888968 | 2250.409162 | 0.862511 | 0.758258 |
| frame 15 | 3.406509 | 2.938201 | 2953.883 | 2395.160643 | 2336.000006 | 0.873427 | 0.775296 |
| frame 16 | 6.847305 | 6.658746 | 3041.164 | 1764.52362 | 1743.471653 | 0.725587 | 0.56935 |
| frame 17 | 5.696813 | 5.554389 | 2853.694 | 1813.849761 | 1796.793058 | 0.769909 | 0.625897 |
| frame 18 | 3.570965 | 2.28045 | 3001.365 | 2533.919227 | 2414.983298 | 0.872578 | 0.773953 |
| frame 19 | 3.819476 | 2.335655 | 2909.474 | 2486.437054 | 2312.028423 | 0.856956 | 0.749713 |
| frame 20 | 4.694806 | 2.774984 | 3149.651 | 2741.058289 | 2482.44179 | 0.842833 | 0.728359 |
| frame 21 | 3.422007 | 2.055935 | 2848.469 | 2498.730173 | 2321.555591 | 0.868326 | 0.767293 |
| frame 22 | 6.691374 | 6.41405 | 2994.45 | 1804.783586 | 1773.743459 | 0.739178 | 0.586266 |
| frame 23 | 4.787031 | 4.286448 | 2901.483 | 2126.555985 | 2064.629396 | 0.766664 | 0.621618 |

TABLE 3-continued (angle 1003-000):

| Data 1003-000 | unsigned positioning error (in mms) | signed positioning error (in mms) | Auto area (in mms) | Manual area (in mms) | Overlapping area (in mms) | KI 2*O/(A + M) | Overlapping O/(A or M) |
|---|---|---|---|---|---|---|---|
| frame 24 | 4.724921 | 3.749576 | 2895.337 | 2303.576904 | 2174.49915 | 0.836521 | 0.718982 |
| | | Max Area (ED - end-diastolic) | 3149.651 | 2741.053289 | | | |
| | | Min Area (ES - end-systolic) | 2788.387 | 1764.52362 | | | |
| | | EF (1-ES/ED) | | | | | |
| ave | 4.579795417 | 3.80123875 | | | | 0.8230173 | 0.7026685 |
| std | 1.24222826 | 1.5997941 | | | | 0.0558833 | 0.0783376 |

FIG. 45 is a plot of the level-set automated left ventricle area vs. the sonographer or manually measured area of angle 1003-000 from Table 3.

FIG. 46 is a plot of the level-set automated left ventricle area vs. the sonographer or manually measured area of angle 1003-030 from Table 4.

TABLE 4

(angle 1003-030):

| Data 1003-030 Data 1003-030 | unsigned positioning error (in mms) | signed positioning error (in mms) | Auto area (in mms) | Manual area (in mms) | Overlapping area (in mms) | KI 2*O/(A + M) | Overlapping O/(A or M) |
|---|---|---|---|---|---|---|---|
| frame 13 | 2.19382 | 2.160323 | 3308.847 | 2799.60427 | 2795.76267 | 0.915375 | 0.843956 |
| frame 14 | 0.870204 | −0.104675 | 3252.145 | 3293.019348 | 3163.634267 | 0.966709 | 0.935563 |
| frame 15 | 2.714477 | 0.575919 | 2761.496 | 2686.353907 | 2422.820161 | 0.889459 | 0.800925 |
| frame 16 | 5.183792 | 4.942926 | 2718.162 | 1771.438499 | 1735.020133 | 0.772906 | 0.629867 |
| frame 17 | 2.541074 | −1.125789 | 2690.964 | 3002.133411 | 2532.382588 | 0.889633 | 0.801206 |
| frame 18 | 1.882148 | 0.187478 | 3122.145 | 3104.012638 | 2886.578089 | 0.927242 | 0.864354 |
| frame 19 | 1.934285 | −0.736144 | 3156.412 | 3373.231952 | 3018.729122 | 0.924623 | 0.859813 |
| frame 20 | 2.289288 | −1.470268 | 2713.245 | 3078.360751 | 2625.656631 | 0.906713 | 0.829345 |
| frame 21 | 3.722941 | −0.242956 | 2596.921 | 2725.077233 | 2240.881995 | 0.906073 | 0.84212 |
| frame 22 | 4.493668 | 2.607496 | 2543.193 | 2092.903571 | 1880.232606 | 0.81111 | 0.682241 |
| frame 23 | 2.40633 | 0.700761 | 2642.252 | 2522.0871 | 2313.718727 | 0.896037 | 0.811654 |
| frame 24 | 2.22815 | −1.754062 | 2514.097 | 2971.554277 | 2466.614399 | 0.899297 | 0.81702 |
| | | Max Area (ED - end-diastolic) | 3308.847 | 3373.231952 | | | |
| | | Min Area. (ES - end-systolic) | 2514.097 | 1771.438499 | | | |
| | | EF (1-ES/ED) | | | | | |
| ave | 2.760577909 | 0.325516909 | | | | 0.889982 | 0.806737091 |
| std | 1.244070529 | 1.950425351 | | | | 0.053912517 | 0.084541431 |

TABLE 5

(angle 1003-060):

| Data 1003-060 | unsigned positioning error (in mms) | signed positioning error (in mms) | Auto area (in mms) | Manual area (in mms) | Overlapping area (in mms) | KI 2*O/(A + M) | Overlapping O/(A or M) |
|---|---|---|---|---|---|---|---|
| frame 13 | 5.402612 | 1.131598 | 2096.055 | 2077.384 | 1627.455339 | 0.780098 | 0.639476 |
| frame 14 | 6.067347 | 0.724424 | 1892.987 | 1996.556 | 1431.533749 | 0.736094 | 0.582396 |
| frame 15 | 4.970993 | 1.225224 | 2686.508 | 2607.524 | 2157.749775 | 0.815163 | 0.687996 |
| frame 16 | 5.421482 | 1.441104 | 2499.498 | 2455.858 | 1950.149722 | 0.787088 | 0.648924 |
| frame 17 | 5.145954 | −1.543341 | 2247.182 | 2750.893 | 1954.452314 | 0.782082 | 0.642147 |
| frame 18 | 5.2217 | 0.651928 | 2267.312 | 2343.53 | 1813.388769 | 0.786576 | 0.648229 |
| frame 19 | 7.271475 | 1.621387 | 1998.861 | 2074.464 | 1420.623606 | 0.697525 | 0.535538 |
| frame 20 | 6.651073 | 2.366935 | 2334.002 | 2204.156 | 1653.578218 | 0.728744 | 0.573247 |
| frame 21 | 6.598955 | 1.980833 | 2708.943 | 2615.361 | 2013.151959 | 0.756212 | 0.607991 |
| frame 22 | 5.943021 | 1.79845 | 2591.082 | 2530.385 | 1988.104728 | 0.776381 | 0.634496 |
| lPme 23 | 5.499417 | −1.160939 | 2336.154 | 2682.205 | 1942.620186 | 0.774205 | 0.631595 |
| frame 24 | 6.543109 | 1.373915 | 2343.53 | 2379.641 | 1767.135908 | 0.748284 | 0.597806 |
| | | Max Area (ED - end-(diastolic) | 2708.943 | 2750.893 | | | |
| | | Min Area (ES - end-systolic) | 1892.987 | 1996.556 | | | |
| | | EF (1-ES/ED) | | | | | |
| ave | 5.939502364 | 0.95272 | | | | 0.762578 | 0.617306 |
| std | 0.751069178 | 1.246998298 | | | | 0.033122 | 0.042875 |

FIG. 47 is a plot of the level-set automated left ventricle area vs. the sonographer or manually measured area of angle 1003-060 from Table 5.

TABLE 6

(angle 1003-090):

| Data 1003-090 | unsigned positioning error (in mms) | signed positioning error (in mms) | Auto area (in mms) | Manual area (in mms) | Overlapping area (in mms) | KI 2*O/(A + M) | Overlapping O/(A or M) |
|---|---|---|---|---|---|---|---|
| frame 13 | 4.890372 | 0.386783 | 2791.767 | 2897.181 | 2341.993 | 0.823348 | 0.699738 |
| frame 14 | 4.845072 | −0.237482 | 2580.479 | 2835.562 | 2206.461 | 0.814737 | 0.687461 |
| frame 15 | 2.913541 | −2.216814 | 2590.007 | 3139.509 | 2531.922 | 0.883817 | 0.791821 |
| frame 16 | 9.910783 | 8.934044 | 3650.903 | 2067.549 | 1931.71 | 0.675606 | 0.510125 |
| frame 17 | 6.945058 | 4.461438 | 2608.907 | 2072.927 | 1763.448 | 0.753315 | 0.604254 |
| frame 18 | 3.467966 | 2.314185 | 3071.897 | 2660.231 | 2512.406 | 0.876605 | 0.780318 |
| frame 19 | 3.62614 | 1.123661 | 2676.673 | 2524.392 | 2233.352 | 0.858806 | 0.75255 |
| frame 20 | 3.831596 | −0.535588 | 2537.146 | 2803.139 | 2241.65 | 0.839525 | 0.723432 |
| frame 21 | 3.344675 | 0.791006 | 2541.756 | 2517.631 | 2161.13 | 0.854305 | 0.745666 |
| frame 22 | 4.183485 | 2.231353 | 2580.94 | 2266.237 | 2037.738 | 0.840794 | 0.725319 |

TABLE 6-continued (angle 1003-090):

| Data 1003-090 | unsigned positioning error (in mms) | signed positioning error (in mms) | Auto area (in mms) | Manual area (in mms) | Overlapping area (in mms) | KI 2*O/(A + M) | Overlapping O/(A or M) |
|---|---|---|---|---|---|---|---|
| frame 23 | 3.734046 | 3.58284 | 3136.436 | 2424.818 | 2405.917 | 0.865243 | 0.762491 |
| frame 24 | 3.189541 | 1.353026 | 2840.479 | 2604.451 | 2391.165 | 0.878309 | 0.783022 |
| | | Max Area (ED - end-diastolic) | 3650.903 | 3139.509 | | | |
| | | Min Area (ES - end-systolic) | 2537.146 | 2067.549 | | | |
| | | EF (1-ES/ED) | | | | | |
| ave | 4.544718455 | 1.981969909 | | | | 0.83101 | 0.715133 |
| std | 2.094832341 | 2.977565291 | | | | 0.063412 | 0.086357 |

FIG. 48 is a plot of the level-set automated left ventricle area vs. the sonographer or manually measured area of angle 1003-090 from Table 6.

Using the trained algorithms applied to the 3D data sets from the 3D transthoracic echocardiograms shows that these echocardiographic systems and methods provide powerful tools for diagnosing heart disease. The ejection fraction as determined by the trained level-set algorithms to the 3D datasets provides an effective, efficient and automatic measurement technique. Accurate computation of the ejection fractions by the applied level-set algorithms is associated with the segmentation of the left ventricle from these echocardiography results and compares favorably to the manually, laboriously determined segmentations.

The proposed shape based segmentation method makes use of the statistical information from the shape model in the training datasets. On one hand, by adjusting the weights for different eigenvectors, the method is able to match the object to be segmented with all different shape modes. On the other hand, the topology-preserving property can keep the segmentation from leakage which may be from the low quality echocardiography.

FIG. 49 illustrates the 3D-rendering of a portion of the Left Ventricle from 30 degree angular view presented from six scan planes obtained at systole and/or diastole. Here the planar shapes of a 12-panel 2D image set are rendered to provide a portion of the Left Ventricle as a combined 3D rendering of systole and/or diastole measurements. More particularly, the upper image set encompasses 2D views of the left ventricle at different heart phases and overlapped with the segmentation results of the images contained in the six scan planes acquired at the 30-degree locus. The lower image indicates the range of motion of the left ventricular endocardium between systole and diastole viewable from the 30-degree locus from the segmented 2D images of the six scan planes.

Left Ventricular Mass (LVM): LV hypertrophy, as defined by echocardiography, is a predictor of cardiovascular risk and higher mortality. Anatomically, LV hypertrophy is characterized by an increase in muscle mass or weight. LVM is mainly determined by two factors: chamber volume, and wall thickness. There are two main assumptions in the computation of LVM: 1) the interventricular septum is assumed to be part of the LV and 2) the volume, $V_m$, of the myocardium is equal to the total volume contained within the epicardial borders of the ventricle, $V_t$(epi), minus the chamber volume, $V_c$(endo); $V_m$ is defined by equation E36 and LVM is obtained by multiplying $V_m$ by the density of the muscle tissue (1.05 g/cm) according to E37:

$$V_m = V_t(\text{epi}) - V_c(\text{endo}) \quad \text{E36}$$

$$LVM = 1.05 \times V_m \quad \text{E37}$$

LVM is usually normalized to total body surface area or weight in order to facilitate interpatient comparisons. Normal values of LVM normalized to body weight are 2.4±0.3 g/kg [42].

Stroke Volume (SV): is defined as the volume ejected between the end of diastole and the end of systole as shown in E38:

$$SV = \text{end\_diastolic\_volume}(EDV) - \text{end\_systolic\_volume}(ESV) \quad \text{E38}$$

Alternatively, SV can be computed from velocity-encoded MR images of the aortic arch by integrating the flow over a complete cardiac cycle [54]. Similar to LVM and LVV, SV can be normalized to total body surface. This corrected SV is known as SVI (Stroke volume index). Healthy subjects have a normal SVI of 45±8 ml/m [42].

Ejection Fraction (EF): is a global index of LV fiber shortening and is generally considered as one of the most meaningful measures of the LV pump function. It is defined as the ratio of the SV to the EDV according to E39:

$$EF = \frac{SV}{EDV} \times 100\% = \frac{EDV - ESV}{EDV} \times 100\% \quad \text{E39}$$

Cardiac Output (CO): The role of the heart is to deliver an adequate quantity of oxygenated blood to the body. This blood flow is known as the cardiac output and is expressed in liters per minute. Since the magnitude of CO is proportional to body surface, one person may be compared to another by means of the CI, that is, the CO adjusted for body surface area. Lorenz et al. [42] reported normal CI values of 2.9±0.6 l/min/m and a range of 1.74-4.03 l/min/m.

CO was originally assessed using Fick's method or the indicator dilution technique [55]. It is also possible to estimate this parameter as the product of the volume of blood ejected within each heart beat (the SV) and the HR according to E40:

$$CO = SV \times HR \quad \text{E40}$$

In patients with mitral or aortic regurgitation, a portion of the blood ejected from the LV regurgitates into the left atrium or ventricle and does not enter the systemic circulation. In these patients, the CO computed with angiocardiography exceeds the forward output. In patients with extensive wall motion abnormalities or misshapen ventricles, the determination of SV from angiocardiographic views can be erroneous. Three-dimensional imaging techniques provide a potential solution to this problem since they allow accurate estimation of the irregular LV shape.

FIG. 50 illustrates four images which are the training results from a larger training set. The four images are respectively, left to right, overlapping before alignment, overlapping after alignment, average level set, and zero level set of the average map respectively.

FIG. 51 illustrates a total of 16 shape variations with differing W values. The W values, left to right, are respectively, −0.2, −0.1, +0.1, and +0.2.

FIG. 52 presents an image result showing boundary artifacts of a left ventricle that arises by employing the estimate shadow regions algorithm 234 of FIG. 22. An original scan plane image on the upper left panel shows a left ventricle LV. The estimate shadow regions 234 processing block provides a negative 2-tone image of the left ventricle and shows potential segmentation complexities exhibited as two spikes $S_a$ and $S_b$ in the upper right panel image along the boundary of the left ventricle. An area fill is shown in the lower left panel image. A shadow of the original image panel is shown in the lower right image panel.

Figure 53:
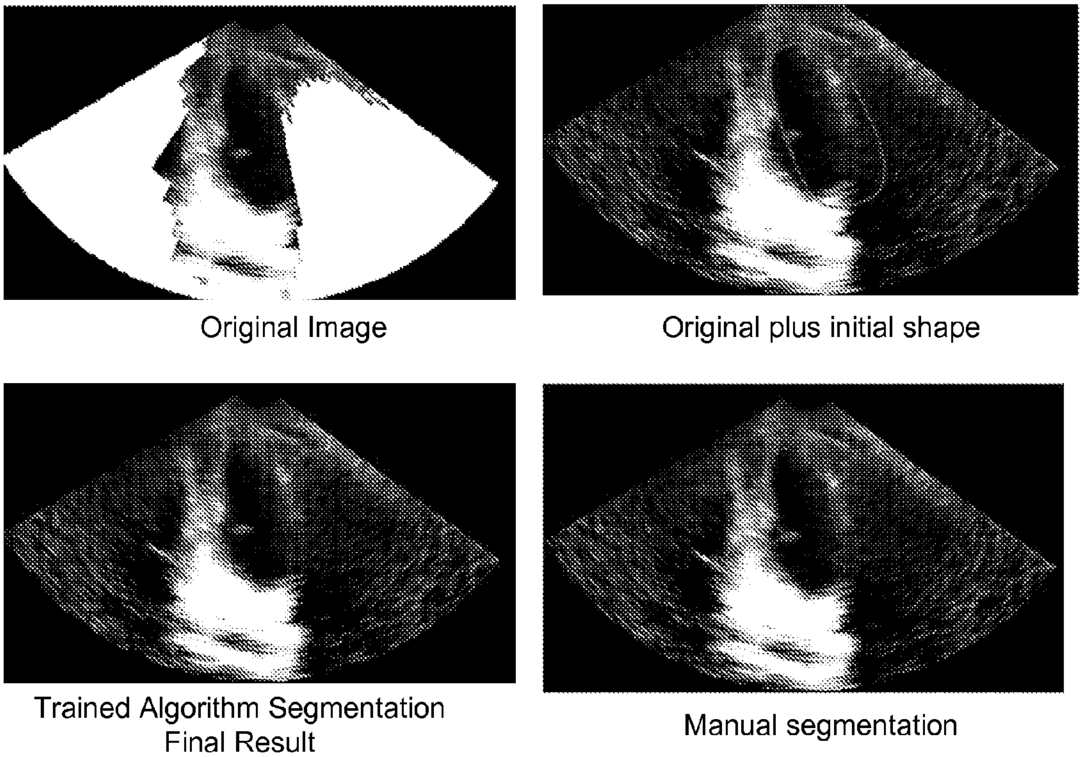

FIG. 53 illustrates a panel of exemplary images showing the incremental effects of application of level-set sub-algorithm 260 of FIG. 23. The upper left image is a portion of an original image of a Left Ventricle of a scan plane. The upper right is the original plus initial shape segmentation of the level-set algorithm obtained from process block 270 of sub-algorithm 260. The lower left image is the final segmentation result of the trained level-set algorithm exiting from processing block 276 of sub-algorithm 260. The lower right image is the sonographer determined segmentation. As can be seen the final trained level-set algorithm compares favorably with the manually segmented result of the sonographer.

FIG. 54 illustrates another panel of exemplary images showing the incremental effects of application of an alternate embodiment of the level-set sub-algorithm 260 of FIG. 23. The upper left image an original image of a Left Ventricle of a scan plane. The upper right is an inverse or negative two-tone image of the original. The middle left image is the original image masked with shadow. The middle right is the original plus initial shape segmentation of the level-set algorithm obtained from process block 270 of sub-algorithm 260. The lower left image is the final segmentation result of the trained level-set algorithm exiting from processing block 276 of sub-algorithm 260. The lower right image is the sonographer-determined segmentation. With this alternate level-set algorithm embodiment, it can be seen that the final trained level-set algorithm compares favorably with the manually segmented result of the sonographer.

FIG. 55 presents a graphic of Left Ventricle area determination as a function of 2D segmentation with time (2D+time) between systole and diastole by application of the particular and alternate embodiments of the level set algorithms of FIG. 23. As can be seen, the Left ventricle area presents a sinusoidal repetition and shows that both the particular embodiment of the automatic level-set algorithm of FIGS. 23 and 53 and the alternate embodiment described in FIG. 54 presents a favorable accuracy with the manual sonographer segmentation methods of FIGS. 21 and 22. The automatic level-set particular and alternate embodiments present segmentation areas substantially the same as the fully manual sonographer method across the range between diastole and/or systole.

FIGS. 56-58 collectively illustrates Bayesian inferential approaches to segmentation described by Mikael Rousson and Daniel Cremers in Efficient Kernel Density Estimation of Shape and Intensity Priors for Level Set Segmentation (MICCAI (2) 2005: 757-764). The complexities for determining organ boundary information from boundary-specific echogenic signals that is mixed with noise and background overlap from neighboring structures. By way of example, FIG. 56 illustrates the empirical probability of intensities inside and outside the left ventricle of an ultrasound cardio image. The echogenic intensity of the internal surface (dashed line) significantly overlaps with the echogenic intensity (solid line) of external surfaces of the left ventricle. The region-based segmentation of these structures is a challenging problem, because objects and background have similar histograms. The proposed segmentation scheme optimally exploits the estimated probabilistic intensity models in the Bayesian interface.

FIG. 57 depicts three panels in which schematic representations of a curved shaped eigenvector of a portion of a left ventricle is progressively detected when applied under uniform, Gaussian, and Kernel density pixel intensity distributions. The accuracy of segmentation is based on shape model employed and the region information signal intensity. The left frame shows a pattern of points associated in a portion of a scan plane having uniform signal probability densities and no shape. The middle frame shows the same pattern of points associated with an oval shape in which signal intensities are arranged in gaussian probability cluster. The right frame shows the pattern of points associated in a C-shape in the portion of a scan plane having kernel probability densities about the C-shape. The three panels have the same schematic representations of a curved shaped eigenvector of a portion of a left ventricle that is progressively detected when applied under uniform, Gaussian, and Kernel density pixel intensity distributions. A progression of improving resolved eigenshapes is seen from the left to the right panels. The curved-shaped pixel dataset represents a portion of the left ventricle. In the left panel, uniform pixel intensity of a scan plane is applied with the result that no eigen shapes are visible. In the middle panel, a Gaussian pixel intensity distribution is assumed and the curved-shaped pixel sets are contained within an eigen shaped oval pattern. In the right panel, a C-shaped eigenvector is rendered visible that encapsulates the curved pixel data set. That means we are trying to find $\alpha$ for different eigenshapes in the whole $\alpha$ space without any restriction. In the left panel, the $\alpha$ space of signed distance functions is not a linear space, therefore, the mean shape and linear combinations of eigenshapes are typically no longer signed distance functions and cannot be readily seen. In the Gaussian density of the middle panel, a portion of the signed functions allow the curve-shaped data sets to be contained with an oval space. In the right panel the greater proportion of signed functions allow a more certain and improved eigen shape that encompasses the curved-shape data points.

FIG. 58 depicts the expected segmentation of the left ventricle arising from the application of different a-priori model assumptions. In the top panel, a non-model assumption is applied with aberrantly shaped segmented structures that do not render the expected shaped of a left ventricle in that it is jagged and disjointed into multiple chambers. In the middle panel, a prior uniform model assumption is applied, and the left ventricle is partially improved, but does not having the expected shape and is still jagged. In the bottom panel, a prior kernel model is applied to the left ventricle. The resulting segmentation is more cleanly delineated and the ventricle boundary is smooth, has the expected shape, and does not significantly overlap into the inter-chamber wall.

FIG. 59 is a histogram plot of 20 left ventricle scan planes to determine boundary intensity probability distributions employed for establishing segmentation within training data sets of the left ventricle. Maxima for internal and external probability distributions for intensity of pixels residing on the internal or external segmentation line of the left ventricle interface in which pixel intensity along a boundary is compared to the pixel intensity distribution of the whole scan plane image. In the training data sets of a given scan plane, the average pixel intensity probability distribution is calculated and stored with the boundary histograms for segmentation.

FIG. 60 depicts a 20-panel training image set of aligned left ventricle shapes contained in Table 3. Principle component analysis extracts the eigenmodes from each left ventricle image and applies a kernel function to define the distribution of the shape prior and to acquire the eigenvectors obtained from the level-set algorithms described above. Table 6 lists vectors representing each training shape of four eigenmodes to represent the new shape or training shape. Each row represents the vector that corresponds to the training shape. The weights of each training shape are computed by projection to the basis formed by the eigenshapes.

TABLE 6

| | | | |
|---|---|---|---|
| 20 4 | | | |
| −0.108466 | −0.326945 | −0.011603 | −0.270630 |
| 0.201111 | 0.007938 | 0.205365 | −0.157808 |
| −0.084072 | −0.127009 | 0.110204 | −0.248149 |
| −0.004642 | 0.018199 | −0.201792 | −0.221856 |
| −0.055033 | −0.262811 | −0.324424 | −0.225715 |
| 0.210304 | 0.007946 | 0.000766 | 0.187720 |
| −0.219551 | −0.326738 | 0.195884 | 0.070594 |
| −0.204191 | 0.218314 | 0.000759 | 0.224303 |
| 0.066532 | −0.499781 | 0.037092 | 0.228500 |
| −0.461649 | −0.178653 | −0.316081 | 0.040002 |
| −0.383818 | −0.380613 | −0.140760 | 0.030318 |
| 0.005501 | 0.004479 | 0.018898 | 0.182005 |
| −0.194213 | 0.008519 | 0.017103 | 0.008163 |
| −0.453880 | 0.134978 | 0.037047 | 0.213359 |
| 0.191661 | −0.004739 | −0.003520 | −0.021242 |
| −0.278152 | 0.251390 | −0.500381 | 0.050353 |
| −0.480242 | −0.215070 | −0.161644 | 0.058304 |
| −0.114089 | 0.228670 | 0.284464 | 0.065447 |
| 0.062613 | 0.289096 | 0.113080 | −0.064892 |
| −0.646280 | −0.035933 | 0.089240 | −0.423474 |

FIG. 61 depicts the overlaying of the segmented left ventricle to the 20-image panel training set obtained by the application of level set algorithm generated eigen vectors of Table 6. The overlaid ventricle segmentation boundary is substantially reproduced and closely follows the contour of each training image. The vectors obtained by the level set algorithms in conjunction with the kernel function adequately and faithfully reconstruct the segmented boundary of the left ventricle, demonstrating the robustness of the system and methods of the particular embodiments.

FIG. 62 depicts the left ventricle segmentation resulting from application of a prior uniform shape statistical model. The prior uniform shape model employs level set trained algorithms applied to information contained in cardiographic echoes. The segmentation results of a subject's left ventricle boundary renders a jagged and spiked left ventricle with overlap into adjacent wall structures.

FIG. 63 depicts the segmentation results of a kernel shape statistical model applied to the echogenic image information of the subject's left ventricle. In the kernel model, the level set trained algorithms results in a smoother segmentation of expected shape without overlap into adjacent wall structures. The application of the kernel shape model with the level set trained algorithms obtained this higher resolving segmentation in only 0.13 seconds due to the fast processing speeds imparted by the level-set algorithms. Thus, the subject's left ventricle segmented shape is efficiently and robustly obtained with high resolution.

The application of the trained level set algorithms with the kernel shape model allows accurate 3D cardiac functioning assessment to be non-invasively and readily obtained for measuring changes in heart chambers. For example, the determination of atrial or ventricular stroke volumes defined by equation E37, ejection fractions defined by equation E38, and cardiac output defined by equation E39. Additionally, the inter-chamber wall volumes (ICWV), thicknesses (ICWT), masses (ICWM) and external cardiac wall volumes, thicknesses, and masses may be similarly determined from the segmentation results obtained by the level set algorithms. Similarly, these accurate, efficient and robust results may be obtained in 2D+time scenarios in situation in which the same scan plane or scan planes is/are sequentially measured in defined periods.

While the particular embodiments have been illustrated and described for determination of ICWT, ICWM, and left and right cardiac ventricular ejection fractions using trained algorithms applied to 3D data sets from 3D transthoracic echocardiograms (TTE), many changes can be made without departing from the spirit and scope of the invention. For example, applications of the disclosed embodiments may be acquired from other regions of interest having a dynamically repeatable cycle. For example, changes in lung movement. Accordingly, the scope of embodiments of the invention is not limited by the disclosure of the particular embodiments. Instead, embodiments of the invention should be determined entirely by reference to the claims that follow.

The embodiments of the invention in which an exclusive property or privilege is claimed are defined as follows:

1. A method for cardiac imaging, comprising:

creating a database of 3D images having manually segmented regions;

training level-set image processing algorithms to substantially reproduce the shapes of the manually segmented regions using a computer readable medium;

acquiring a non-database 3D image;

segmenting the regions of the non-database image by applying the trained level-set processing algorithms using the computer readable medium, and determining from the segmented non-database 3D image at least one of:

a volume of any heart chamber, and a thickness of the wall between any adjoining heart chambers.

2. The method of claim 1, wherein the manually segmented regions of the database of 3D images is determined by deriving information from the data content of the 3D images using a computer readable medium.

3. The method of claim 2, wherein deriving information using the computer readable medium further includes applying image processing algorithms.

4. The method of claim 3, wherein the image processing algorithms include image enhancement, segmentation, combine and clean-up.

5. The method of claim 4, wherein image enhancement includes sub-algorithms heat filter and shock filter, the heat filter being applied first, then followed by the shock filter.

6. The method of claim 5, wherein segmentation includes sub-algorithms intensity-based segmentation and edge-based segmentation, the intensity and edge-based segmentation being applied separately to the results of the shock filter.

7. The method of claim 5, wherein combine includes combining the results of intensity-based and edge-based segmentation sub-algorithms using a Boolean AND operator to produce a segmented image.

8. The method of claim 6, wherein clean-up includes at least one of filling gaps with pixels and removing pixel groups unrelated to at least one region of interest of the image.

9. The method of claim 4, wherein image enhancement includes sub-algorithms radon transfer, heat filter and shock filter, the radon transfer being applied first, followed by the heat filter, and then followed by shock filter.

10. The method of claim 9, wherein segmentation includes sub-algorithms region-based segmentation and gradients-based segmentation, the region and gradient-based segmentation being applied separately to the results of the shock filter.

11. The method of claim 10, wherein the region-based segmentation includes estimate shadow regions, automatic region threshold, and remove shadow regions, the shadow regions being applied to the results of the shock filter, followed by the automatic region threshold, and then followed by the remove shadow regions.

12. The method of claim 10, wherein the gradient-based segmentation includes spatial gradients and hysteresis threshold of gradients, the spatial gradients being applied to the results of the shock filter followed by the hysteresis threshold of gradients.

13. The method of claim 12, wherein spatial gradients further includes kernel density estimate.

14. The method of claim 12, wherein hysteresis threshold further includes non-parametric eigen shape estimation.

15. The method of claim 5, wherein combine includes combining the results of region-based and threshold-based segmentation sub-algorithms using a Boolean AND operator to produce a segmented image.

16. The method of claim 15, wherein cleanup includes at least one of morphological cleanup and snakes-based cleanup, wherein morphological cleanup includes at least one of filling gaps with pixels and removing pixel groups unrelated to at least one region of interest of the image and snakes-based cleanup being applied after morphological cleanup.

17. The method of claim 1, wherein training level-set image processing algorithms includes a training sub-algorithm and a segmentation sub-algorithm.

18. The method of claim 17, wherein the training sub-algorithm includes, in order, acquire apriori training shapes from the database, align the shapes by gradient decent, generate signed distance map, and principle component analysis.

19. The method of claim 17, wherein the segmentation sub-algorithm includes in order minimize shape parameters by gradient descent, update shape image value, determine inside and outside curvature lines from update, and curvature line convergence check.

20. The method of claim 1, wherein acquiring a non-database 3D image includes an ultrasound 3D data set comprising at least one of a plurality of scan planes and a plurality of 3D distributed scanlines comprised of ultrasound echoes collected by an ultrasound transceiver having a speaker.

21. The method of claim 20, wherein acquiring 3D data sets is achieved by an electrocardiograph in signal communication with the transceiver to acquire the 3D data sets at systole and diastole.

22. The method of claim 21, wherein acquiring a non-database 3D image further includes placing an ultrasound transceiver against a subject to transmit radio frequency ultrasound into the subject to detect a mitral valve of a heart from echoic pulses reflected from the heart.

23. The method of claim 22, wherein placing further includes re-positioning the transceiver in response to audible sounds emanating from the speaker that characterizes the centered location as determined by change in audio signals emanating from the speaker in proportion to a Doppler shift experienced by the received echoes.

24. The method of claim 1, wherein segmenting the regions of the non-database image by applying the trained image processing algorithms using the computer readable medium includes level-set sub-algorithms configured to determine the active contours and minimal distance curves of regions of interest of the non-database image using apriori geometric models of the regions of interest contained within the database.

25. The method of claim 22, wherein the level-set sub-algorithms further includes pose parameters in the form of a metric set of Cartesian and angular definitions of pixel locations constituting the 3D data set of the non-database image.

26. The method of claim 22, wherein determining from the segmented non-database 3D images acquired during systole and diastole further includes determining the change in volume of any heart chamber expressed as an ejection fraction.

27. The method of claim 26, wherein determining the change in heart chamber volume between systole and diastole cycles is expressed as a quotient of the difference between heart chamber volumes occurring at systole and diastole cycles and the volume of the chamber at diastole.

28. The method of claim 26, wherein determining the ejection fraction includes the ejection fraction for the left ventricle chamber expressed as a quotient of the difference between left ventricle volumes occurring at systole and diastole and the volume of the left ventricle at diastole.

29. A method for cardiac imaging comprising:

creating a database of 3D images having manually segmented regions;

training level-set image processing algorithms to substantially reproduce the shapes of the manually segmented regions using a computer readable medium;

acquiring non-database 3D images at systole and diastole;

segmenting the regions of the non-database images by applying the trained level-set processing algorithms using the computer readable medium, and determining from the segmented non-database 3D images at least one of:

a volume of any heart chamber, a thickness of the wall between any adjoining heart chambers, and a change in volume in any heart chamber between systole and diastole.

30. A system for cardiac imaging comprising:

a database of 3D images having manually segmented regions;

an ultrasound transceiver configured to deliver ultrasound pulses into and acquire ultrasound echoes from a subject as 3D image data sets;

an electrocardiograph to determine the timing to acquire the 3D data sets; and a computer readable medium configured to train level-set image processing algorithms to substantially reproduce the shapes of the manually segmented regions and to segment regions of interest of the 3D data sets using the trained algorithms, wherein at least one cardiac metric from the 3D data sets is determined from the segmented regions of interest.

31. The system of claim 30, wherein the ultrasound transceiver includes a speaker configurable to sense a Doppler shift of the ultrasound echoes affected by the movement of the mitral valve of the heart.

32. The system of claim 31, wherein the location to acquire 3D data sets is determined by the change in audible signals from the speaker in proportion to the Doppler shift.

33. The system of claim 32, wherein the 3D data sets are acquired during systole and diastole.

34. The system of claim 33, wherein the at least one cardiac metric further includes the change in volume of any heart chamber, the change in thickness of the wall between any adjoining heart chambers, and the change in volume of the wall between any adjoining heart chambers.

35. The system of claim 30, wherein the computer readable medium configured to train level-set image processing algorithms to substantially reproduce the shapes of the manually segmented regions includes a training sub-algorithm and a segmentation sub-algorithm.

36. The system of claim 35, wherein the training sub-algorithm includes, in order, acquire apriori training shapes from the database, align the shapes by gradient decent, generate signed distance map, and principle component analysis.

37. The system of claim 35, wherein the segmentation sub-algorithm includes in order minimize shape parameters by gradient descent, update shape image value, determine inside and outside curvature lines from update, and curvature line convergence check.

38. The system of claim 37, wherein the segmentation sub-algorithm includes in order minimize shape parameters by gradient descent, update shape image value, determine inside and outside curvature lines from update, and curvature line convergence check.

39. The system of claim 30, wherein the computer readable medium configured to segment regions of interest of the 3D data sets using the trained algorithms using includes level set algorithms that determine active contours and minimal distance curves of regions of interest of the 3D data sets using apriori geometric models of the regions of interest contained within the database.

40. The system of claim 39, wherein the at least one cardiac metric includes determining the ejection fraction of at least one heart chamber defined as the quotient of the change in the at least one heart chamber volume between systole and diastole cycles and the volume of the same at least one heart chamber at diastole.

41. The system of claim 40, wherein the at least one chamber includes a left ventricle, a right ventricle, a left atrium, and a right atrium.

42. A system for cardiac imaging comprising:

an ultrasound transceiver configured to determine the location to acquire ultrasound echo 3D data sets to image the left ventricle of a heart;

an electrocardiograph to determine the timing to acquire the 3D data sets at a systole and diastole; and a computer readable medium configured to train level-set image processing algorithms to substantially reproduce the shapes of the manually segmented regions and to segment regions of interest of the 3D data sets using the trained algorithms to determine between systole and diastole at least one of:

the thickness of a wall between the left ventricle and at least one of the adjoining heart chambers, the volume of the left ventricle, and the ejection fraction of the left ventricle.

* * * * *